US011150255B2

(12) United States Patent
Levner et al.

(10) Patent No.: US 11,150,255 B2
(45) Date of Patent: Oct. 19, 2021

(54) ADDITIVE CHANNELS

(71) Applicant: Emulate Inc., Boston, MA (US)

(72) Inventors: Daniel Levner, Brookline, MA (US); Christopher David Hinojosa, Cambridge, MA (US); Norman Wen, West Roxbury, MA (US); Jacob Fraser, Somerville, MA (US); Justin Nguyen, Medford, MA (US); Riccardo Barrile, Boston, MA (US); Geraldine Hamilton, Boston, MA (US); Catherine Karalis, Brookline, MA (US); Hyoungshin Park, Newton, MA (US); Antonio Varone, West Roxbury, MA (US); Andries Van der Meer, Enchede (NL); Monicah Otieno, Robbinville, NJ (US); David Conegliano, Boston, MA (US)

(73) Assignee: EMULATE, Inc., Boston, MA (US)

( * ) Notice: Subject to any disclaimer, the term of this patent is extended or adjusted under 35 U.S.C. 154(b) by 0 days.

(21) Appl. No.: 15/648,182

(22) Filed: Jul. 12, 2017

(65) Prior Publication Data

US 2018/0017586 A1     Jan. 18, 2018

Related U.S. Application Data

(60) Provisional application No. 62/361,274, filed on Jul. 12, 2016.

(51) Int. Cl.
*G01N 33/00* (2006.01)
*G01N 33/86* (2006.01)
(Continued)

(52) U.S. Cl.
CPC ............ *G01N 33/86* (2013.01); *B01L 3/5023* (2013.01); *B01L 3/502707* (2013.01);
(Continued)

(58) Field of Classification Search
CPC ....................................................... G01N 33/86
(Continued)

(56) References Cited

U.S. PATENT DOCUMENTS

| 6,130,098 A | 10/2000 | Handique et al. ............ 436/180 |
| 8,647,861 B2 | 2/2014 | Ingber et al. .............. 435/289.1 |

(Continued)

FOREIGN PATENT DOCUMENTS

| CN | 102732415 A | 10/2012 |
| CN | 105628747 A | 6/2016 |

(Continued)

OTHER PUBLICATIONS

Great Britain Office Action for the Great Britain Patent Application No. GB1711213.7 dated Jan. 15, 2018.
(Continued)

*Primary Examiner* — Christine T Mui
*Assistant Examiner* — Emily R. Berkeley
(74) *Attorney, Agent, or Firm* — Medlen & Carroll, LLP

(57) ABSTRACT

Compositions, devices and methods are described for preventing, reducing, controlling or delaying adhesion, adsorption, surface-mediated clot formation, or coagulation in a microfluidic device or chip. In one embodiment, blood (or other fluid with blood components) that contains anticoagulant is introduced into a microfluidic device comprising one or more additive channels containing one or more reagents that will re-activate the native coagulation cascade in the blood that makes contact with it "on-chip" before moving into the experimental region of the chip.

17 Claims, 54 Drawing Sheets

(51) Int. Cl.
  B01L 3/00      (2006.01)
  C12M 3/06      (2006.01)
  C12M 1/00      (2006.01)
  C12M 1/42      (2006.01)
  C12M 1/34      (2006.01)
  G01N 33/543    (2006.01)
  G01N 33/80     (2006.01)

(52) U.S. Cl.
  CPC ... B01L 3/502715 (2013.01); B01L 3/502746 (2013.01); B01L 3/502761 (2013.01); C12M 23/16 (2013.01); C12M 29/00 (2013.01); C12M 29/04 (2013.01); C12M 29/10 (2013.01); C12M 35/08 (2013.01); C12M 41/46 (2013.01); G01N 33/54366 (2013.01); G01N 33/80 (2013.01); B01L 2200/02 (2013.01); B01L 2200/027 (2013.01); B01L 2200/0605 (2013.01); B01L 2200/0647 (2013.01); B01L 2200/16 (2013.01); B01L 2300/0809 (2013.01); B01L 2300/0816 (2013.01); B01L 2300/0867 (2013.01); B01L 2300/0883 (2013.01); B01L 2300/0887 (2013.01); B01L 2300/14 (2013.01); B01L 2300/16 (2013.01); G01N 2500/10 (2013.01)

(58) Field of Classification Search
  USPC ......................................................... 422/502
  See application file for complete search history.

(56) References Cited

U.S. PATENT DOCUMENTS

| | | |
|---|---|---|
| 2004/0038997 A1 | 2/2004 | Macey ............................. 435/2 |
| 2006/0094119 A1 | 5/2006 | Ismagilov et al. .............. 436/55 |
| 2009/0317793 A1 | 12/2009 | Jonsmann et al. ......... 435/287.2 |
| 2011/0244595 A1 | 10/2011 | Chung et al. ................ 436/501 |
| 2014/0036299 A1 | 2/2014 | Norota ......................... 358/1.14 |
| 2014/0142370 A1 | 5/2014 | Wong et al. .................... 600/36 |
| 2015/0114093 A1 | 4/2015 | Appleyard et al. .......... 73/61.59 |
| 2016/0069913 A1 | 3/2016 | Bakhru et al. ................ 422/500 |
| 2016/0091455 A1 | 3/2016 | Taylor et al. .............. 422/82.03 |
| 2016/0123857 A1* | 5/2016 | Kapur .................. G01N 1/4077 435/2 |
| 2017/0058243 A1 | 3/2017 | Levner et al. ................ 422/502 |

FOREIGN PATENT DOCUMENTS

| | | |
|---|---|---|
| EP | 2040073 A1 | 3/2009 |
| WO | WO/2001/059425 | 8/1901 |
| WO | WO/2014/183886 | 11/1914 |
| WO | WO/2009/042522 | 4/2009 |
| WO | WO/2010/009307 | 1/2010 |

OTHER PUBLICATIONS

PCT International Search Report of International Application No. PCT/US2017/041668 dated Sep. 11, 2017.

André, P. et al. (2002) "Platelet-Derived CD40L: The Switch-Hitting Player of Cardiovascular Disease," *Circulation* 106(8), 896.

Barstad, R. M. et al. (1998) "Monocyte Procoagulant Activity Induced by Adherence to an Artificial Surface Is Reduced by End-point Immobilized Heparin-coating of the Surface," *Thrombosis and Haemostasis* 79(2), 302-305.

Boumpas, D. T. et al. (2003) "A short course of BG9588 (anti-CD40 ligand antibody) improves serologic activity and decreases hematuria in patients with proliferative lupus glomerulonephritis," *Arthritis & Rheumatism* 48(3), 719-727.

Branchford, B. R. et al. (2015) "Microfluidic technology as an emerging clinical tool to evaluate thrombosis and hemostasis," *Thrombosis Research* 136(1), 13-19.

Chan, A. C. et al. (2010) "Therapeutic antibodies for autoimmunity and inflammation," *Nature Reviews Immunology* 10(5), 301-316.

Chen, S. et al. (2010) "Surface hydration: Principles and applications toward low-fouling/nonfouling biomaterials," *Polymer* 51(23), 5283-5293.

Christoph, E. H. et al. (2010) "Targeting the Platelet Integrin GPIIb/IIIa," *Current Pharmaceutical Design* 16(37), 4119-4133.

Cines, D. B. et al. (2014) "Clot contraction: compression of erythrocytes into tightly packed polyhedra and redistribution of platelets and fibrin," *Blood* 123(10), 1596-1603.

Csomor, K. et al. (1994) "Effect of vintoperol on platelet aggregation and experimental thrombosis," *Arzneimittel-Forschung* 44(1), 36-40.

Danese, S. et al. (2003) "Activated platelets are the source of elevated levels of soluble CD40 ligand in the circulation of inflammatory bowel disease patients," *Gut* 52(10), 1435-1441.

Daoussis, D. et al. (2004) "Targeting CD40L: a Promising Therapeutic Approach," *Clinical and Diagnostic Laboratory Immunology* 11(4), 635-641.

Dela Paz, N. G. et al. (2009) "Arterial versus venous endothelial cells," *Cell and Tissue Research* 335(1), 5-16.

Duffau, P. et al. (2010) "Platelet CD154 Potentiates Interferon-α Secretion by Plasmacytoid Dendritic Cells in Systemic Lupus Erythematosus," *Science Translational Medicine* 2(47), 47ra63.

Elster, E. A. et al. (2001) "Treatment with the Humanized CD154-Specific Monoclonal Antibody, HU5C8, Prevents Acute Rejection of Primary Skin Allografts in Nonhuman Primates," *Transplantation* 72(9), 1473-1478.

FDA. Eptifibatide for Intravenous Administration, (FDA, Ed.).

Ferroni, P. et al. (2007) "Contribution of platelet-derived CD40 ligand to inflammation, thrombosis and neoangiogenesis," *Current Medicinal Chemistry* 14(20), 2170-2180.

Freedman, J. E. (2003) "CD40-CD40L and Platelet Function," *Circulation Research* 92(9), 944.

Henn, V. et al. (1998) "CD40 ligand on activated platelets triggers an inflammatory reaction of endothelial cells," *Nature* 391(6667), 591-594.

Huang, W. et al. (2002) "The effect of anti-CD40 ligand antibody on B cells in human systemic lupus erythematosus," *Arthritis & Rheumatism* 46(6), 1554-1562.

Huh, D. et al. (2013) "Microfabrication of human organs-on-chips," *Nature Protocols* 8(11), 2135-2157.

Huh, D. et al. (2012) "A Human Disease Model of Drug Toxicity-Induced Pulmonary Edema in a Lung-on-a-Chip Microdevice," *Science Translational Medicine* 4(159), 159ra147.

Huh, D. et al. (2010) "Reconstituting Organ-Level Lung Functions on a Chip," *Science* 328(5986), 1662.

Ingber, D. E. (2016) "Reverse Engineering Human Pathophysiology with Organs-on-Chips," *Cell* 164(6), 1105-1109.

Inoh, M. et al. (1996) "Evaluating systemic lupus erythematosus disease activity using molecular markers of hemostasis," *Arthritis & Rheumatism* 39(2), 287-291.

Jackson, S. P. (2007) "The growing complexity of platelet aggregation," *Blood* 109(12), 5087-5095.

Jain, A. et al. (2016) "Assessment of whole blood thrombosis in a microfluidic device lined by fixed human endothelium," *Biomedical Microdevices* 18(4), 73.

Jung, S. M. et al. (1998) "Platelets Interact with Soluble and Insoluble Collagens through Characteristically Different Reactions," *Journal of Biological Chemistry* 273(24), 14827-14837.

Kato, K. et al. (1999) "The soluble CD40 ligand sCD154 in systemic lupus erythematosus," *Journal of Clinical Investigation* 104(7), 947-955.

Kenyon, N. S. et al. (1999) "Long-term survival and function of intrahepatic islet allografts in rhesus monkeys treated with humanized anti-CD154," *Proceedings of the National Academy of Sciences* 96(14), 8132-8137.

Kimura, K. et al. (2005) "Study of plasma levels of soluble CD40 ligand in systemic lupus erythematosus patients who have undergone plasmapheresis," *Therapeutic Apheresis and Dialysis* 9(1), 64-68.

(56) References Cited

OTHER PUBLICATIONS

Kirk, A. D. et al. (1999) "Treatment with humanized monoclonal antibody against CD154 prevents acute renal allograft rejection in nonhuman primates," *Nature Medicine* 5(6), 686-693.

Koyama, I. et al. (2004) "Thrombophilia associated with anti-CD154 monoclonal antibody treatment and its prophylaxis in nonhuman primates," *Transplantation* 77(3), 460-462.

Kulkarni, S. et al. (2000) "A revised model of platelet aggregation," *Journal of Clinical Investigation* 105(6), 783-791.

Kuwana, M. et al. (2004) "Effect of a single injection of humanized anti-CD154 monoclonal antibody on the platelet-specific autoimmune response in patients with immune thrombocytopenic purpura," *Blood* 103(4), 1229.

Langer, F. et al. (2005) "The role of CD40 in CD4OL- and antibody-mediated platelet activation," *Thrombosis and Haemostasis* 93(6), 1137-1146.

Lehmann, M. et al. (2015) "On-chip recalcification of citrated whole blood using a microfluidic herringbone mixer," *Biomicrofluidics* 9(6), 064106.

Li, M. et al. (2014) "Microfluidic Thrombosis under Multiple Shear Rates and Antiplatelet Therapy Doses," *PLoS ONE* 9, e82493.

Liossis, S.-N. C. et al. (2004) "Costimulation Blockade in the Treatment of Rheumatic Diseases," *BioDrugs* 18(2), 95-102.

Meer, A. D. v. d. et al. (2012) "Organs-on-chips: breaking the in vitro impasse," *Integrative Biology* 4(5), 461-470.

Monroe, D. M. et al. (2002) "Platelets and Thrombin Generation," *Arteriosclerosis, Thrombosis, and Vascular Biology* 22(9), 1381.

Muthard, R. W. et al. (2014) "Rapid on-chip recalcification and drug dosing of citrated whole blood using microfluidic buffer sheath flow," *Biorheology* 51(2-3), 227-237.

Neeves, K. B. et al. (2013) "The use of microfluidics in hemostasis: clinical diagnostics and biomimetic models of vascular injury," *Current Opinion in Hematology* 20(5), 417-423.

Nishizawa, E. E. et al. (1972) "Collagen-induced pulmonary thromboembolism in mice," *Thrombosis Research* 1(3), 233-241.

Peters, A. L. et al. (2009) "CD40 and autoimmunity: The dark side of a great activator," *Seminars in Immunology* 21(5), 293-300.

Phillips, D. R. et al. (1997) "Clinical pharmacology of eptifibatide," *American Journal of Cardiology* 80(4A), 11B-20B.

Pierson, R. N., 3rd et al. (1999) "Prolongation of primate cardiac allograft survival by treatment with ANTI-CD40 ligand (CD154) antibody," *Transplantation* 68(11), 1800-1805.

Prasad, K. S. S. et al. (2003) "Soluble CD40 ligand induces β3 integrin tyrosine phosphorylation and triggers platelet activation by outside-in signaling," *Proceedings of the National Academy of Sciences* 100(21), 12367-12371.

Prasad, K. S. S. et al. (2003) "The platelet CD40L/GP IIb-IIIa axis in atherothrombotic disease," *Current Opinion in Hematology* 10(5), 356-361.

Robles-Carrillo, L. et al. (2010) "Anti-CD40L Immune Complexes Potently Activate Platelets In Vitro and Cause Thrombosis in FCGR2A Transgenic Mice," *Journal of Immunology* 185(3), 1577.

Roth, G. A. et al. (2004) "Thrombophilia Associated with Anti-CD154 Monoclonal Antibody Treatment and its Prophylaxis in Nonhuman Primates," *Transplantation* 78(8), 1238-1239.

Shock, A. et al. (2015) "CDP7657, an anti-CD40L antibody lacking an Fc domain, inhibits CD40L-dependent immune responses without thrombotic complications: an in vivo study," *Arthritis Research & Therapy* 17(1), 234.

Sidiropoulos, P. I. et al. (2004) "Lessons learned from anti-CD40L treatment in systemic lupus erythematosus patients," *Lupus* 13(5), 391-397.

Speiser, W. et al. (1990) "D-dimer and TAT measurement in patients with deep venous thrombosis: utility in diagnosis and judgement of anticoagulant treatment effectiveness," *Thrombosis and Haemostasis* 64(2), 196-201.

Tsai, M. et al. (2012) "In vitro modeling of the microvascular occlusion and thrombosis that occur in hematologic diseases using microfluidic technology," *Journal of Clinical Investigation* 122(1), 408-418.

Tutwiler, V. et al. (2017) "Interplay of Platelet Contractility and Elasticity of Fibrin/Erythrocytes in Blood Clot Retraction," *Biophysical Journal* 112(4), 714-723.

Vafa, O. et al. (2014) "An engineered Fc variant of an IgG eliminates all immune effector functions via structural perturbations," *Methods* 65(1), 114-126.

Wakefield, I. et al. (2010) "An Assessment of theThromboembolic Potential of CDP7657, a Monovalent Fab' PEG Anti-CD40L Antibody, in Rhesus Macaques," *Arthritis & Rheumatism* 62(Supplement 10), 1243.

Westein, E. et al. (2012) "Monitoring in vitro thrombus formation with novel microfluidic devices," *Platelets* 23(7), 501-509.

Westein, E. et al. (2013) "Atherosclerotic geometries exacerbate pathological thrombus formation poststenosis in a von Willebrand factor-dependent manner," *Proceedings of the National Academy of Sciences* 110(4), 1357-1362.

Xie, J. H. et al. (2014) "Engineering of a Novel Anti-CD40L Domain Antibody for Treatment of Autoimmune Diseases," *Journal of Immunology* 192(9), 4083.

Yau, J. W. et al. (2015) "Endothelial cell control of thrombosis," *BMC Cardiovascular Disorders* 15, 130.

Zhang, T. et al. (2015) "Update on CD40 and CD154 blockade in transplant models," *Immunotherapy* 7(8), 899-911.

\* cited by examiner

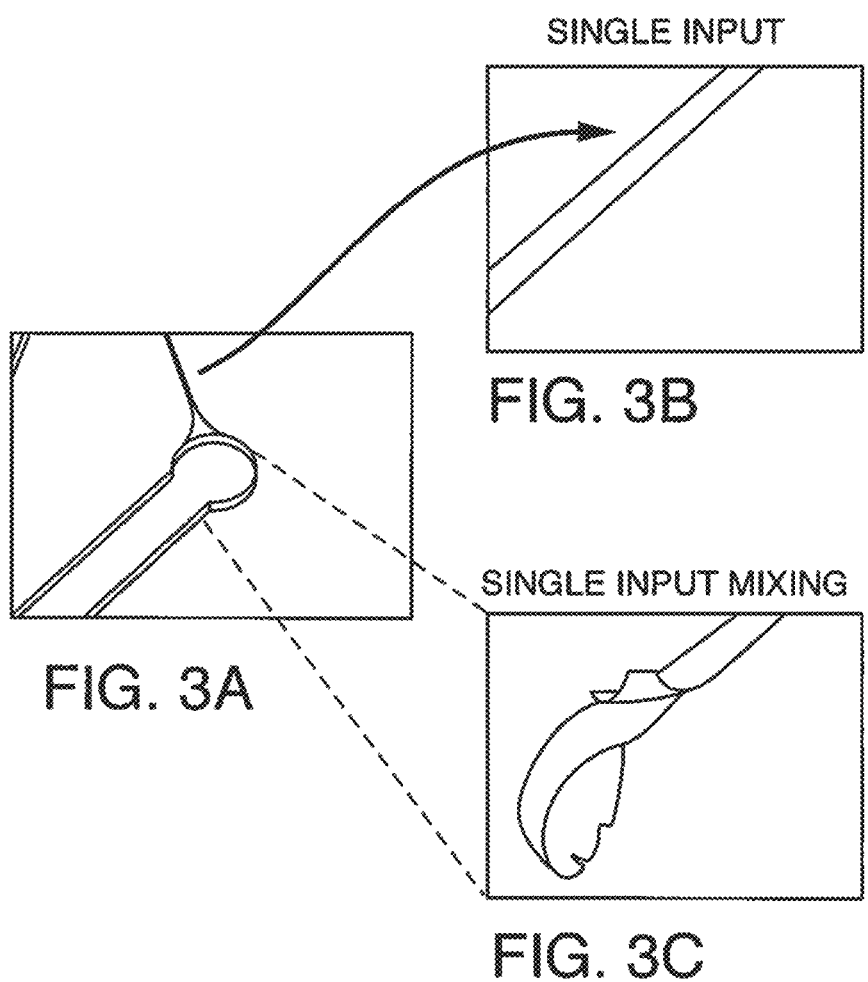

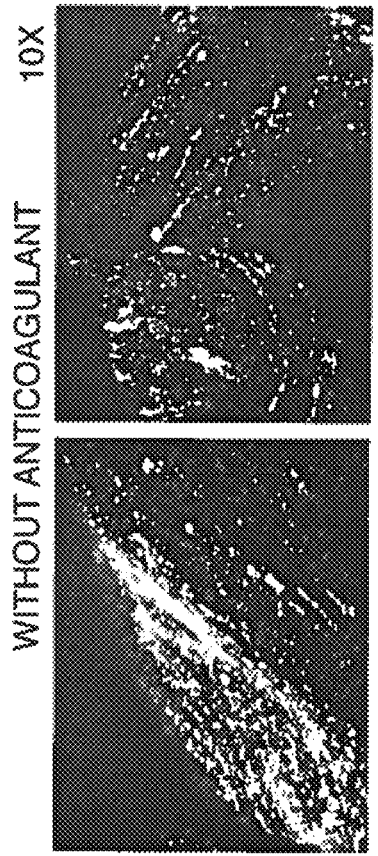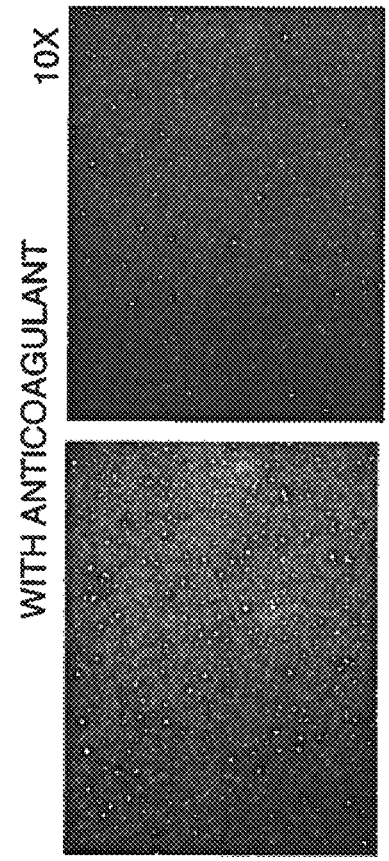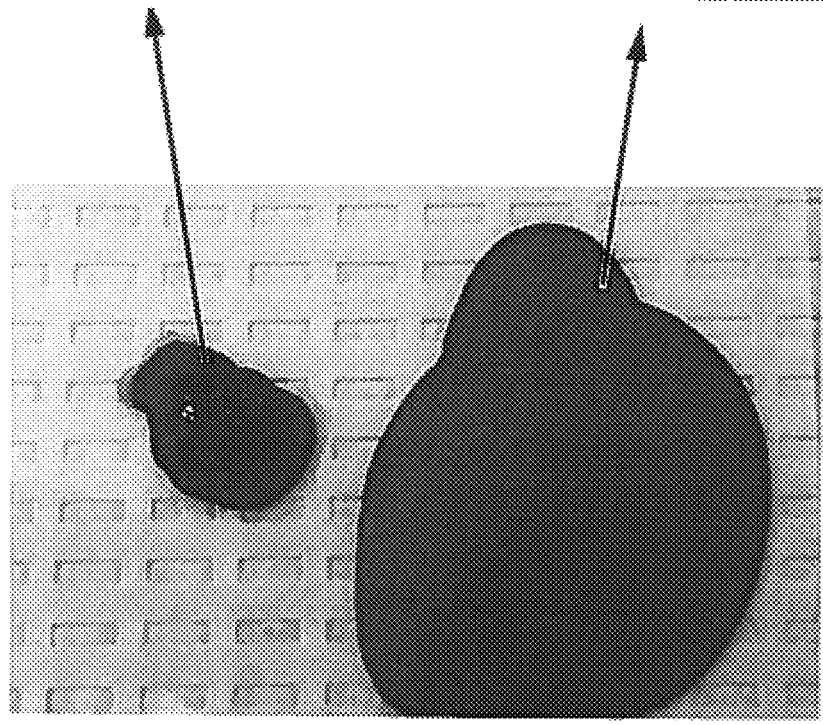
FIG. 6C
FIG. 6B
FIG. 6E
FIG. 6D
FIG. 6A
PLATELETS LABELED WITH CD41-TRITC ANTIBODY

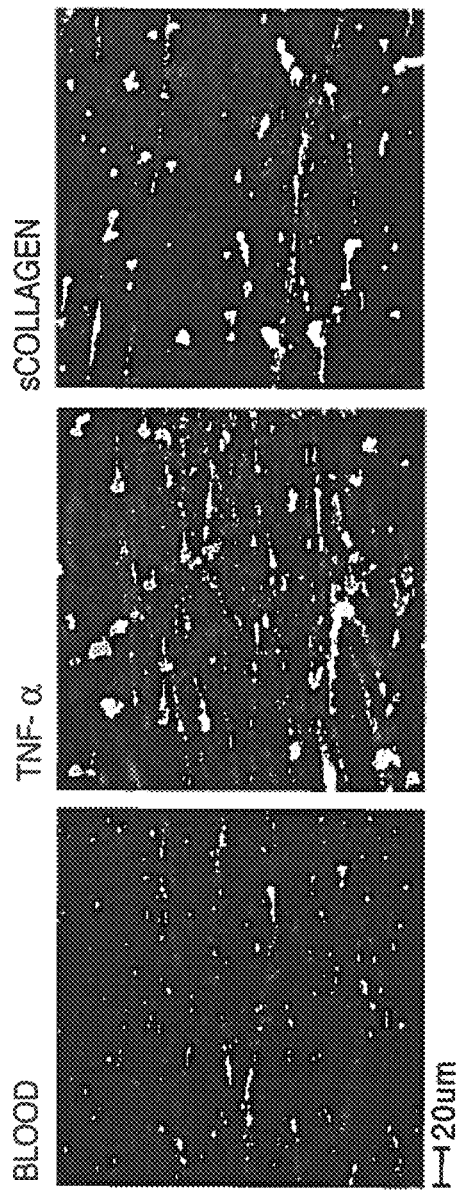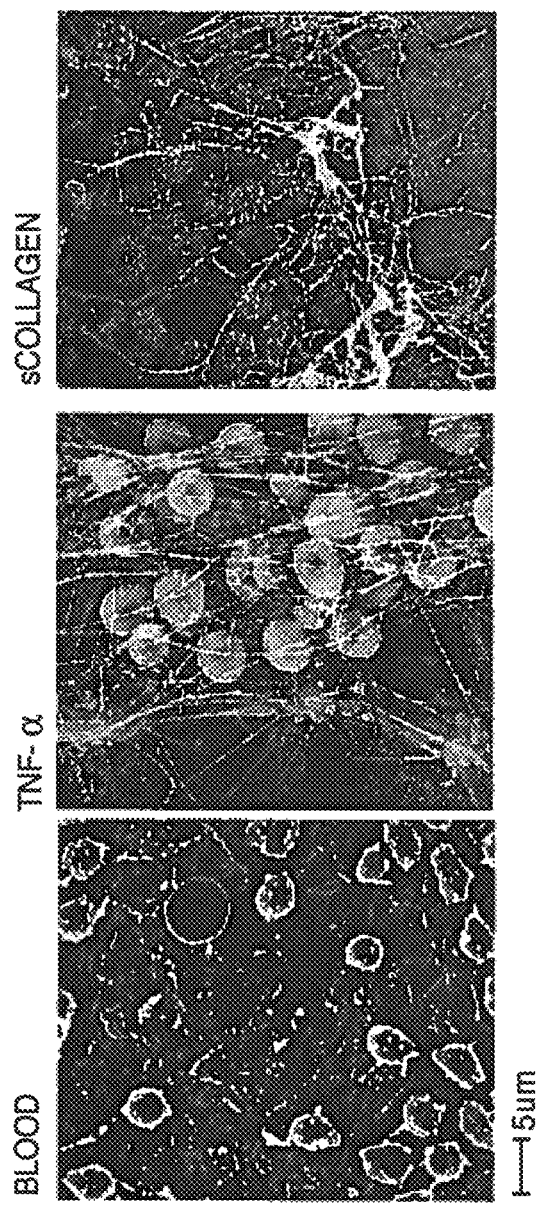

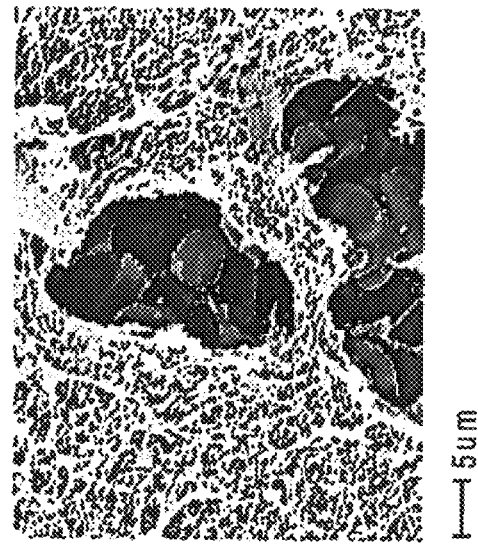
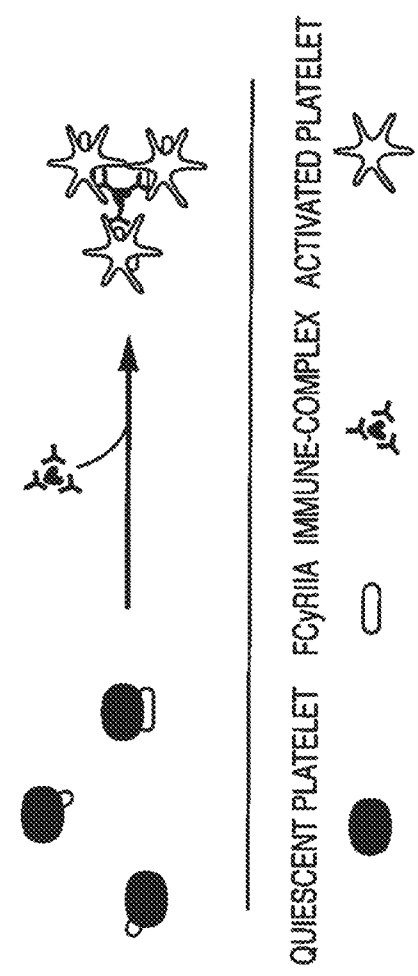
FIG. 21B
FIG. 21A

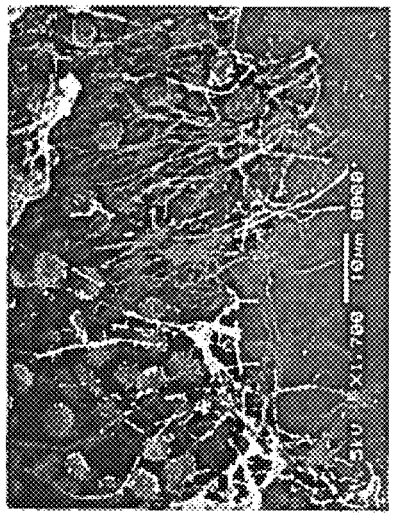
FIG. 28B SOLUBLE COLLAGEN
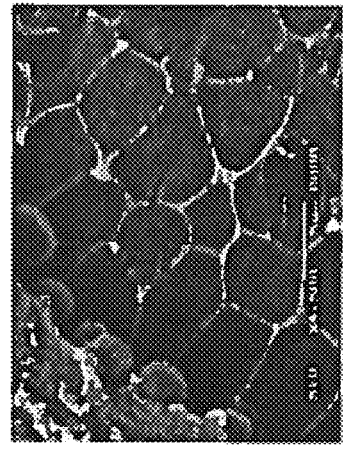
FIG. 28C
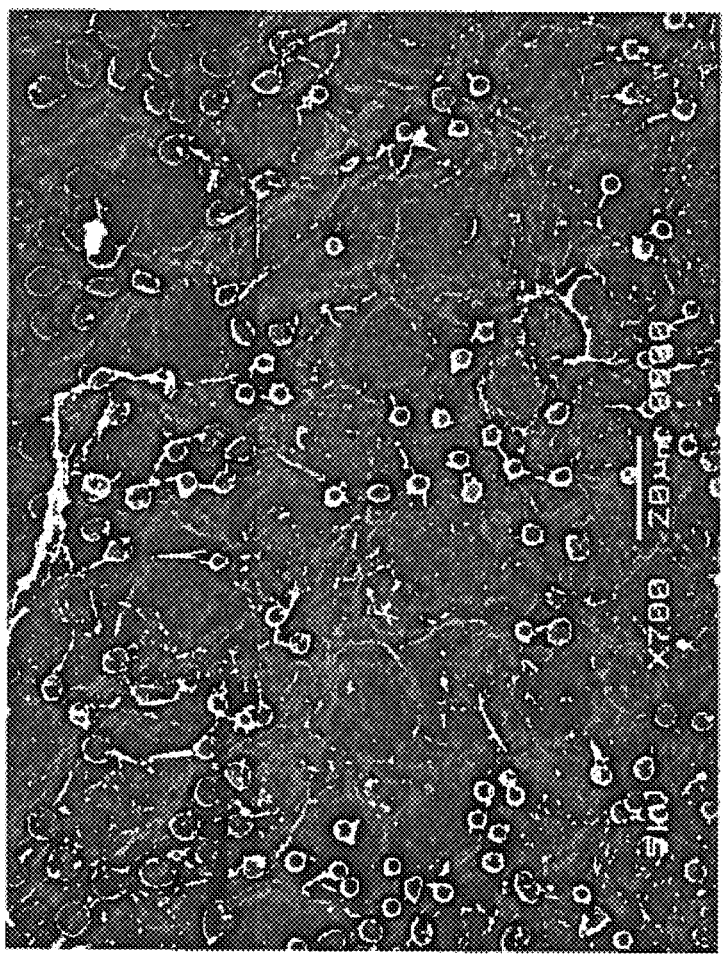
FIG. 28A CONTROL BLOOD

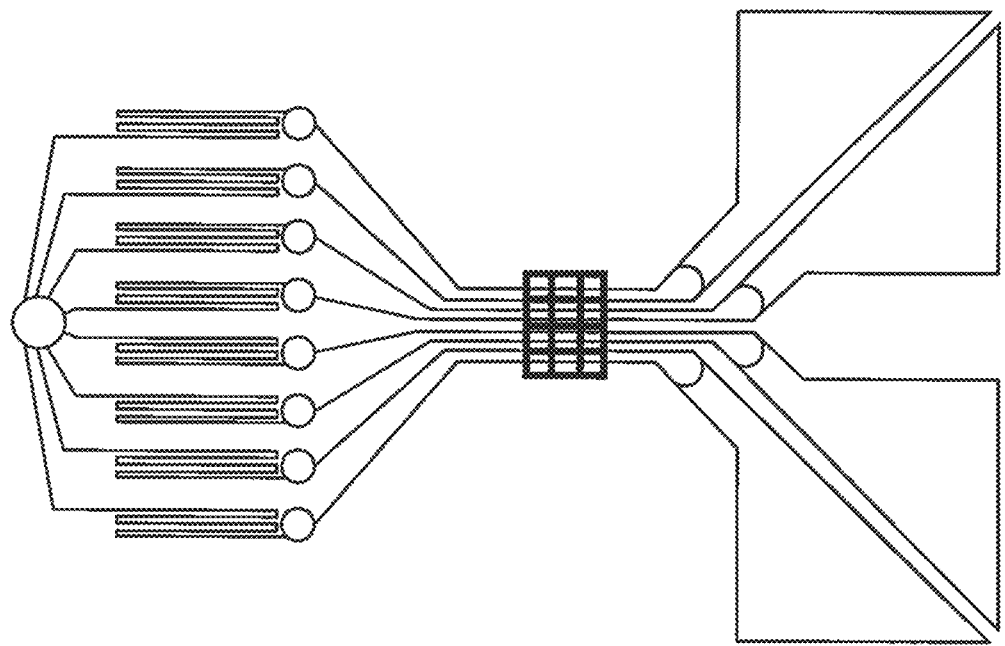
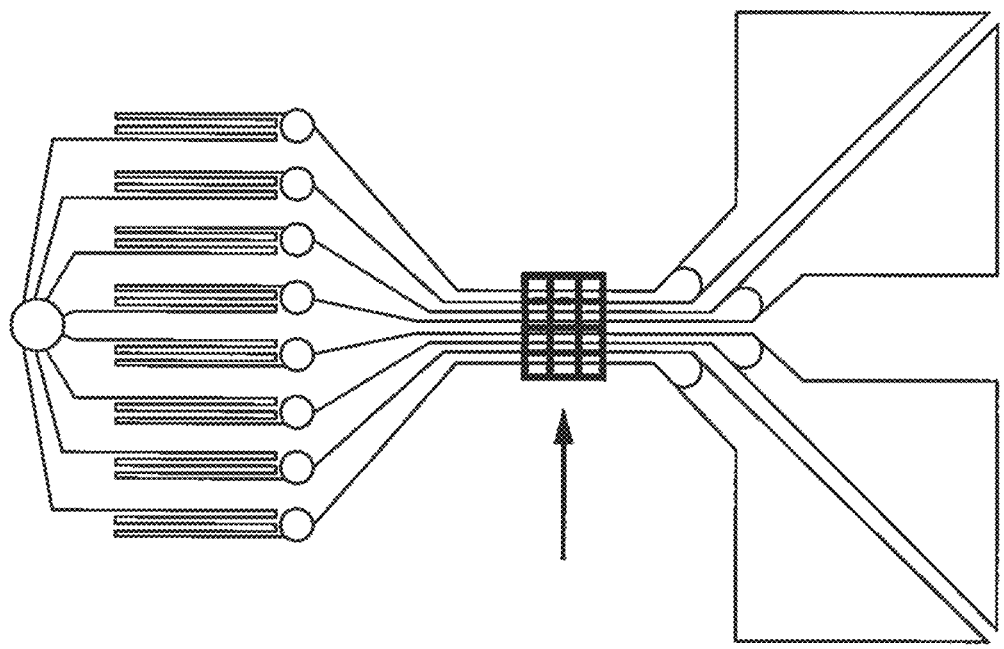
FIG. 38

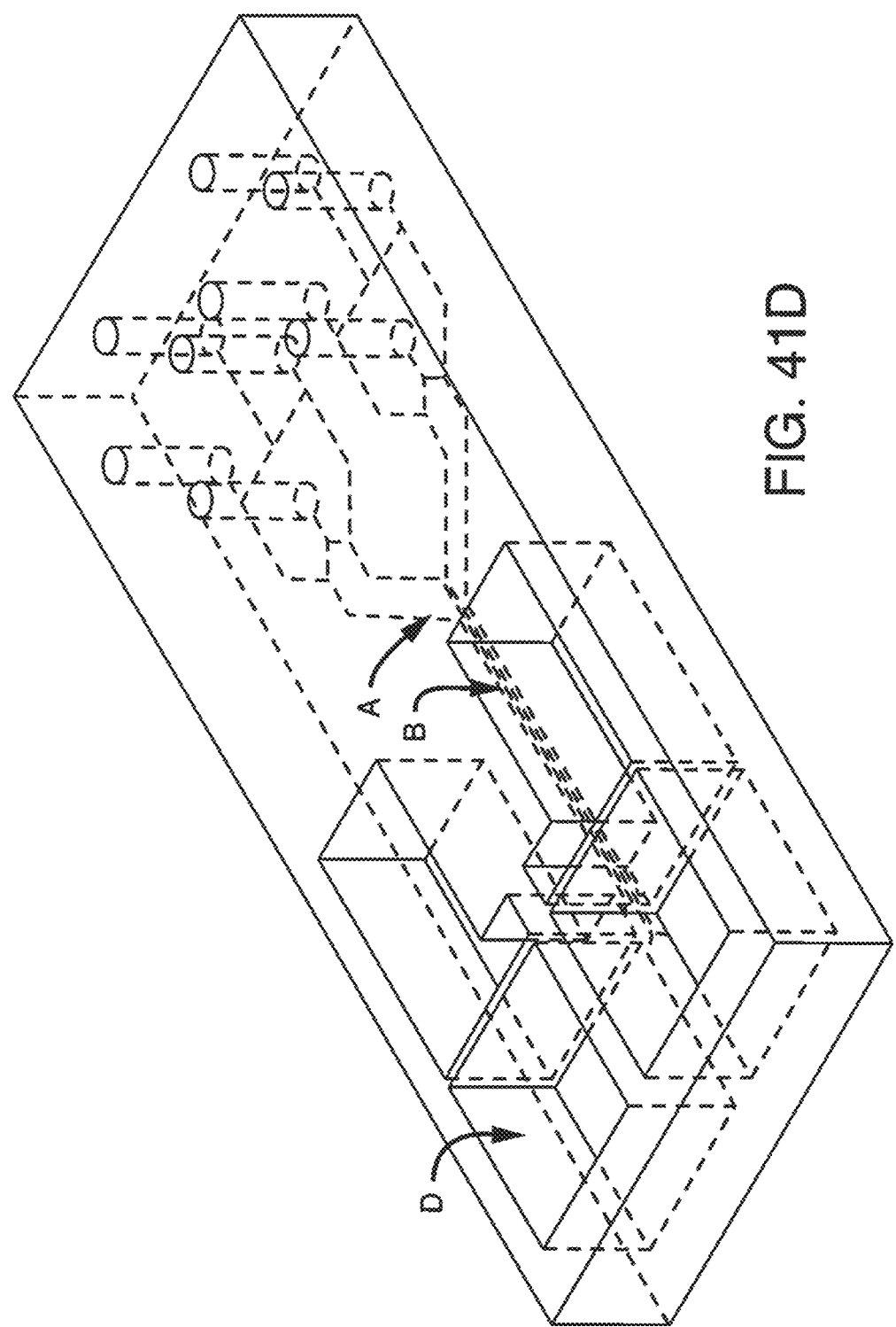

ADDITIVE CHANNELS

FIELD OF THE INVENTION

The present invention contemplates compositions, devices and methods of preventing, reducing, controlling or delaying adhesion, adsorption, surface-mediated clot formation, or coagulation in a microfluidic device or chip. In one embodiment, blood (or other fluid with blood components) that contains anticoagulant is introduced into a microfluidic device comprising one or more additive channels containing one or more reagents that will re-activate the native coagulation cascade in the blood that makes contact with it "on-chip" before moving into the experimental region of the chip.

BACKGROUND

Blood clotting, a process that relies on adhesion of platelets and proteins to a surface as a first step, can be a problem when blood is introduced into a microfluidic device. Undesired clot formation can make many desired blood tests impossible. Heparin coating of surfaces can control blood clotting to a limited extent. See Barstad, R. M, et al., *Thrombosis and Haemostasis* 79, 302-305 (1998). Certain polymeric species, such as polyethylene glycol (PEG) chains, can influence the surface hydration layer to prevent protein adsorption. See Chen, S. et al., *Polymer* 51, 5283-5293 (2010). However, they are not fully effective and soluble anticoagulants still must be added to the blood.

What is needed is better control over blood clotting in a microfluidic device.

SUMMARY OF THE INVENTION

The present invention contemplates compositions, devices and methods of preventing, reducing, controlling or delaying adhesion, adsorption, surface-mediated clot formation, or coagulation in a microfluidic device or chip. In one embodiment, blood (or other fluid with blood components) that contains anticoagulant is introduced into a microfluidic device comprising one or more additive channels containing one or more reagents that will re-activate the native coagulation cascade in the blood that makes contact with it "on-chip" before moving into the active or experimental region of the chip.

In one embodiment, fixatives are contemplated as additives for the additive channel (which can be useful for capturing the cells and platelets in their state immediately after contact with the cells in the chip). In one embodiment, oil is contemplated as an additive for the additive channel, to form blood-containing droplets (e.g. for sequestering blood samples from different time-points in the run, and analyzing them separately afterwards), etc. The addition of an additive channel near the outlet allows (in a versatile way) quick treatment of blood samples as they leave the chip. Such treated blood samples are contemplated to enable downstream analysis including but not limited to new types of analysis from the use of the additive channel for treating blood components as it leaves the chip.

Proposed mechanisms of hemostasis, platelet activation, and aggregation under arterial flow show that the dynamical cross-talk between the endothelium and platelets (as well as other cells such as leukocytes, microparticles, etc.) may cause blood cells to tether, detach, and translocate in space and time in vivo. Kulkarni, S. et al. "A revised model of platelet aggregation." *J. Clinical Investigation* 105(6), 783-791 (2000). Indeed, part of the reason why it has been difficult to assess platelet function accurately and reliably in vitro could be due to the fact that the existing tests do not incorporate a relevant shear stress environment or assess the contribution of endothelial function. Jackson, S. P. "The growing complexity of platelet aggregation." *Blood* 109 (12), 5087-5095 (2007).

Microfluidic devices (or "chips") containing living cells recreate the physiological tissue-tissue interfaces and permit fluid flow. See U.S. Pat. No. 8,647,861, hereby incorporated by reference. Such devices subject the cells to shear stress. In contrast to static 2D culture, microchannels allow the perfusion of cell culture medium throughout the cell culture during in vitro studies and as such offer a more in vivo-like physical environment. In simple terms, an inlet port allows injection of fluids such as blood, serum, plasma, cell culture medium (and the like) into a microfluidic channel or chamber (with or without cells). In one embodiment, the present invention contemplates a cell-laden microfluidic channel or chamber. An outlet port then permits the exit of remaining fluid as well as harmful metabolic by-products. Thus, microfluidic devices may be more reliable in vitro testing platforms for platelet analysis, including clot formation.

In one embodiment, the microfluidic device or chip is perfused by inserting it into a perfusion manifold or "pod." Perfusion manifolds of this type are described in U.S. patent application Ser. No. 15/248,509, hereby incorporated by reference.

While soluble anticoagulants prevent or at least reduce clot formation in a microfluidic device, they make the control over clot formation (when it is desired) difficult. The formation of aggregates and clots may result in contamination or blockage of the microchannels. One approach is to use off-chip mixing of blood with anticoagulants prior to contacting the chip with the blood. However, when on-chip coagulation is desired (or at least the possibility of coagulation is desired), this requires contact (and even mixing) with a reagent that re-activates the coagulation cascade (e.g. calcium).

Treating all of the blood (i.e. treating in bulk) with a reagent that re-activates the coagulation cascade prior to introducing the blood into the microfluidic device or chip is problematic. Microfluidic devices have slow flow rates. By the time the majority of the blood has entered the microfluidic device, if treated in bulk, it is likely to have coagulated. This would render the microchannel, if not the entire device, inoperable.

Another approach is to use on-chip contacting of blood (or other fluid with blood components) with one or more reagents that re-activate the coagulation cascade. Rather than treatment in bulk, only that fraction of the blood in contact with the reagent(s) that re-activate the coagulation cascade can clot. If this is done as the blood enters the active region, or immediately prior, clotting is only possible in the active region. This provides control over clotting.

With this said, on-chip mixing is complicated by dispersion of reagents along the microchannel, slow or incomplete mixing, and surface adsorption (due to the high surface area-to-volume ratio in microfluidic devices). To improve mixing, the present invention contemplates microfluidic devices with one or more additive channels. In one embodiment, blood (or other fluid with blood components) that contains anticoagulant is introduced into a microfluidic device (e.g. through an input port) comprising one or more additive channels (e.g. positioned at or near the input port) containing one or more reagents that will re-activate the native coagulation cascade in the portion of the blood that makes contact with it "on-chip" before moving into the active or experimental region of the chip.

While one additive channel can be used, it has been found empirically that two additive channels (one on either side of the input port or beginning of the microchannel) better control clotting. Without intending to limit the invention to any particular mechanism, it is believed that the reagents in solution coming in from both sides create a type of barrier on the side walls of the microchannel, inhibiting contact of the blood (or other input fluid) with the side walls. This inhibits clotting induced by contact with the walls of the microchannel. The blood (or other input fluid) travels down the microchannel to the "active" region, which may have cells (e.g. a monolayer of cells, such as endothelial cells). In this manner, clotting caused by the interaction of cells in the active region is distinguished from non-specific clotting induced by contact with the side walls of the microchannel.

In some embodiments, it may be desirable to further treat the blood (or other fluid with blood components) as it leaves the active region of the microchannel, or immediately thereafter, in order to reduce the chance of clotting after testing. In one embodiment, the present invention contemplates one or more additive channels (positioned near an output port) containing one or more reagents that will inactivate the native coagulation cascade in the blood that makes contact with it "on-chip" as it leaves the active or experimental region of the chip, permitting the blood to flow out the output port. While one additive channel can be used, it has been found empirically that two channels (one on either side of the output port or end of the microchannel) better control clotting.

Therefore, the present invention contemplates a method of adding reagent to a fluid sample in a microfluidic device, comprising: a) providing i) a fluid sample comprising anticoagulant, and ii) a microfluidic device comprising one or more additive channels in fluidic communication with at least one microchannel, said one or more additive channels comprising iii) a reagent solution comprising one or more reagents capable of re-activating the coagulation cascade, and; b) introducing said fluid sample into said microchannel of said microfluidic device under conditions such that a portion of said fluid sample contacts said reagent solution as said fluid sample moves through said microchannel. It is not intended that the present invention be limited to the type or nature of the fluid. In one embodiment, the fluid contains a component or cell associated with clotting. In one embodiment, said fluid sample comprises platelets. In one embodiment said fluid sample is blood (or a blood substitute). In one embodiment, said blood is human blood. It is not intended that the present invention be limited by the type or nature of the anticoagulant. In one embodiment, said anticoagulant is sodium citrate. In one embodiment, said anticoagulant is ethylenediamine tetraacetic acid (EDTA). In one embodiment, said anticoagulant was added to said human blood at the time it was collected from said human.

There are a variety of ways to introduce the fluid into the microchannel. In one embodiment, said microfluidic device comprises an input port in fluidic communication with said microchannel and said introducing of step b) is through said input port.

It is not intended that the present invention be limited by the number or positioning of the additive channels. In one embodiment, said one or more additive channels are positioned at or near said input port. In one embodiment, a first additive channel is positioned on one side of said microchannel near said input port. In one embodiment, a second additive channel is positioned on another side of said microchannel near said input port.

It is not intended that the present invention be limited to how it is used. However, in a preferred embodiment, said at least one microchannel comprises an active region comprising cells. In one embodiment, said cells are living cells. In one embodiment, said cells are fixed cells. In one embodiment, said cells comprise endothelial cells. In one embodiment, said endothelial cells are vascular endothelial cells. In one embodiment, said vascular endothelial cells are a monolayer. In one embodiment, said monolayer is disposed on a membrane. In one embodiment, said monolayer is attached to a cell adhesion promoting substance that coats the microchannel. In one embodiment, said cell adhesion promoting substance comprises one or more ECM proteins.

The present invention also contemplates, in one embodiment, a method of adding reagent to a fluid sample in a microfluidic device, comprising: a) providing i) a fluid sample comprising a first anticoagulant, and ii) a microfluidic device comprising one or more first additive channels in fluidic communication with a first end of a microchannel, said one or more first additive channels comprising iii) a first reagent solution comprising one or more reagents capable of re-activating the coagulation cascade, said microfluidic device further comprising one or more second additive channels in fluidic communication with a second end of a microchannel, said one or more second additive channels comprising iv) a second reagent solution comprising a second anticoagulant; b) introducing said fluid sample into said microchannel of said microfluidic device under conditions such that a portion of said fluid sample contacts said first reagent solution as said fluid sample moves through said microchannel so as to create a treated portion; and c) contacting said treated portion with said second reagent solution. It is not intended that the present invention be limited to the type or nature of the fluid. In one embodiment, the fluid contains a component or cell associated with clotting. In one embodiment, said fluid sample comprises platelets. In one embodiment said fluid sample is blood (or a blood substitute). In one embodiment, said blood is human blood. It is not intended that the present invention be limited by the type or nature of the anticoagulant. In one embodiment, said anticoagulant is sodium citrate. In one embodiment, said anticoagulant is ethylenediamine tetraacetic acid (EDTA). In one embodiment, said anticoagulant was added to said human blood at the time it was collected from said human.

There are a variety of ways to introduce the fluid into the device. In one embodiment, said microfluidic device comprises an input port in fluidic communication with said microchannel at said first end and said introducing of step b) is through said input port.

It is not intended that the present invention be limited by the number of positioning of the additive channels. In one embodiment, said one or more first additive channels are positioned at or near said input port. In one embodiment, one first additive channel is positioned on one side of said microchannel near said input port. In one embodiment, another first additive channel is positioned on another side of said microchannel near said input port.

A variety of different agents can be used. In one embodiment, said first reagent solution comprises calcium and magnesium. In one embodiment, said second reagent solution comprises ethylenediamine tetraacetic acid (EDTA). In an alternative embodiment, an aqueous solution can be used to prevent coagulation (e.g. diluting blood with a saline solution or a buffered solution to prevent coagulation).

It is not intended that the present invention be limited as to the use of the device. However, in a preferred embodiment, said at least one microchannel comprises an active region comprising cells. A variety of cell types are contemplated. In one embodiment, said cells are living cells. In one embodiment, said cells are fixed cells. In one embodiment, said cells comprise endothelial cells. In one embodiment, said endothelial cells are vascular endothelial cells. In one embodiment, said vascular endothelial cells are a monolayer. In one embodiment, said monolayer is disposed on a membrane. In one embodiment, said monolayer is attached to a cell adhesion promoting substance that coats the microchannel. In one embodiment, said cell adhesion promoting substance comprises one or more ECM proteins.

In a further embodiment, said microfluidic device comprises an output port in fluidic communication with said microchannel at said second end. In one embodiment, said one or more second additive channels are positioned at or near said output port. In one embodiment, one second additive channel is positioned on one side of said microchannel near said output port.

In one embodiment, another first additive channel is positioned on another side of said microchannel near said output port.

As noted above, the present invention contemplates methods, devices and systems. In one embodiment, the present invention contemplates a microfluidic device comprising i) a microchannel in fluidic communication with ii) an input port and iii) an output port, iv) one or more first additive channels in fluidic communication with at least one microchannel, positioned at or near said input port. It is not intended that the device be limited to the positioning or number of additive channels. In one embodiment, one first additive channel is positioned on one side of said microchannel near said input port. In one embodiment, another first additive channel is positioned on another side of said microchannel near said input port. In one embodiment, the device further comprises v) one or more second additive channels in fluidic communication with said microchannel, positioned at or near said output port. In one embodiment, one second additive channel is positioned on one side of said microchannel near said output port. In one embodiment, another second additive channel is positioned on another side of said microchannel near said output port.

It is not intended that the use of the device be restricted. However, in a preferred embodiment, said microchannel comprises an active region comprising cells (whether viable or fixed), including but not limited to human cells (e.g. liver cells, lung cells, etc.).

In one embodiment, the present invention contemplates a system, comprising: a) a fluid sample comprising anticoagulant, said fluid sample disposed in b) a microfluidic device comprising i) a microchannel in fluidic communication with ii) an input port and iii) an output port, iv) one or more first additive channels in fluidic communication with at least one microchannel, positioned at or near said input port, said first additive channels comprising a first reagent solution comprising one or more reagents capable of re-activating the coagulation cascade. In one embodiment, said microfluidic device further comprises v) one or more second additive channels in fluidic communication with said microchannel, positioned at or near said output port. In one embodiment, said fluid (whether blood, or merely containing some blood components) moves through the microchannel and come in contact with one or more additives via the fluidic communication of the microchannel with one or more additive channels.

In one embodiment, the present invention contemplates devices with input additive channels, output additive channels or both. In one embodiment, the present invention contemplates a microfluidic device, comprising: an input channel; an output channel; a test channel, wherein said test channel comprises an input portion in fluidic communication with said input channel and an output portion in fluidic communication with said output channel; (optionally) endothelial cells disposed within at least one portion of said test channel; and an input additive channel, wherein said input additive channel is in fluidic communication with said input portion of said test channel. In one embodiment said input channel and said input additive channel each have a fluidic resistance. It is not intended that, when cells are used in the device, that they be living. In one embodiment, said endothelial cells are living (e.g. viable) as measured by any technique (e.g. dye exclusion, biomarkers, secreted proteins, replication, etc.). In one embodiment, said endothelial cells are fixed. In one embodiment, said input additive channel is configured to deliver fluid to at least two opposing sides of said test channel (e.g. in a manner similar to that shown in FIG. 4A). In one embodiment, said input additive channel divides into two or more additive channel branches, wherein said two or more additive channel branches are configured to produce an approximately equal fluidic resistance (e.g. so that there is an approximately equal flow rate in said two or more additive channel branches). In one embodiment, the device further comprises an output additive channel in fluidic communication with said output portion of said test channel. It is not intended that the present invention be limited to the design of the microfluidic device. In one embodiment, the device further comprises a porous membrane and a back channel, wherein said membrane is situated between at least one portion of said test channel and at least one portion of said back channel (e.g. in a manner similar to that shown in FIG. 2). In one embodiment, at least one non-endothelial cell type is disposed within at least one portion of said back channel. In one embodiment, input channel further comprises a fluidic resistor (e.g. serpentine channels). In one embodiment, said input additive channel further comprises a fluidic resistor. In one embodiment, said output additive channel further comprises a fluidic resistor. In one embodiment, the device further comprises at least one reservoir. The reservoir can be for the input, the output, or any of the additive channels. In a preferred embodiment, reservoirs for input additive channel or output additive channels reagents are integrated on the microfluidic device ("on-chip"). In one embodiment, the device further comprises an input reservoir in fluidic communication with said input channel. In one embodiment, the device further comprises an input additive reservoir in fluidic communication with said input additive channel. In one embodiment, the device further comprises a pressure regulator, said pressure regulator adapted to apply a pressure to both the input reservoir and the input additive reservoir.

The present invention also contemplates in another embodiment, a microfluidic device, comprising: an input channel; an output channel; a test channel, wherein said test channel comprises an input portion in fluidic communication with said input channel and an output portion in fluidic communication with said output channel; (optionally) endothelial cells disposed within at least one portion of said test channel; and an output additive channel, wherein said output additive channel is in fluidic communication with said output portion of said test channel. Again, when used, the endothelial cells may be living or fixed. In one embodiment, said output additive channel is configured to deliver fluid to at least two opposing sides of said test channel (e.g. in a manner similar to that shown in FIG. 12). In one embodiment, said output additive channel divides into two or more additive channel branches, wherein said two or more additive channel branches are configured to produce an approximately equal fluidic resistance. In one embodiment, the device further comprises an input additive channel in fluidic communication with said input portion of said test channel. Again, it is not intended that the present invention be limited by the design of the microfluidic device. In one embodiment, the device further comprises a porous membrane and a back channel, wherein said membrane is situated between at least one portion of said test channel and at least one portion of said back channel. In one embodiment, at least one non-endothelial cell type is disposed within at least one portion of said back channel. In one embodiment, said input channel further comprises a fluidic resistor. In one embodiment, said output additive channel further comprises a fluidic resistor. In one embodiment, said input additive channel further comprises a fluidic resistor. In one embodiment, the device further comprises at least one reservoir. The reservoir can be for the input, the output, or any of the additive channels. In a preferred embodiment, reservoirs for input additive channel or output additive channels reagents are integrated on the microfluidic device ("on-chip"). In one embodiment, the device further comprises an input reservoir in fluidic communication with said input channel. In one embodiment, the device further comprises an output additive reservoir in fluidic communication with said output additive channel. In one embodiment, the device further comprises a pressure regulator, said pressure regulator adapted to apply a pressure to both the input reservoir and the output additive reservoir.

The present invention also contemplates methods of using additive channels. In one embodiment, the present invention contemplates a method of using a microfluidic device, comprising: a) providing, i) a microfluidic device, comprising: an input channel, an output channel, a test channel, wherein said test channel comprises an input portion in fluidic communication with said input channel and an output portion in fluidic communication with said output channel, (optionally) endothelial cells disposed within at least one portion of said test channel; and an input additive channel, wherein said input additive channel is in fluidic communication with said input portion of said test channel; ii) an anti-coagulated biological sample comprising cells, and iii) an agent that restores the coagulation abilities of said biological sample; b) flowing said anti-coagulated biological sample into said input channel and into said input portion of said test channel; and c) flowing said agent into said input additive channel under conditions such that agent contacts at least a portion of said anti-coagulated biological sample, wherein steps b) and c) can be performed in any order or simultaneously. In one embodiment, step b) is done before step c). In one embodiment step b) is done after step c). In one embodiment, steps b) and c) are performed simultaneously. The flow rates in steps b) and c) can be, but need not be, the same. In one embodiment, said flowing of step b) is done at first flow rate, and wherein said flowing of step c) is done at a second flow rate, wherein the first and second flow rates are proportional to each other. In one embodiment, the flow rate of step c) is a fraction (e.g. one quarter, one half, etc.) of the flow rate of step b). In one embodiment, the flow rates are chosen so that the amount of agent mixed in is sufficient to restore the coagulation abilities of said biological sample. In one embodiment, said contacting in step c) allows for a thrombotic process (e.g. such that another component or condition might initiate a thrombotic process). In one embodiment, the method further comprises d) optically observing said thrombotic process. It is not intended that the present invention be limited to the nature of the biological sample. In one embodiment, said biological sample comprises blood. In one embodiment, said biological sample comprises at least one blood component (e.g. platelets, red blood cells, white blood cells, etc.). In one embodiment, said agent that restores the coagulation abilities comprises calcium. In one embodiment, said optically observing comprises live-cell imaging. In one embodiment, said optically observing comprises live-cell imaging during said flowing of said biological sample. In one embodiment, the method further comprises a step of fixing said cells after step c). In one embodiment, the method further comprises a step of fixing said cells before step d). In one embodiment, at least a portion of said anti-coagulated biological sample flows out said output channel. In one embodiment, the method further comprises the step of collecting at least a portion of said sample from the output channel. In one embodiment, the method further comprises the step of analyzing said sample collected from said output channel. In one embodiment, said analyzing comprises testing for the existence of, or the amount of, components in said sample collected from said output channel. In one embodiment, said components are selected from the group consisting of cytokines, antibodies, blood cells, cell surface markers, proteins, RNA (including micro-RNA), DNA, biomarkers and clotting factors. In one embodiment, said device further comprises at least one output additive channel in fluidic communication with said output portion of said test channel. In one embodiment, the present invention contemplates the testing of drugs, candidate drugs or other compounds. In one embodiment, the method further comprises adding a test a compound to the agent before step c). In one embodiment, the method further comprises adding a test a compound to the biological sample before or during step b). In one embodiment, the test compound is evaluated for the potential to initiate, cause or otherwise enable a thrombotic process. For example, the test compound might be evaluated for the potential to promote on adhesion of platelets and/or proteins to a surface. On the other hand, the test compound might be evaluated for the potential to promote platelet activation and/or aggregation. In one embodiment, the test compound is evaluated for the potential to inhibit, block or otherwise interfere with a thrombotic process. For example, a test compound might be evaluated for the potential to inhibit adhesion of platelets and/or proteins to a surface. On the other hand, the test compound might be evaluated for the potential to inhibit platelet activation and/or aggregation. Still further, the test compound is evaluated for safety or efficacy. In one embodiment, the present invention contemplates comparing measures of thrombosis at different concentrations of the said test compound (including testing with and without the compound). In one embodiment, first and second test compounds are evaluated (e.g. for their ability to work together, work against one another, work synergistically, etc.). In one embodiment of a two compound method, a first compound is employed to induce coagulation and the second compound is employed in an attempt to stop it or at least inhibit it. In another embodiment of a two compound method, a first compound creates a disease model and a second compound is the one under investigation to treat the disease. Again, it is not intended that the present invention be limited only to specific microfluidic designs. In one embodiment, said microfluidic device further comprises a porous membrane and a back channel, wherein said membrane is situated between at least one portion of said test channel and at least one portion of said back channel. In one embodiment, at least one non-endothelial cell type is disposed within at least one portion of said back channel. In one embodiment, the method further comprises analyzing at least some of said cells of at least one non-endothelial cell type after step c). In one embodiment, the method further comprises d) flowing a third fluid into said back channel. In one embodiment, the method further comprises analyzing the outflow of said back channel.

In still another embodiment, the present invention contemplates a method of using a microfluidic device, comprising: a) providing i) a microfluidic device, comprising: an input channel, an output channel, a test channel, wherein said test channel comprises an input portion in fluidic communication with said input channel and an output portion in fluidic communication with said output channel, (optionally) endothelial cells disposed within at least one portion of said test channel; and an output additive channel, wherein said output additive channel is in fluidic communication with said output portion of said test channel; ii) a biological sample, and iii) an anti-coagulation agent, and b) flowing said biological sample into said input channel, into said input portion of said test channel, and into said output portion of said test channel; and c) flowing said agent into said output additive channel under conditions such that agent contacts at least a portion of said biological sample, wherein steps b) and c) can be performed in any order or simultaneously. In one embodiment, step b) is done before step c). In one embodiment step b) is done after step c). In one embodiment, steps b) and c) are performed simultaneously. The flow rates in steps b) and c) can be, but need not be, the same. In one embodiment, said flowing of step b) is done at first flow rate, and wherein said flowing of step c) is done at a second flow rate, wherein the first and second flow rates are proportional to each other. In one embodiment, the flow rate of step c) is a fraction (e.g. one quarter, one half, etc.) of the flow rate of step b). In one embodiment, the flow rates are chosen so that the amount of agent mixed in is sufficient to restore the coagulation abilities of said biological sample. In one embodiment, said output channel and said output additive channel each have a fluidic resistance. In one embodiment, the fluidic resistance of said output additive channel is adapted with respect to the fluidic resistance of said input channel (e.g. to be proportional to the input channel). In one embodiment, said contacting in step c) allows for a thrombotic process (e.g. such that another component or condition might initiate a thrombotic process). In one embodiment, the method further comprises d) optically observing said thrombotic process. In one embodiment, said biological sample comprises blood. In one embodiment, said biological sample comprises at least one blood component (e.g. platelets, red blood cells, white blood cells, etc.). In one embodiment, said agent is selected from the group consisting of EDTA, citrate, ACD, heparin and coumarin. In one embodiment, said optically observing comprises live-cell imaging. In one embodiment, said optically observing comprises live-cell imaging during said flowing of said biological sample. In one embodiment, the method further comprising a step of fixing said cells after step c). In one embodiment, the method further comprises a step of fixing said cells before step d). In one embodiment, at least a portion of said biological sample flows out said output channel. In one embodiment, the method further comprises the step of collecting at least a portion of said sample from the output channel. In one embodiment, the method further comprises the step of analyzing said sample collected from said output channel. In one embodiment, said analyzing comprises testing for the existence of, or the amount of, components in said sample collected from said output channel. In one embodiment, said components are selected from the group consisting of cytokines, antibodies, blood cells, cell surface markers, proteins, RNA (including micro-RNA), DNA, biomarkers and clotting factors. In one embodiment, said device further comprises at least one input additive channel. In one embodiment, the present invention contemplates the testing of drugs, candidate drugs or other compounds. In one embodiment, the method further comprises adding a test a compound to the agent before step c). In one embodiment, the method further comprises adding a test a compound to the biological sample before or during step b). In one embodiment, the test compound is evaluated for the potential to initiate, cause or otherwise enable a thrombotic process. For example, the test compound might be evaluated for the potential to promote the adhesion of platelets and/or proteins to a surface. On the other hand, the test compound might be evaluated for the potential to promote platelet activation and/or aggregation. In one embodiment, the test compound is evaluated for the potential to inhibit, block or otherwise interfere with a thrombotic process. For example, a test compound might be evaluated for the potential to inhibit adhesion of platelets and/or proteins to a surface. On the other hand, the test compound might be evaluated for the potential to inhibit platelet activation and/or aggregation. Still further, the test compound is evaluated for safety or efficacy. In one embodiment, the present invention contemplates comparing measures of thrombosis at different concentrations of the said test compound (including testing with and without the compound). In one embodiment, first and second test compounds are evaluated (e.g. for their ability to work together, work against one another, work synergistically, etc.). In one embodiment of a two compound method, a first compound is employed to induce coagulation and the second compound is employed in an attempt to stop it or at least inhibit it. In another embodiment of a two compound method, a first compound creates a disease model and a second compound is the one under investigation to treat the disease. Again, it is not intended that the present invention be limited only to specific microfluidic designs. In one embodiment, said microfluidic device further comprises a porous membrane and a back channel, wherein said membrane is situated between at least one portion of said test channel and at least one portion of said back channel. In one embodiment, at least one non-endothelial cell type is disposed within at least one portion of said back channel. In one embodiment, the method further comprises analyzing at least some of said cells of at least one non-endothelial cell type after step c). In one embodiment, the method further comprises d) flowing a third fluid into said back channel so as to create an outflow of said back channel. In one embodiment, the method further comprises analyzing the outflow of said back channel.

The present invention also contemplates systems comprising additive channels. In one embodiment, the present invention contemplates a system comprising: a) a microfluidic device comprising: an input channel; an output channel; a test channel, wherein said test channel comprises an input portion in fluidic communication with said input channel and an output portion in fluidic communication with said output channel; (optionally) endothelial cells disposed within at least one portion of said test channel; and an input additive channel, wherein said input additive channel is in fluidic communication with said input portion of said test channel; b) an input channel reservoir in fluidic communication with said input channel; c) an input additive channel reservoir in fluidic communication with said input additive channel; and d) a pressure source configured to apply pressure to both said input channel reservoir and said input additive channel reservoir. In one embodiment, said input additive channel is configured to provide a fluidic resistance that is proportional to the fluidic resistance of said input channel. In one embodiment, said input additive channel comprises a first fluidic resistor, and said input channel comprises a second fluidic resistor. In one embodiment, it is contemplated that the single pressure source can create the correct ratio of flow rates between the input channel and the additive channel. In a preferred embodiment, reservoirs are integrated on the microfluidic device ("on-chip").

In yet another embodiment, the present invention contemplates a system comprising: a) a microfluidic device comprising: an input channel; an output channel; a test channel, wherein said test channel comprises an input portion in fluidic communication with said input channel and an output portion in fluidic communication with said output channel; (optionally) endothelial cells disposed within at least one portion of said test channel; and an output additive channel, wherein said output additive channel is in fluidic communication with said output portion of said test channel; b) an input channel reservoir in fluidic communication with said input channel; c) an output additive channel reservoir in fluidic communication with said output additive channel; and d) a pressure source adapted to apply pressure to both said input channel reservoir and said output additive channel reservoir. In one embodiment, said output additive channel is configured to provide a fluidic resistance that is proportional to the fluidic resistance of said input channel. In one embodiment, said output additive channel comprises a first fluidic resistor, and input channel comprises a second fluidic resistor. In a preferred embodiment, reservoirs are integrated on the microfluidic device ("on-chip").

In yet another embodiment, the present invention contemplates a system, comprising i) a plurality of microfluidic devices (or simply microfluidic channels) sharing a single additive port between said plurality of said devices (or microfluidic channels), wherein said single additive port has a plurality of tubular branches, wherein each said branch is a fluidic connection with one device (or one channel), and wherein each said branch has an additive fluidic flow rate, and (optionally) ii) a plurality of fluidic flow resistors, wherein each branch has at least one resistor configured for controlling an additive fluidic flow rate.

In still another embodiment, the present invention contemplates a system comprising two (or more) constructs, each construct comprising: an input channel, an output channel, a test channel, wherein said test channel comprises an input portion in fluidic communication with said input channel and an output portion in fluidic communication with said output channel, (optionally) endothelial cells disposed within at least one portion of said test channel; an input additive channel, wherein said input additive channel is in fluidic communication with said input portion of said test channel, wherein the input additive channel of said first construct and the input additive channel of said second construct are fluidically coupled to a common additive channel. In one embodiment, the fluidic resistance of said input additive channel of first construct and said input additive channel of said second construct are adapted for approximately equal fluidic resistance. In one embodiment, the input additive channel of said first construct further comprises a first fluidic resistor, and wherein the input additive channel of said second construct further comprises a second fluidic resistor. In one embodiment, said constructs are microfluidic devices. In one embodiment, the system further comprises a cell-seeding channel, said cell-seeding channel fluidically coupled to said test channel of first construct and said test channel of second construct. In a method for using this system, the present invention contemplates an embodiment wherein the cell-seeding channel is used to seed both constructs (e.g. at once prior to an experiment).

In still another embodiment, the present invention contemplates a system comprising two (or more) constructs, each construct comprising: an input channel, an output channel, a test channel, wherein said test channel comprises an input portion in fluidic communication with said input channel and an output portion in fluidic communication with said output channel, (optionally) endothelial cells disposed within at least one portion of said test channel; an output additive channel, wherein said output additive channel is in fluidic communication with said output portion of said test channel, wherein the output additive channel of said first construct and the output additive channel of said second construct are fluidically coupled to a common additive channel. In one embodiment, the fluidic resistance of said output additive channel of first construct and said output additive channel of said second construct are adapted for approximately equal fluidic resistance. In one embodiment, the output additive channel of said first construct further comprises a first fluidic resistor, and wherein the output additive channel of said second construct further comprises a second fluidic resistor. In one embodiment, said constructs are microfluidic devices. In one embodiment, the system further comprises a cell-seeding channel, said cell-seeding channel fluidically coupled to said test channel of first construct and said test channel of second construct. In a method for using this system, the present invention contemplates an embodiment wherein the cell-seeding channel is used to seed both constructs (e.g. at once prior to an experiment).

The present invention contemplates in any of the above-described systems that the microfluidic devices (or plurality of microfluidic devices) or channels (or plurality of channels) comprise active regions within viewing range of a microscope. Alternatively, said microfluidic devices (or plurality of microfluidic devices) or channels (or plurality of channels) comprise active regions within a single field of view of a microscope image.

The present invention also contemplates a method comprising: a) providing: i) a microfluidic device comprising two or more test channels, wherein each said test channel comprises cells (e.g. endothelial cells); ii) at least one biological sample; and iii) a microscope; b) flowing said at least one biological sample into said two or more said test channels under conditions that initiate thrombus formation in at least one of said test channels; and c) imaging said test channels using said microscope. In one embodiment, step b) comprises flowing one of said at least one biological samples into two or more said test channels. For example, the same blood can be flowed into several channels, or alternatively, each channel can get its own blood sample. In one embodiment, said at least one test channel of said microfluidic device further comprises: an input channel and an input portion of said test channel, wherein said input portion is in fluidic communication with said input channel, and an input additive channel, wherein said input additive channel is in fluidic communication with said input portion of said test channel. In one embodiment, said at least one test channel of said microfluidic device further comprises: an output channel and an output portion of said test channel, wherein said input portion is in fluidic communication with said output channel, and an output additive channel, wherein said input additive channel is in fluidic communication with said output portion of said test channel. In one embodiment, said imaging of step c) comprises imaging at least a portion of each test channel of said microfluidic device in a single microscope field. In one embodiment, said microscope further comprises a microscope stage, and wherein imaging of step c) comprises imaging at least a portion of each test channel of said microfluidic device by means of motion of said microscope stage.

The present invention also contemplates in one embodiment a microfluidic device comprising a test channel, and endothelial cells disposed within at least a portion of said test channel, wherein said test channel includes at least one geometrical feature selected from the list consisting of a gradual change of cross-section, an abrupt change of cross-section, a bend, a bifurcation. In one embodiment, the microfluidic device further comprises an input channel, an input portion of said test channel, wherein said input portion is in fluidic communication with said input channel, and an input additive channel, wherein said input additive channel is in fluidic communication with said input portion of said test channel. In one embodiment, said at least one test channel of said microfluidic device further comprises: an output channel, an output portion of said test channel, wherein said input portion is in fluidic communication with said output channel, and an output additive channel, wherein said input additive channel is in fluidic communication with said output portion of said test channel.

Definitions

Anticoagulants are used to prevent clot formation both in vitro and in vivo. In the specific field of in vitro diagnostics, anticoagulants are commonly added to collection tubes either to maintain blood in the fluid state for hematological testing or to obtain suitable plasma for coagulation and clinical chemistry analyses.

Calcium is necessary for a wide range of enzyme reactions of the coagulation cascade and its removal prevents blood clotting within the collection tube. Ethylenediamine tetraacetic acid (EDTA) is a polyprotic acid containing four carboxylic acid groups and two amine groups with lone-pair electrons that chelate calcium and several other metal ions. Historically, EDTA has been recommended as the anticoagulant of choice for hematological testing because it allows the best preservation of cellular components and morphology of blood cells. The remarkable expansion in laboratory test volume and complexity over recent decades has amplified the potential spectrum of applications for this anticoagulant, which can be used to stabilize blood for a variety of traditional and innovative tests.

One can also anti-coagulate blood with sodium citrate (e.g. 3.2%). EDTA and sodium citrate are both calcium chelators. Without wishing to be bound by theory, platelet function may depend upon the presence of $Ca^{2+}$ and $Mg^{2+}$. Thus, for a fluid sample comprising a citrated blood sample (where citration of a blood sample generally quenches the free $Ca^{2+}$ and $Mg^{2+}$ ions to prevent blood coagulation), addition of $Ca^{2+}$ (e.g., calcium chloride) and $Mg^{2+}$ (magnesium chloride) to the fluid sample can help restore the native physiological state of the platelet, e.g., to allow platelet aggregation or coagulation. Thus, in some embodiments, the citrated blood sample can be added with $Ca^{2+}$ (e.g., calcium chloride) and $Mg^{2+}$ (magnesium chloride) such that the final concentrations reach about 4-12 mM and 3-10 mM, respectively.

In an alternative embodiment, an aqueous solution can be used to prevent coagulation (e.g. diluting blood with a saline solution or a buffered solution to prevent coagulation).

In one embodiment, blood (or other fluid sample with blood components) is introduced into the microfluidic device comprising on or more channels, and more specifically, one or more microchannels. The surface over which the sample flows to perform the cell analysis using the methods described herein can be a surface of any material that is compatible to the fluid sample and cells. Exemplary materials for the fluid-contact surface can comprise glass, synthetic polymers (e.g., PDMS, polysulfonate, and polycarbonate), hydrogels, and a combination thereof.

"Channels" are pathways (whether straight, curved, single, multiple, in a network, etc.) through a medium (e.g., silicon, glass, polymer, etc.) that allow for movement of liquids and gasses. In some embodiments, described herein "test channel" are used and these need not have the same shape throughout their length. For example, one can change the channel cross-section (expansions and contractions), one can bend the channel (including a spiral version), and/or one can bifurcate the channel (include the corner areas). Channels can connect or be coupled with other components, i.e., keep components "in communication" and more particularly, "in fluidic communication" and still more particularly, "in liquid communication." Such components include, but are not limited to, liquid-intake ports and gas vents. Channels can also permit on-chip mixing of cells with reagents, such as reagents that re-activate the coagulation cascade and anticoagulants. Microchannels are channels with dimensions less than 1 millimeter and greater than 1 micron. It is not intended that the present invention be limited to only certain microchannel geometries. In one embodiment, a four-sided microchannel is contemplated. In another embodiment, the microchannel is circular (in the manner of a tube) with curved walls. In yet another embodiment, combination of circular or straight walls are used.

One portion of a microchannel can be a membrane. For example, the floor of a microchannel can comprise a membrane, including a porous membrane. The microchannel (or portion thereof) or membrane can be coated with substances such as various cell adhesion promoting substances or ECM proteins, such as fibronectin, laminin or various collagen types or combinations thereof. For example, endothelial cells can attach to a collagen coated microchannel.

It is not intended that the present invention be limited by the number or nature of channels in the microfluidic device. In some embodiments, the surface can be a surface of a fluid-flowing conduit or passageway disposed in a solid substrate. In some embodiments, the surface can be a solid surface. For example, in one embodiment, the solid surface can be a wall surface of a fluid channel, e.g., a microfluidic channel.

Additionally, the term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

In some embodiments, fluids comprising platelets are introduced into the microfluidic device in order to detect platelet function or dysfunction. As used herein, the term "platelet dysfunction" refers to abnormal platelet behavior, as compared to healthy platelets. In one embodiment, platelet dysfunction can be caused by increased adhesion to an endothelium (e.g., by at least about 30% or more), as compared to healthy platelets. In one embodiment, platelet dysfunction can be caused by abnormal detachment from other platelets and/or from an endothelium (e.g., by at least about 30% or more), as compared to healthy platelets. In one embodiment, platelet dysfunction can be caused by abnormal translocation (e.g., by at least about 30% or more), as compared to healthy platelets. As used herein, the term "abnormal translocation" refers to a platelet that gets activated in one location and deposits at another location to form a clot or cause inflammation response. For example, thromboembolism can be considered as abnormal translocation. In one embodiment, platelet dysfunction can be caused by increased aggregation between platelets (e.g., by at least about 30% or more), as compared to healthy platelets.

BRIEF DESCRIPTION OF THE DRAWINGS

FIGS. 3A-C shows one embodiment of on-chip mixing using a single input, i.e. a single additive channel in fluidic communication. FIG. 3A shows the input channel attached to the microfluidic port of the microfluidic device. FIGS. 3B and 3C are photographs showing the single input stream and single input mixing, respectively.

FIG. 4A shows a schematic of the dual input additive channels attached to the microfluidic port of the microfluidic device. FIG. 4B and FIG. 4C are photographs showing the dual input streams and dual input mixing, respectively.

FIG. 5A shows tubing connecting a source of sodium citrate to the microfluidic device (not shown). On-chip mixing with sodium citrate (arrow) allows samples to flow freely, while lack of anticoagulant input clogs collection tubes and can slow or completely stop flow. FIG. 5B shows five tubes, four of which were treated on-chip with anticoagulant and can be analyzed. Tube 5 was not treated and contains a solid mass of coagulated blood, which cannot be used for testing.

FIGS. 6A-E shows exemplary illustrations of photographs of blood sampled from the outlet of standard chips (without anticoagulant) compared to anticoagulant added to disclosed chips through anticoagulant ports. Droplets of blood sampled from the effluents at the end of a 15-minute experiment were absorbed on sterile paper then deposited on glass-slide for further fluorescent microscopy imaging. Two representative images are shown here for each treatment. Platelets were labeled with CD41-TRITC antibody. FIG. 6A is a photograph of blood sampled from the effluents (i.e. outlet) of standard chips without anticoagulant (bottom image) or from the effluents of the disclosed chips equipped with the anticoagulant port and with anticoagulant (top image). FIG. 6B and FIG. 6C are photographic images showing fluorescently-labeled platelet aggregates, demonstrating clotting in the untreated sample. Magnification ×10. FIG. 6D and FIG. 6E are photographic images for the treated sample, with labeled platelets from the treated sample that are dispersed in the blood liquid phase, demonstrating an uncoagulated state. Magnification ×10.

FIGS. 18A1-A2 through FIG. 18E-1 and FIG. 18E-2 demonstrates one embodiment of an On-chip reconstitution of thrombosis showing schematic illustrations of an exemplary embodiment for a microfluidic-chip, micrographs of cells and charts comparing blood clotting events induced by several compounds. FIG. 18A-1 is a schematic representation of one embodiment of a Thrombosis-On-Chip (200). FIG. 18A-2 is a schematic representation of the chip (200) showing the main features: inlet port (1810), main channel and imaged area (1820), outlet port (1815), and the on-chip anticoagulant port. FIG. 18B Top shows endothelial morphology by fluorescent VE-cadherin staining (stain as white lines). FIG. 18B Bottom shows a high magnification section of endothelial cells stained for VE-cadherin. FIG. 18C shows that under control conditions (whole blood alone) platelets and fibrin shown as white spots and line, are sparse and detectable at the edge of the imaged areas. Endothelial exposure to TNF-α or pre-incubation of blood with soluble collagen (sCollagen) led to formation of a high number of larger aggregates containing a platelet rich core decorated with fibrin. FIG. 18D shows scanning electron micrographs of cells showing typical ultrastructure of blood clots formed on-chip, in control conditions ('Blood') the sparse platelets are dispersed on an endothelial surface, in stimulated conditions ('TNF-α' and 'sCollagen') activated platelet aggregates and fibrin networks with trapped red blood cells are attached to an endothelial cell surface. FIG. 18E-1 shows platelet coverage and FIG. 18E-2 shows fibrin deposition (both charts using the lower treatment key shown in FIG. 18E-2) that were significantly increased in stimulated platelet coverage; fibrin deposition were significantly increased in stimulated, pro-thrombotic conditions in multiple donors (n=4, S.E.M., * p<0.05, ns=not significant), and the effects were suppressed by adding the drug Eptifibatide. Overall, there is a highly significant difference between the TNF-alpha treatment with and without Eptifibatide and between sCollogen treatment with and without Eptifibatide.

FIG. 19A Left, schematic illustration of a cross-section of one embodiment of a chip with an anticoagulant port used to monitor endothelial integrity. Right, endothelial cells covering the entire surface of the vascular compartment were monitored via light microscopy imaging for 6 days. FIG. 19B shows tissue integrity was monitored via a vascular leakage assay using fluorescent dextrin (3 Kda). FIG. 19C shows a schematic of one embodiment of a chip 1900 with an anticoagulant port attached to the top microfluidic channel where the upper channel is also marked with an OUTLET at one end. In other embodiments, such as described in FIG. 19A, the lower vascular chamber has an anticoagulant port near the vascular outlet, shown in FIG. 14 and FIG. 15. FIG. 19C has arrows pointing to INLET ports 1910 and 1911. The upper channel 1912 emerges from one INLET 1910. The lower channel 1914 emerges from underneath the upper channel attached to the lower Inlet 1911. Arrows point to OUTLET ports 1915 and 1917. An arrow points to the IMAGING area (active region) 1920 outlined with dotted lines. An arrow points to the ANTICOAGULANT port 1930. There are also arrows pointing to an additive channel 1932 and 1934 surrounding the OUTLET port 1917. FIG. 19D shows representative images obtained from the central area of the vascular chamber after blood perfusion (15 mins). The effects of the platelet inhibitor Eptifibatide are clearly visible in both conditions.

FIG. 20A shows immunostaining of healthy endothelium. ICAM1 is shown with examples identified by white arrows. One example of a DAPI stained nuclei is shown inside of a white circle. FIG. 20B shows immunostaining of healthy endothelium stimulated with TNF-α showing higher numbers of cells identified by costaining with ICAM and DAPI (arrows).

FIGS. 21A-E show exemplary schematic illustrations, micrographs and charts showing the combination of hu5c8 and sCD40L immune-complex ($IC_{5c8}$) induced thrombosis on-chip. FIG. 21A shows a schematic overview of an embodiment showing how hu5c8 and sCD40L form immune complexes that in turn can activate platelets by engaging with the Fcγ receptors on their surface. FIG. 21B shows a colored micrograph of immunostained cells showing blood samples treated with combined hu5C8/sCD40L promotes formation of sparse microthrombi (blood clots) rich in fibrin, platelets (large round circles) and fibrin (fibers). FIG. 21C shows that combined Hu5C8/sCD40L promotes formation of blood clots constituted by small platelet aggregates and fibrin. FIG. 21D shows platelet coverage measured on-chip after 12 minutes of continuous blood perfusion in presence of sCD40L, hu5c8 or combined hu5C8/sCD40L and normalized in respect to blood alone (n=4, bars indicate SEM, p value calculated using one-way ANOVA, ns: not significant). FIG. 21E shows gene expression data obtained from chips treated with blood alone or in combination with sCD40L and hu5c8 and normalized in respect to cells perfused with standard cell culture medium.

FIG. 22A, a citrate solution (from additive channels 2007 and 2008) is actively pushed into the outflow stream (2010) of blood as it leaves the Vessel-On-Chip. This prevents clotting inside connectors and tubing, allowing for longer experiments as well as conventional analysis of the out flowing blood samples. FIG. 22B, Thrombin Anti-Thrombin (TAT) levels are analyzed in plasma from blood flowing out of the vessel-on-chip device. TNF-α pre-treatment of the endothelium, as well as sCollagen, or a combination of sCD40L and hu5c8 dosing in the blood before perfusion, leads to elevated levels of TAT in the outflow samples as measured by ELIZA.

FIG. 25A Schematic representations of embodiments showing how antibodies with different structures contribute and interfere with the interaction of platelets with immune complexes. By using antibodies with modified Fc regions (IgGσ, middle), or by using anti-Fcγ Receptor blocking antibodies (IV.3, right), immune complex interaction with platelets should be prevented. Key: large round circles represent quiescent platelets, hearts represent sCD40L, Y represents Hu5c8, rounded narrow rectangles represent FCgRIIA, stars represent activated platelets, and a heart surrounded by Y's represents immune-complexes. Immune complexes (IC) formed with hu5C8, but not with other treatments, and incubated in blood in the absence of blocking antibodies induced platelet adhesion FIG. 25B; FIG. 25C fibrin formation; and FIG. 25D TAT release on-chip. (n=15; n=5; n=7, respectively).

FIG. 26A shows platelet coverage, as fold increment increases in respect to untreated blood; FIG. 26B shows fibrin fluorescence, as fold increment increases in respect to untreated blood; and FIG. 26C shows changes in TAT levels (ng/ml (ELIZA).

FIG. 27A shows an exemplary chart showing platelet coverage over time (minutes) up to at least 12 minutes, comparing control blood to sCD40L, Hu5c8 and IC; FIG. 27B shows an exemplary chart demonstrating fold increment increases, in respect to untreated blood, for the treatments shown in FIG. 27A; FIG. 27C shows a colored immunofluorescent micrograph of blood clots in microfluidic channels; FIG. 27D and FIG. 27E shows scanning electron micrographs (SEM): FIG. 27D shows unclotted blood and FIG. 27E shows clotted blood in the left panel vs. unclotted blood in the right panel.

FIGS. 28A-C show comparative scanning electron micrographs of FIG. 28A control blood; FIG. 28B blood in the presence of soluble collagen and FIG. 28C blood treated with IC (immune complexes).

FIG. 30A shows one embodiment of a schematic top view of a four channel chip having four exemplary pre-set microchannel geometries with the same Outflow rate, e.g. having a 100 um Outflow, also shown in FIG. 30B and FIG. 30C (bottom view), FIG. 30B shows a schematic bottom view diagram of an exemplary 4 channel microfluidic device. FIG. 30C shows one embodiment of a schematic 3-D angular view of a 4 channel microfluidic device contemplated for use as a mold for fabricating chips shown in FIG. 30A and FIG. 30B.

FIG. 31A shows an outline representing one field of view (FOV) on a microscope stage, when viewed using a 10× ocular, e.g. a 1350 um by 1350 um area, i.e. one Tile Area as viewed with an Olympus Light Microscope. FIG. 31B shows an exemplary representation of the total viewing area (e.g. as determined by the range of motion of the stage controls) where the total viewing area includes but is not limited to 12 Tile Areas, e.g. 12 quadrants, for a total view area 5.4 mm wide and 4.05 mm in length, wherein each Tile Area or quadrant representing one FOV. In one embodiment, twelve (12) tiles are contemplated for viewing in under a 30 sec frame rate limit (1 frame every 30 seconds) for photography, including but not limited to videophotography, of events occurring within at least one active region in a microchannel.

FIG. 32A shows an exemplary 3D view of one embodiment of a microfluidic device, wherein four lower indentations represent molded on chip reservoirs. Upper circles represent exemplary inlet/outlet ports. FIG. 32B shows the four channels having exemplary dimensions of 100 um diameter channels spaced 50 um apart for providing a total 550 um wide region such that parallel locations within the active regions in all four channels may be viewed under a microscope within a microscopic field of view. In one embodiment, so that the channels fit under one field, one can design them as 100 um×100 um. FIG. 32C shows an exemplary microfluidic device dimension of 46 mm long and 18 mm wide, and the dotted lines represent the parallel active regions in the channels as shown in FIG. 32B.

FIG. 35A shows an exemplary schematic diagram of a device during cell seeding, where positive pressure, shown by the thick arrows pointing down representing the direction of fluid flow, is used to seed cells into channels, where cells are seeded into the multi-inlets while the other ports, 1, 2, 3, 4 and EDTA input are plugged (black circles), followed by cell attachment to the microchannels. Afterwards, medium is pushed through to rinse channels, see arrowheads in channels/branches between ports and the microchannels. FIG. 35B shows an exemplary schematic diagram of fluid flow in a device during cell feeding. Medium is added to reservoirs, using 200 ul pipette tips filled with medium inside multi-inlets, which additionally serve as plugs during feeding. Pressure used to push medium may be positive pressure represented by the arrow pointing down, in other embodiments the pressure is negative pressure represented by the arrow pointing up. FIG. 35C shows an exemplary schematic diagram of fluid flow in a device during chip prep, where 1, 2, 3, and 4 numbered ports are unplugged, while EDTA inlets and multi-inlet ports are plugged. Negative pressure (see direction upwards of thick arrows) is used to fill empty upper channels, then multi-inlets are also plugged. After filling, tubing is attached to inlets 1, 2, 3, and 4 of which at least one tube is attached to a pump.

FIG. 36A shows an exemplary diagram showing where blood is added to reservoirs along with any test agents. Thick arrows show the direction of fluid flow of blood out of the reservoirs, with smaller arrowheads showing the direction of flow upwards towards the inlets. FIG. 36B shows an exemplary diagram where the four open dots, shown diagonally within the open rectangle (arrow), represent the open (dispensing) ends of pipette tips where the other tip end is attached to a multi-pipetter so that fluid containing an agent, such as a conditional agent, e.g. a coagulation reagent in solution, such as Ca++, intended for adding to blood entering the test channels, is simultaneously added to three ports located below the three lower dots, one port each for three of the four reservoirs shown as black areas in the lower part of the chip, where each of the four microchannels is in fluidic communication with a corresponding reservoir. Thus, the solution is mixed into the blood contained in three reservoirs at one time. The remaining reservoir, when receiving a solution as a separate addition into the fourth reservoir port, not in line with the multi-channel pipette tips, upper right, is added/mixed separately from the other three reservoirs. In some embodiments, this fourth reservoir is used as a control without the addition of an agent in solution, such as a conditioning solution. FIG. 36C shows an exemplary diagram for preparing Outflow fluid for collection. Unplug EDTA input ports (dots at the top of the diagram), insert the dispensing end of 1 mL syringes for adding EDTA solution. Since a small amount of EDTA needed, flow downward is gravity driven, see arrowhead pointing down from the input. Each cm of liquid height=0.1 kPa in pressure; so that an optimal height of the on-chip device components is calculated for each type of chip.

FIG. 38 shows an exemplary schematic diagram of one embodiment of a microfluidic chip as an eight channel device. In some embodiments, a device induces, but is not limited to, two eight channel units, where two eight channel units are shown in this figure. In this embodiment, a single input port (shown by the circle at the top of the diagram-upper arrowhead) is connected to eight branching channels (which in some embodiments are tubes) flowing through resistors (located in between the components identified by the upper two arrowheads) for regulating the fluidic flow rated for providing equal flow rates of fluids entering each of the eight microchannels. Dots located after the resistors (middle arrowhead) represent each inlet per microchannel. The center dark lines (arrow) represents a side by side viewing area (shown in FIG. 31B), in part for use in analyzing (including but limited to observing) events occurring in parallel active regions of the microchannels. The lower shaded rectangles (lower arrowhead) represent on-chip reservoirs where one reservoir is in fluidic communication with one of the microchannels. This illustrates how some constructs fall within the same microscope field, while others fall within the range of the microscope stage.

FIG. 39 shows an exemplary schematic diagram of one embodiment of a microfluidic chip device having a single pressure source, i.e. common pressure source, shown at the top of the diagram, for applying pressure to both an input reservoir (e.g. blood inlet) and an additive reservoir, e.g. containing an anticoagulant solution. Serpentine channels serve as a resistors shown inline between the blood inlet and the chip, and the reservoir and the chip, for regulating the fluidic flow rates. The dotted lines represent an exemplary chip, e.g. thrombosis chip, while the circle in the lower right of the chip area represents and additive channel area as shown in FIG. 12. In some embodiments, fluidic connectors are tubes attached to on-chip ports represented by black circles within the dotted line outline of the chip. While not intending to limit the invention in any manner, in one embodiment, the resistors cause the two flows to be proportional under the application of the same pressure. This is useful when it is desired that the anticoagulant or calcium mix with the blood at a specific ratio to be effective. For example, in one embodiment, it is desired that the EDTA final concentration be 10 mM, whereas the calcium concentration goes to 20 mM. While FIG. 39 shows the blood inlet and anti-coagulant in separate containers, the present invention also contemplates the situation where the pressure source acts on a single container or component (e.g. a reservoir) that has been divided. For example, in one embodiment, the present invention contemplates modifying an existing reservoir into two reservoirs with a dividing wall.

FIG. 40A shows an exemplary off center overhead view of a reservoir assembly on a microfluidic chip where an arrowhead points to the connection between the luer of a syringe (representing an off-chip reservoir) with a blood inlet for adding fluid to an on chip reservoir. A white arrow points to an exemplary on-chip reservoir. FIG. 40B shows an exemplary overhead view of syringe attached to chip a reservoir as an assembly in the blood inlet. A circular component on the right of the chip represents a port. FIG. 40C shows an exemplary chip showing an enlarged view of the connection between the off chip (syringe) and on chip reservoir (arrow) at a blood inlet, showing the luer connection (arrowhead) with the inlet port.

FIGS. 41A-D shows exemplary schematic drawings of one embodiment of a microfluidic chip device demonstrating additional details of some of the components as shown in FIGS. 32A-C and 33. FIG. 41A shows an enlarged illustration of the branches (short arrows) merging with channels (long arrows) as shown within the circle labeled A in FIG. 41C. The arrowhead points to an exemplary input between a branch and a channel. FIG. 41B shows an enlarged illustration of the channels shown within the circle labeled B in FIG. 41C. FIG. 41C shows an illustration of the microfluidic device. FIG. 41D shows a 3D illustration of the microfluidic device where the branches (short arrows) and channels (long arrows) are shown in the black area and on-chip reservoirs (open triangles). The double headed arrow points to 2D vs. 3D drawings of corresponding reservoirs between FIG. 41C and FIG. 41D, respectively.

FIG. 42A shows an enlarged illustration of the channels in the active regions as shown within the circle labeled A in FIG. 42C. FIG. 42B shows an enlarged illustration of a resistor region shown within the circle in FIG. 42C. FIG. 42C shows an illustration of one embodiment of a microfluidic device where a single port has multiple branches, where each branch has a resistor, shown within the circle, such that after fluid flows through the resistors each branch has a flow rate equal to the other branches flow rate as the fluid enters the channels. FIG. 41D shows a 3D illustration of one embodiment of a microfluidic device where the branches (short arrows) and channels (long arrows) are shown in the black area. The double headed arrow points to 2D vs. 3D drawings of corresponding reservoirs between FIG. 42C and FIG. 42D, respectively. In some embodiments, the eight circles at the bottom of each of the two chip units shown (8 per chip) represent the output. In some embodiments, there is a single additive channel input (see the single circle at the bottom of the chip unit diagram that feeds in through a resistor (i.e. switchbacks or squiggles) that is associated with each of the 8 outputs.

DESCRIPTION OF THE INVENTION

Figure 1:
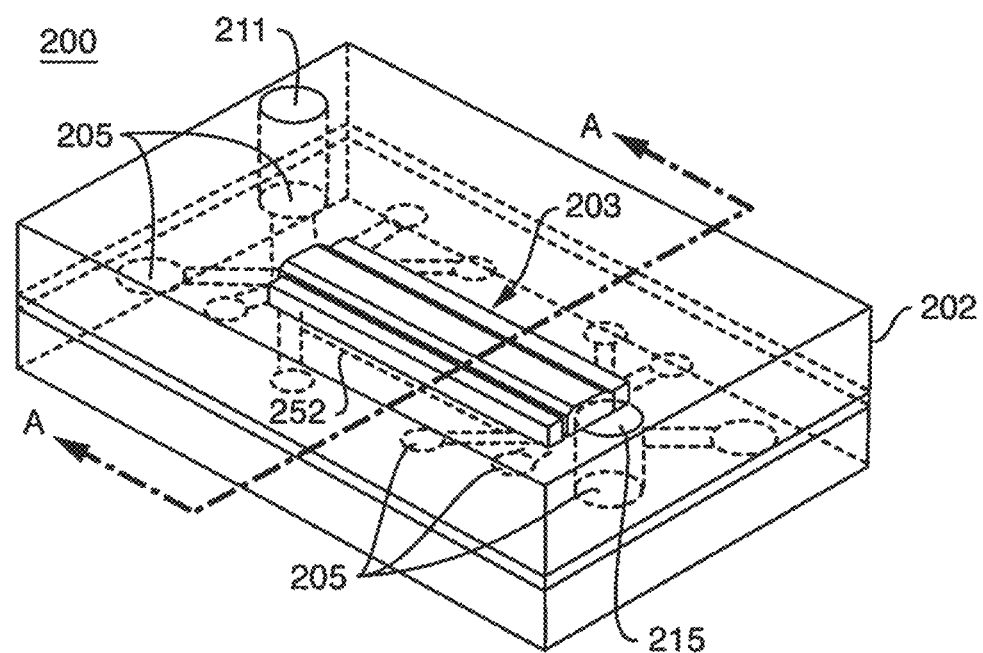
FIG. 1 illustrates a perspective view of one embodiment of a microfluidic device or chip showing input and output ports in fluidic communication with an active region or experimental region.

The present invention contemplates compositions, devices and methods of preventing, reducing, controlling or delaying adhesion, adsorption, surface-mediated clot formation, or coagulation in a microfluidic device or chip. In one embodiment, blood (or other fluid with blood components) that contains anticoagulant is introduced into a microfluidic device comprising one or more additive channels containing one or more reagents that will re-activate the native coagulation cascade in the blood that makes contact with it "on-chip" before moving into the active or experimental region of the chip.

I. Advantages of a Microflulidic-Chip Device

Advances in microfluidic engineering have recently made it possible to create miniaturized in vitro cell culture systems, known as organs-on-chips[29,30], in which human cells and tissues are subjected to fluid flow and mechanical stress in well-controlled three-dimensional geometries as microenvironments. Thus, organs-on-chips produce human-relevant physiological data that is used in biomedical science, toxicology and pharmacology.

Systems comprising organ components allow for controlled studies of organ-level aspects of human physiology and disease, and were successfully applied in the preclinical testing of therapeutics[31]. Microengineered on-chip systems containing human endothelium, perfused with human whole blood at physiological relevant shear rates, recapitulate many aspects of thrombosis (Jain, et al. Assessment of whole blood thrombosis in a microfluidic device lined by fixed human endothelium. *Biomedical Microdevices.* 18:73, 2016; Westein, et al. "Atherosclerotic geometries exacerbate pathological thrombus formation poststenosis in a von Willebrand factor-dependent manner." Proc. Natl. Acad. Sci. U.S.A 110, 1357-1362 (2013); Tsai, et al. In vitro modeling of the microvascular occlusion and thrombosis that occur in hematologic diseases using microfluidic technology. J. Clin. Invest. 122, 408-418 (2012); Westein, et al., "Monitoring in vitro thrombus formation with novel microfluidic devices." Platelets 23, 501-509 (2012). However, these on-chip blood vessels lack human-relevant physiological data. Unlike other systems, such as the Badimon chamber, which are designed for real-time monitoring for anti-coagulant properties of drugs in a clinical setting, the microengineered Vessel-On-Chip was designed, at least in part, for preclinical testing to select candidate drugs for efficacy (e.g. anticoagulants) or for safety (e.g. risk for thrombosis).

Therefore, a microfluidic-chip device was developed, as described herein, for overcoming such limitations of other chips for providing human-relevant physiological data. In one embodiment, a Thrombosis-On-Chip was created in part by perfusing microfluidic chips with human blood with an anticoagulant, such as citrate solution, added to outflowing blood samples to prevent clotting inside connectors and tubing. In some embodiments, a Vessel-On-Chip was created which in part provides advantages in allowing analysis of the outflowing blood samples over longer durations in time of experimental testing, In some embodiments, a Vessel-On-Chip was created which in part provides embodiments for testing certain combinations of healthy components, diseased components, and some healthy components with some diseased components. Components include but are not limited to normal healthy blood components, normal healthy cells, treated blood, treated cells, blood from diseased patients, cells from diseased patients, etc.

Advantages of using a microfluidic chip device (alternatively, a microfluidic chip) as described herein, include but are not limited to: providing a system enabling control over blood parameters, e.g. changing flow rates, changing components interacting within blood, etc.; providing a model designed to interface with microscope, e.g. enabling high speed real time imaging, etc., and providing an analysis on small volumes of fluids, e.g. using minimal volumes of blood. Further, advantages of using a microfluidic device as described herein, over other systems include but are not limited to: Capability to perform long term experiments; blood vessel-endothelial cell interaction, for one example, when cells line the device channels so there is not direct interaction between blood and device material interaction; direct monitoring and record of the inflammatory response; direct monitoring and record of blood reactivity; providing multiple modular geometries each modeling a specific aspect of flow dynamics; and potential application for patient-specific modeling the blood reactivity in vitro, e.g. for use in personalized medicine.

A. Embodiments of Microfluidic Chip Devices.

In some aspects, materials and methods are provided herein for use with modeling of blood flow and its effect on cells. In other aspects, materials and methods are provided herein for modeling the effect of cells on blood flow and its properties. Additionally, many variations of the materials are contemplated for use in providing microfluidic devices, including but not limited to materials allowing for partial or full views of microfluidic channels.

Thus in one embodiment, modeling blood flow on a microfluidic chip mimics events associated with blood clotting, such as Thrombosis-On-Chip. In some embodiments, modeling blood flow on a microfluidic chip involves lining microfluidic channels with endothelial cells.

In one embodiment, modeling blood flow on a microfluidic chip enables hematodynamic modeling, including but not limited to cardiovascular system (involving wave propagation and flow-induced instabilities of blood vessels, capillary-elastic instabilities, etc.

In some embodiments, modeling blood flow on a microfluidic chip involves lining microfluidic channels with cells derived from blood vessel cells, for e.g. cells isolated from blood vessels obtained from patients (including but not limited to live patients undergoing biopsies, surgery, etc), from cadavers and from commercial sources. In some embodiments, modeling blood flow on a microfluidic chip involves specific geometries for producing certain types of biofluid mechanics within tubes, e.g. including but not limited to rigid microchannels, in part for identifying factors related to fluid mixing, internal flow, effects on blood clotting, etc.; flexible microchannels, in part for identifying factors when mimicking vessel wall deformation in relation to internal flow, effects on blood clotting, pressure-drop/flow-rate relations, and combinations thereof.

Cells may refer to cells disposed within or coating a microchannel, such as endothelial cells, and cells contained in the blood added to the microchannels. When we mention cells contained into the blood we refer both to cells normally present in the blood of healthy patient (white cell, red cell and other particulates such as platelet) and cells not normally present into the bloodstream such as metastasis or other microorganisms which could be present in diseased patient.

Contemplated experiments focus on several aspects, such as measuring how: 1) mechanical forces and geometry of blood vessel affect the behavior of the cells contained into the blood; 2) blood cells alter the rheological properties of blood in reaction to mechanical stresses; 3) blood/endothelial cells interaction affects the rheological properties of the blood and the properties of the endothelia surface; 4) epithelial and parenchymal cells affect endothelial cells and rheological blood properties in response to external stimuli and stresses (chemical, mechanical, biological etc), and the like.

In other words microfluidic devices (including chips) described herein are contemplated to provide a means for: 1) recreating several perfusable vessel geometries which can mimic an actual healthy simulation using components from healthy patients, mimic a diseased blood vessel using components from patients with a disease or at risk of a disease, and mixed simulations using combinations of components from healthy patients with components from patients with a disease or at risk of a disease; 2) lining the vessel with living endothelial cells specific for (i.e. isolated from or derived from or associated with) each specific organ under study; 3) creating vessels for use in flowing blood through (i.e. through a microchannel lined with simulated blood vessels), where blood is isolated from an individual patient; 4) providing a system for integration with the Organ-on-Chip concept and used to study the effect of the interaction of multiple cell types on blood (for example, one can study how epithelial/parenchyma/mesenchymal cell interact with endothelial cell and how those affect the blood and vice versa); 5) visualizing the lumen of reconstructed blood vessels (i.e. blood vessel mimics) using microscopy at high speed viewing/imaging/recording such as with photography/videos and high resolution (i.e. capable of subcellular level viewing).

B. Computational Hemodynamic Modeling.

Computational hemodynamic modeling is divided into at least three main descriptive groups:

1) A real time imaging system refers to imaging based on doppler ultrasound, CT (Computed tomography) angiography and MR (magnetic resonance) angiography, or similar which produce image or video of the blood flow in real time within a patient. Thus, real time imaging systems refer to devices capable to visualize the lumen of blood vessels in the body. However, in general, application of this techniques are limited because their use requires exposure to x-ray or radioactive contrast agents which limit their application on human for safety reason. Long term exposure to such agents increase exponentially the risk to develop a cancer, plus high doses of radiation commonly associated with various side effects which include nausea, vomiting, pain, swelling, redness or cutaneous rash of the treated area. Other techniques based on the use of ultrasound are generally safer, but the prolonged use on patients is not recommended or in some cases contraindicated. Another limiting factor in the use of these techniques for modeling blood resides in the fact that these techniques have a limited resolution (generally sub millimeter), which does not allow to visualize cellular structure or to perform studies involving the effect of the blood flow on cells.

2) Computational modeling may also provide a mathematical description of blood flow, in models were the blood is approximated to an inert colloid/viscoelastic fluid. This type of modeling generally requires computation analysis. Application of computational modeling is generally limited in biology because such models merely provide a mathematical description of the blood as a fluid, which does not include effects of the behavior of cells within the blood and further does not provide a descriptive model of the behavior of cells contained within blood and their effect on blood properties or to describe blood interaction with other cells. Since computational models are incapable of modeling cell behavior they are intrinsically inaccurate to describe the biology of blood.

Therefore, at least in part to address unmet needs, we have developed an optically transparent platform made of PDMS for hemodynamic modeling and testing, which is a tools for modeling the physic of blood flow and the biological behavior of blood cells in it contained under pre-set fluidic dynamic regimes and that allows 3D imaging at high resolution in real time of the blood flow. The specific setup can also be used as diagnostic tools in personalized medicine.

High resolution high speed computational imaging of the blood enables a detailed visualization of the complex shear stress velocity and the pressure fields which can be directly correlated with cellular behavior. Since the platform is a modular system and the fluidic parameters can be finely tuned the system can be set to extrapolate information at different length scale by connecting several modules containing a specific geometry either in parallel or in series and time scale by setting different working time on the peristaltic pump.

Furthermore, the platform could be used as a diagnostic tools in personalized medicine application. Specifically, after defining specific metrics using blood from patients with blood disorders, it would be possible to make prediction about their response to medical treatments, drugs and diets. In the future, one can envision the routine incorporation of these data in hospital practice to help virtual treatment planning of the patient as it occurs already in other medical disciplines.

This modular platform permits to integrate multiple rheological/geometrical units into a comprehensive system to investigate the impact of various conditions simultaneously. The full-integrated system offers the possibility of understanding, holistically, the impact of cardiovascular disease upon individual patients.

The microfluidic chip devices described herein, are contemplated for use when integrated with other types of microfluidic chip devices and used to study the effect of the interaction of multiple cell types on blood, to study how inflammation of epithelia and parenchyma, drugs, chemical compounds and physical forces affect/influence the behavior of the endothelial cells lined in the channel and how all of them can affect blood and blood-cells behavior (white cells, red cells and platelets). The applications of the system involves also, but is not limited, to the study of complex events such as thrombosis, thromboembolism, aneurism, atherosclerosis, ischemia and the significance of lesions generated by pressure and other mechanical stresses that can affect blood and endothelial cells.

C. Microfluldic Devices for Studying Thrombotic, Blood Clotting, Events

In addition to evaluating clinically relevant aspects of thrombosis, such as platelet-endothelium interaction, platelet aggregation and fibrin formation, studied in vitro within a microfluidic-chip device, these microfluidic chips can be used to detect early stages in drug-induced thrombosis and thromboembolism.

Further, additional advantages of using microfluidic-chip device testing of thrombosis include but are not limited to evaluating soluble biomarkers. As described herein, we demonstrate the significance of our model for preclinical drug testing in one example, by studying the pro-thrombotic effects of huSC8. Our results confirm that platelet adhesion to endothelium, platelet aggregation, and fibrin formation can be measured and visualized in microfluidic-chip device systems. In addition to detecting platelet adhesion to the endothelium, the formation of a network of fibrin clots within the chip following treatment was confirmed by imaging and scanning electron microscopy.

This microfluidic-chip device design enabled collection of eluents, from an additive channel attached to the outflow port, for quantification of biomarkers such as the thrombin-antithrombin complex (TAT).

Another advantage of using a microfluidic-chip device was demonstrated by its use to analyze multiple aspects of thrombosis, such as platelet adhesion, aggregation, fibrin formation and TAT release, all in a single assay.

A microfluidic-chip device is contemplated for use in testing patient-specific blood as it flows through the chip, including but not limited to patient-specific normal and/or diseased tissue/cells.

Thus drug treatments, e.g. anticoagulants, such as an anti-platelet drug, including but not limited to FDA-approved Eptifibatide, may be tested In vitro. Further, candidate therapeutic drugs, such as therapeutic antibodies, e.g. treatment using hu5c8 as an immune complex with sCD40L: $IC_{5c8}$, may be used to identify potentially adverse side effects as shown herein, that duplicated adverse side found during human clinical trials.

In some embodiments, the resulting characteristic temporal and spatial indices were sensitive enough to distinguish activated platelets (e.g., due to inflamed endothelial cells) and non-activated platelets. Thus, the temporal and spatial indices can be used as markers to diagnose diseases or disorders (e.g., platelet-associated disease or disorder), to select appropriate therapy (e.g., anti-platelet and/or anti-inflammation therapy), to monitor treatment efficacy (e.g., to prevent recurrent thrombosis or bleeding), drug screening and/or to determine drug toxicology. Accordingly, embodiments of various aspects described herein relate to methods, systems, and compositions for determining dynamic interaction of cells with each other, and/or with other cell types, and uses thereof.

Moreover, a microfluidic-chip device is contemplated for use in identifying "at risk" patients, e.g. so that simulated clinical trials might be done using blood and cells from a patient in vitro, thus reducing actual harm in patients that may have an adverse reaction to a particular therapy if tested in vivo.

In some embodiments, the present invention contemplates a method of determining if a subject is at risk, or has a disease or disorder induced by cell dysfunction and/or abnormal cell-cell interaction. The microfliuidic device can be used for diagnosis and/or prognosis of a disease or disorder induced by blood cell dysfunction (e.g., platelet dysfunction), and/or guiding and/or monitoring of an anti-platelet and/or anti-inflammation therapy. Non-limiting examples of the disease or disorder induced by blood cell dysfunction (e.g., platelet dysfunction) include, but are not limited to thrombosis, an inflammatory vascular disease (e.g., sepsis, or rheumatoid arthritis), a cardiovascular disorder (e.g., acute coronary syndromes, stroke, or diabetes mellitus), vasculopathies (e.g., malaria, disseminated intravascular coagulation), or a combination of two or more thereof.

In one embodiment, the pro-thrombotic effects of drugs and antibodies are revealed by in vitro testing in the microfluidic device. In one embodiment, the pro-thrombotic effect of hu5C8 was revealed in vitro using disease-relevant concentrations of sCD40L and clinically relevant concentrations of hu5C8. Indeed, previous studies were conducted using platelets frequently exposed to supraphysiological concentrations of sCD40L (1000 times higher than serum levels of sCD40L found in disease states)[23,27]. In our model, thrombosis induced by hu5C8 was dependent on the FcγRIIa receptor. In fact, thrombosis was prevented by IV.3, a blocking antibody against FcγRIIa and hu5C8-mediated thrombosis was not detected when we used hu5C8-IgG2σ, a molecule formatted not to bind the FcγRIIa receptor. Our results provide confidence that the newer generation anti-CD154 mAbs that do not bind FcγRIIa receptors have a low risk for thrombosis[23]. The ability of this microfluidic Vessel-On-Chip to provide reliable measurements of clinically relevant endpoints makes it a suitable platform to assess risk for thrombosis of a broad class of molecules developed for therapeutic applications.

II. Incidents of Drug-Induced Thromboembolism During Clinical Trials.

Activation of T cells via CD40 ligand (CD40/CD154) binding is one step towards the initiation of the adaptive immune response. Blocking of CD40L-mediated signaling represents a powerful therapeutic strategy[1] for treatment of auto-immune disorders[2] and for preventing organ transplant rejection[3]. Pre-clinical studies conducted on animal models have demonstrated that monoclonal antibodies (mAbs) against CD40L can be used to suppress organ transplant rejection[3-8] or the auto-immune response[9]. However, the development of anti-CD40L mAbs was halted for several years because of multiple incidents of thromboembolism and cardiovascular events during clinical trials of the drug candidates huSC8 and IDEC-131, which were under development for treatment of lupus[9,10] and/or Crohn's disease[11,12,13-15].

In addition to expression on T cells, CD40L is also expressed on activated platelets where, after translocation to the surface, it sheds as soluble CD40L (sCD40L)[16]. Platelets also represent the major source of circulating sCD40L[17-19], with high concentrations reported in patients with inflammatory diseases[20,21]. It is believed that thrombosis by hu5C8 is mediated by ligation of a high-ordered immune complex (IC) of hu5C8 with sCD40L to the FcγRIIa receptor specifically expressed on human platelets[10,22-27]. Given these findings, new anti-CD40L mAbs under development should have both a demonstrated efficacy along with a great degree of confidence (i.e. data supporting) a lack thrombosis induction in the presence of sCD40L[28]. The lack of robust models able to predict the mAb-mediated thrombosis by this complex mechanism is one of the main obstacles for the advancement of new monoclonal therapeutics against CD40L. While platelet aggregation and activation continue to be the gold-standard for in vitro assessment of risk for thrombosis, an in vitro model that truly captures the complexity of human platelet aggregation as well as activation of the coagulation cascade would address the unmet need for systems that can aid in selecting compounds with reduced risk for thrombosis.

As described herein, we demonstrate that Vessel-On-Chip technology is suitable for studying drug-induced thrombosis that is relevant to humans in the context of disease and drug treatment. Perfusion of a biomimetic vessel on-chip with human blood samples containing pathophysiologically realistic levels of the inflammatory cytokine sCD40L (CD154) and relevant concentrations of hu5C8, an anti-CD154 monoclonal antibody that was intended for treatment of autoimmune disorders, leads to enhanced platelet-endothelial adhesion, platelet aggregation, and fibrin clot formation. The thrombotic endpoints detected in the chip are consistent with clinical findings of thrombosis by hu5C8 that led to termination of its clinical trials. In addition, treatment-related increase in thrombin anti-thrombin (TAT) complex in the eluate from the chips demonstrates an ability to couple imaging endpoints with biomarker detection in this model. The thrombotic effects could be prevented by a blocking antibody against FcγRIIa receptors expressed on platelets or by using an anti-CD154 mAb modified not to bind FcγRIIa receptors.

Our results demonstrate that Vessel-On-Chip technology can be used to detect clinically relevant thrombotic effects in vitro, even when such effects are mechanistically complex.

DETAILED DESCRIPTION OF EMBODIMENTS OF THE INVENTION

FIG. 1 schematically shows one embodiment of a microfluidic device 200 that includes a plurality of ports 205 in fluidic communication with a microchannel 203. The center of the microchannel 203 serves as the active region or experimental region (see 207 of FIG. 1 and FIG. 2). The active region or experimental region is typically where cells are cultured, where cells interact, and/or where cells are tested. In one embodiment, the active region is a tissue-tissue interface simulation region where cell behavior and/or passage of gases, chemicals, molecules, particulates and cells are monitored. This region can be monitored, e.g. with a microscope or other imaging system (not shown). Also shown is one embodiment for the outer body 202 of the device 200; input port 211 and output port 215; optional vacuum chambers 252 and a horizontal orientation plane in dotted lines A, including an exemplary cross-section of microchannel 203.

Figure 2:
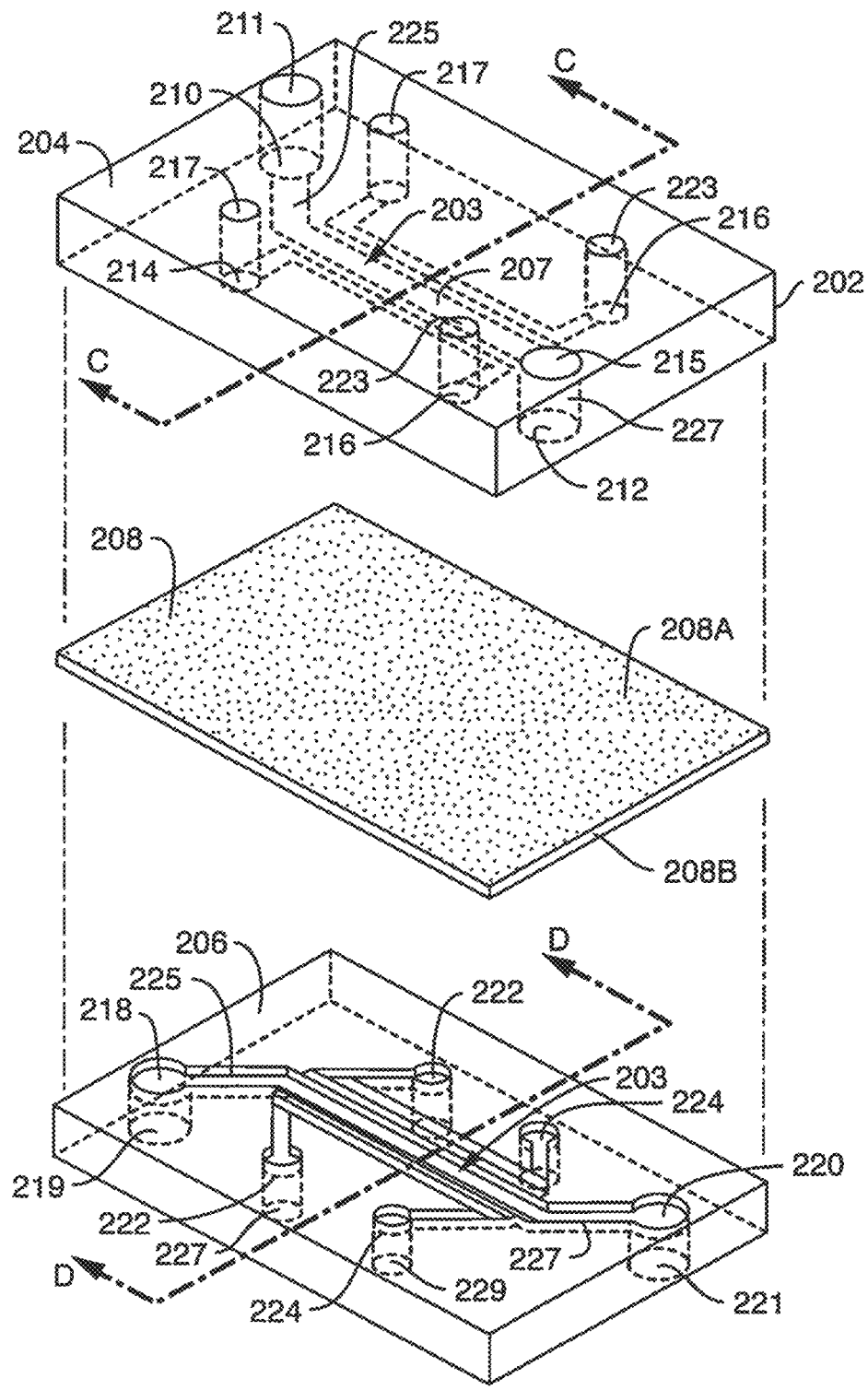
FIG. 2 illustrates an exploded view of the microfluidic device of FIG. 1

FIG. 2 illustrates an exploded view of the embodiment shown in FIG. 1. In particular, the outer body 202 of the device 200 is preferably comprised of a first outer body portion 204, a second outer body portion 206 and an intermediary porous membrane 208 configured to be mounted between the first and second outer body portions 204, 206 when the portions 204, 206 are mounted to one another to form the overall body. Both input ports 211; 219 and output ports 215; 221 with contact regions 210, 212, 218 and 220, respectively; inflow channels 225 and outflow channels 227; microchannels 203 with a center region 207; in addition to supplementary ports 217, 223, 227 and 229, with corresponding contact regions 214, 215, 222 and 224; are shown. Further, membrane 208 has two surfaces 208A and 208B. Dotted lines show horizontal orientation planes C and D, including exemplary cross-sections of microchannels 203.

Figure 4B:
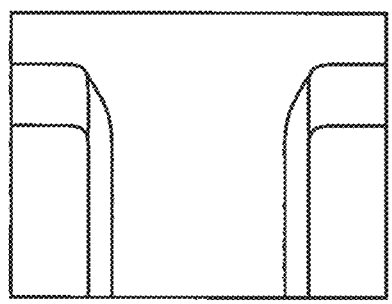
FIGS. 4A-C shows one embodiment of on-chip mixing using a dual input, i.e. two additive channels in fluidic communication.
Figure 4C:
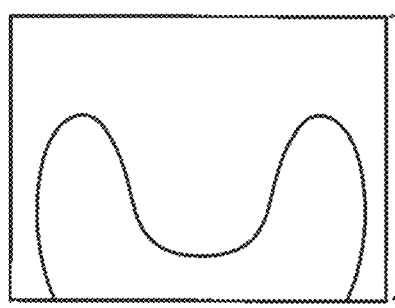
Figure 4A:
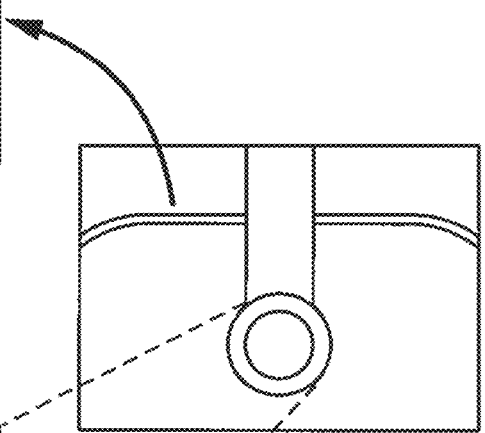

In one embodiment, the present invention contemplates the inclusion of additional fluid inputs to increase the mixing of reagents and cells, and in particular, the mixing of anticoagulant with blood. FIGS. 3A-C shows one embodiment of on-chip mixing using a single input, i.e. a single additive channel in fluidic communication. FIG. 3A shows the additive channel attached to the microfluidic port of the microfluidic device. FIGS. 3B and 3C are photographs showing the single input stream and single input mixing. FIGS. 4A-C show one embodiment of on-chip mixing using a dual input, i.e. two additive channels, one on one side of the microchannel (near the input port) and on the other side of the microchannel. FIG. 3A shows a schematic of the two additive (dual input) channels attached to the microchannel of the microfluidic device (near the input port of the microfluidic device). FIG. 4B and FIG. 4C are photographs showing the dual input streams and dual input mixing, respectively. Both a single input and double input additive channels minimize the exposure of activated blood to components of the chip, i.e. exposure to materials that may impact the results in the active region or experimental region of the chip.

One embodiment of on-chip mixing uses a dual input, i.e. two additive channels in fluidic communication is shown in FIGS. 4A-C. FIG. 4A shows a schematic of the dual input additive channels attached to the microfluidic port of the microfluidic device. FIG. 4B and FIG. 4C are photographs showing the dual input streams and dual input mixing, respectively.

Figure 5B:
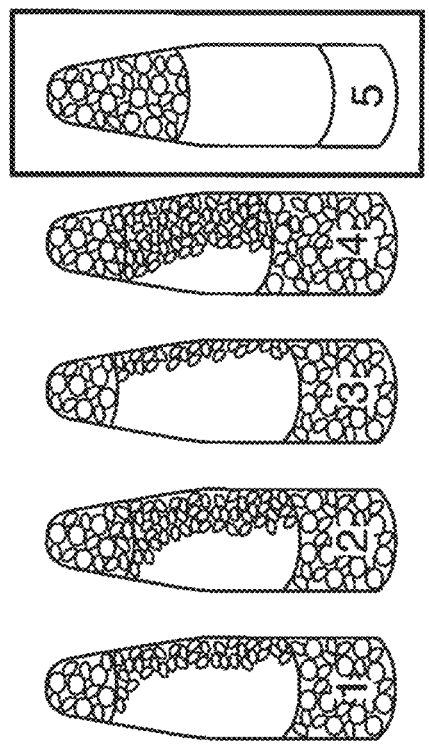
FIGS. 5A-B shows exemplary illustrations of photographs demonstrating on-chip mixing of anticoagulant.
Figure 5A:
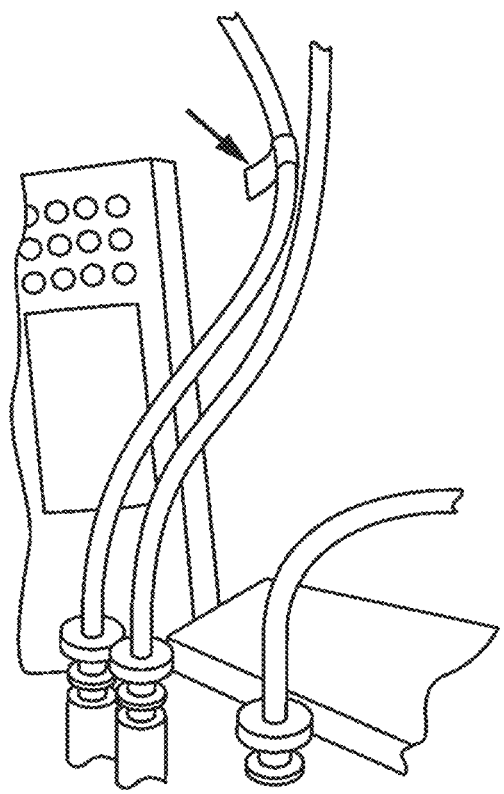

FIGS. 5A-B shows exemplary photographs demonstrating on-chip mixing of anticoagulant. FIG. 5A shows tubing connecting a source of sodium citrate to the microfluidic device (not shown). On-chip mixing with sodium citrate (see tag—pointed at by the arrow) allows samples to flow freely, while lack of anticoagulant input clogs collection tubes and can slow or completely stop flow. FIG. 5B shows five tubes, four of which were treated on-chip with anticoagulant and can be analyzed. Tube 5 was not treated and contains a solid mass of coagulated blood, which cannot be used for testing. FIG. 5B shows upside down microcentrifuge tubes with blood clots in the pointed ends and free blood cells in solution in the lower flat ends. These tubes started upright (pointed ends down), with 1-5 different treatments of a liquid solution of red blood cells. Then the tubes were spun down in a microcentrifuge on an angle with the pointed ends down. After the tubes were taken out of the centrifuge they were placed upside down with the clots staying in the pointed ends, with smaller—lighter clots sticking to the tube along one side (because it was on an angle as it was spun (tubes 1-4)) and free red blood cells that fell by gravity through the clear fluid into the lower ends where the numbers are located. Tube 4 has more free red blood cells than Tubes 1-3. Unlike Tubes 1-4, Tube 5 has heavy blood clots that stayed in the pointed end with clear fluid below.

In one embodiment, blood (or other fluid with blood components) that contains anticoagulant is introduced into a microfluidic device comprising one or more additive channels containing one or more reagents that will re-activate the native coagulation cascade in the blood that makes contact with it "on-chip" before moving into the experimental region of the chip. FIGS. 6B and 6C are images showing fluorescently-labeled platelet aggregates, demonstrating clotting in the untreated sample. FIGS. 6D and 6E are images for the treated sample, with labeled platelets from the anticoagulant treated sample that are dispersed in the blood liquid phase, demonstrating an uncoagulated state. The platelets were labeled with CD41-TRITC antibody, demonstrating that Cells can be visualized with antibody binding.

Figure 7B:
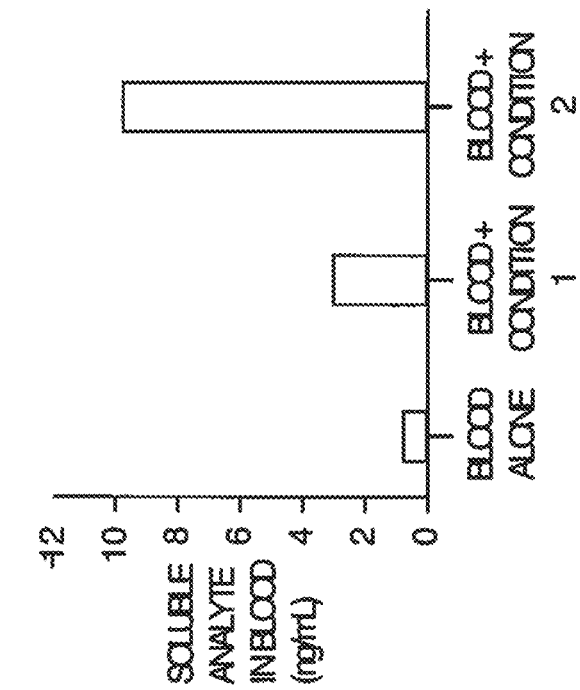
FIG. 7B is the determination of thrombin/anti-thrombin (TAT) complex concentration in blood after treatment with pro-coagulant factors.
Figure 7A:
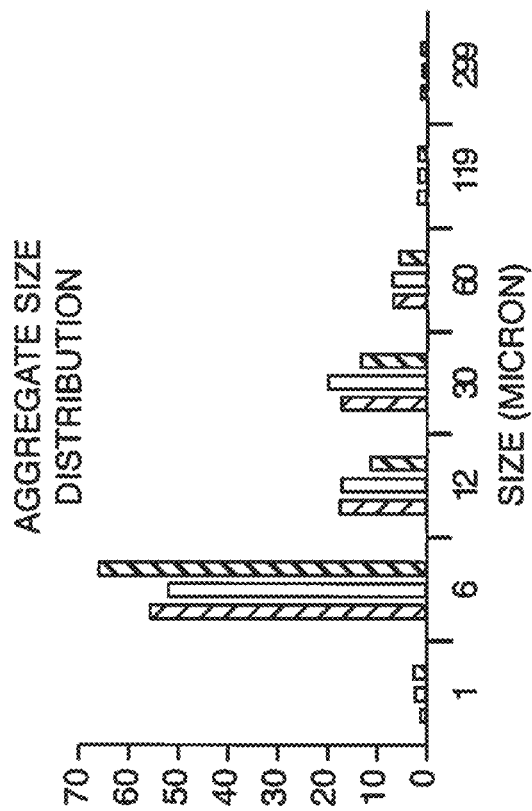
FIG. 7A is a clot size analysis of platelet aggregates that occurred in the blood during testing, demonstrating the distribution of sizes that occur during testing.

Blood contains many cell types along with the plasma liquid phase, all of which are available for study and testing in uncoagulated samples. A variety of tests can be performed in the microfluidic device using anticoagulated blood, including but not limited to platelet function tests, including clot measurement. FIG. 7A shows the size distribution of clots in samples from various donors. FIG. 7B shows that the analysis of soluble factors (TAT) in response to the addition of pro-coagulant factors to the blood.

Figure 8:
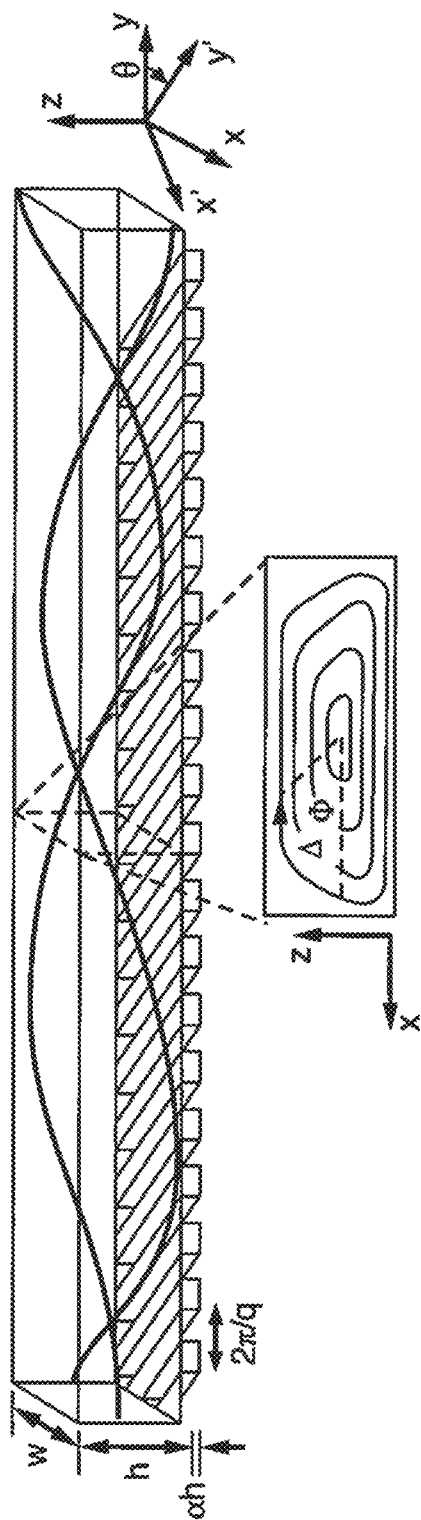
FIG. 8 is a schematic showing an additive channel with ridges for enhanced mixing. In this embodiment, a three-dimensional twisting flow is generated in the mixing channel with obliquely oriented ridges on one wall.

The additive channel(s) or the microchannel itself can contain features that increase mixing. For example, in one embodiment, the additive channel(s) or microchannel (or portion thereof) can contain ridges. In one embodiment, the present invention contemplates a three-dimensional twisting flow in a mixing microchannel channel with ridges on one wall (or a portion of one wall, e.g. at the beginning before the active region). FIG. 8 shows a schematic diagram of microchannel with obliquely oriented ridges for enhanced mixing. The coordinate system (x y z) defines the principal axes of the channel and of the ridges. The angle (theta) defines the orientation of the ridges with respect to the channel. The amplitude of the ridges is small compared to the average height of the channel. The width of the channel is w and principal wavevector of the ridges is q. The lines represent trajectories in the flow. The streamlines of the flow in the cross section are shown below the channel. The angular displacement is evaluated on an outer streamline.

Figure 9:
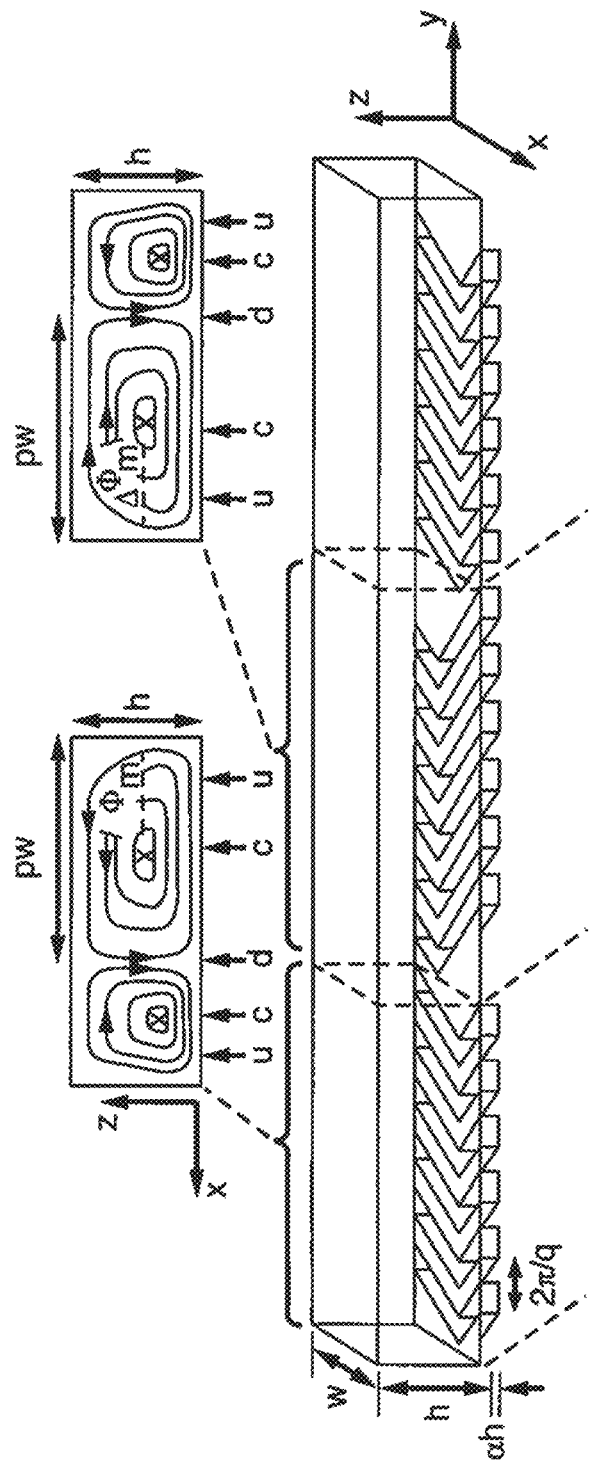
FIG. 9 is a schematic showing an additive channel with a staggered herringbone design of ridges for enhanced mixing. In this embodiment, a mixing cycle is composed of two sequential regions of ridges; the direction of asymmetry of the herringbones switches with respect to the centerline of the channel from one region to the next. The streamlines of the flow in the cross section are shown schematically above the channel.

FIG. 9 shows one embodiment of a microchannel (or portion thereof) with a staggered herringbone (SH) design of ridges for enhanced mixing. The schematic diagram shows one-and-a-half cycles of the SH. In one embodiment, a mixing cycle is composed of two sequential regions of ridges; the direction of asymmetry of the herringbones switches with respect to the centerline of the channel from one region to the next. The streamlines of the flow in the cross section are shown schematically above the channel. The average angular displacement of a volume of fluid along an outer streamline over one half cycle in the flow generated by the wide arms of the herringbones can be calculated. The fraction of the width of the channel occupied by the wide arms of the herringbones is p. The horizontal positions of the centers of rotation, the upwellings, and the downwellings of the cellular flows are indicated by c, u, and d, respectively.

Figure 10A:
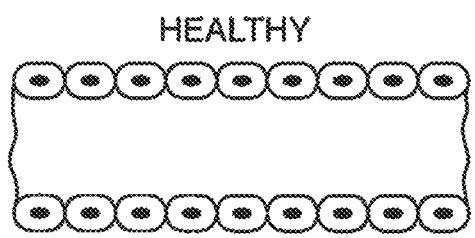
FIGS. 10A-D shows schematics depicting platelet thrombus formation over a monolayer of living endothelium. In a microchannel covered on all sides with untreated living endothelium (FIG. 10A), whole blood flows without clotting (FIG. 10B). In contrast, platelet-rich thrombus forms (FIG. 10C) if the endothelium is prestimulated by a pro-inflammatory cytokine, such as TNF-alpha, due to expression of procoagulatory proteins at its surface (FIG. 10D). In some embodiments, the responses of blood under flow shown in the figures can be reconstituted using similar microchannels that are lined by a chemically preserved (e.g. fixed) endothelium.
Figure 10D:
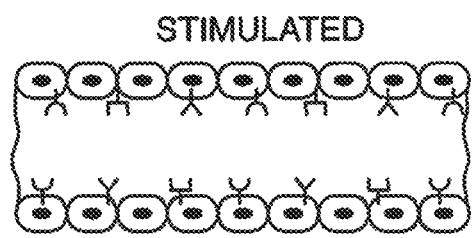
Figure 10B:
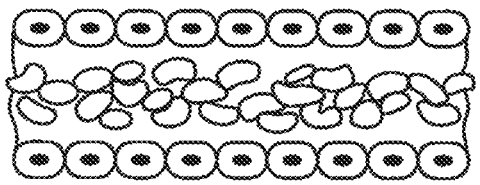
Figure 10C:
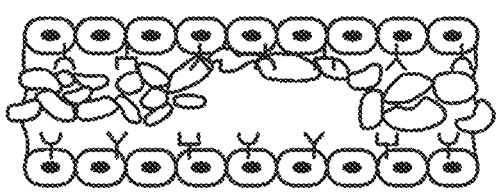

FIGS. 10A-D shows schematics depicting platelet thrombus formation over a monolayer of living endothelium. In a microchannel covered on all sides with untreated living endothelium (FIG. 10A), whole blood flows without clotting (FIG. 10B). In contrast, platelet-rich thrombus forms (FIG. 10C) if the endothelium is prestimulated by a pro-inflammatory cytokine, such as TNF-alpha, due to expression of procoagulatory proteins at its surface (FIG. 10D). In some embodiments, the responses of blood under flow shown in the figures can be reconstituted using similar microchannels that are lined by a chemically preserved (e.g. fixed) endothelium.

Figure 11:
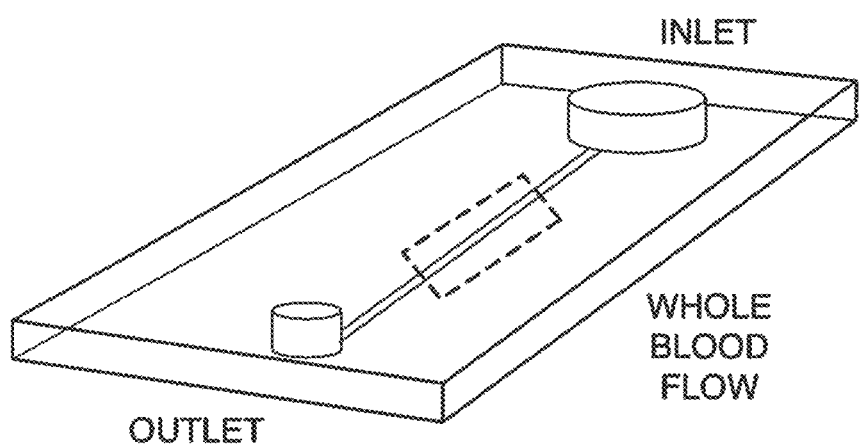
FIG. 11 is a diagram of a simple microfluidic device or chip showing inlet and outlet ports in fluidic communication with a single microchannel, with the active region or experimental region of the channel highlighted (dashed line).

FIG. 11 is a diagram of a simple microfluidic device or chip showing inlet and outlet ports in fluidic communication with a single microchannel, with the active region or experimental region of the channel highlighted (dashed line).

In one embodiment, the blood (or other fluid with blood components) is further treated as it leaves the active region of the microchannel, or immediately thereafter, in order to reduce the chance of clotting after testing. In one embodiment, the present invention contemplates one or more additive channels (positioned near an output port) containing one or more reagents that will inactivate the native coagulation cascade in the blood that makes contact with it "on-chip" as it leaves the active or experimental region of the chip, permitting the blood to flow out the output port. While one additive channel can be used, it has been found empirically that two channels (one on either side of the output port or end of the microchannel) better control clotting.

Figure 12:
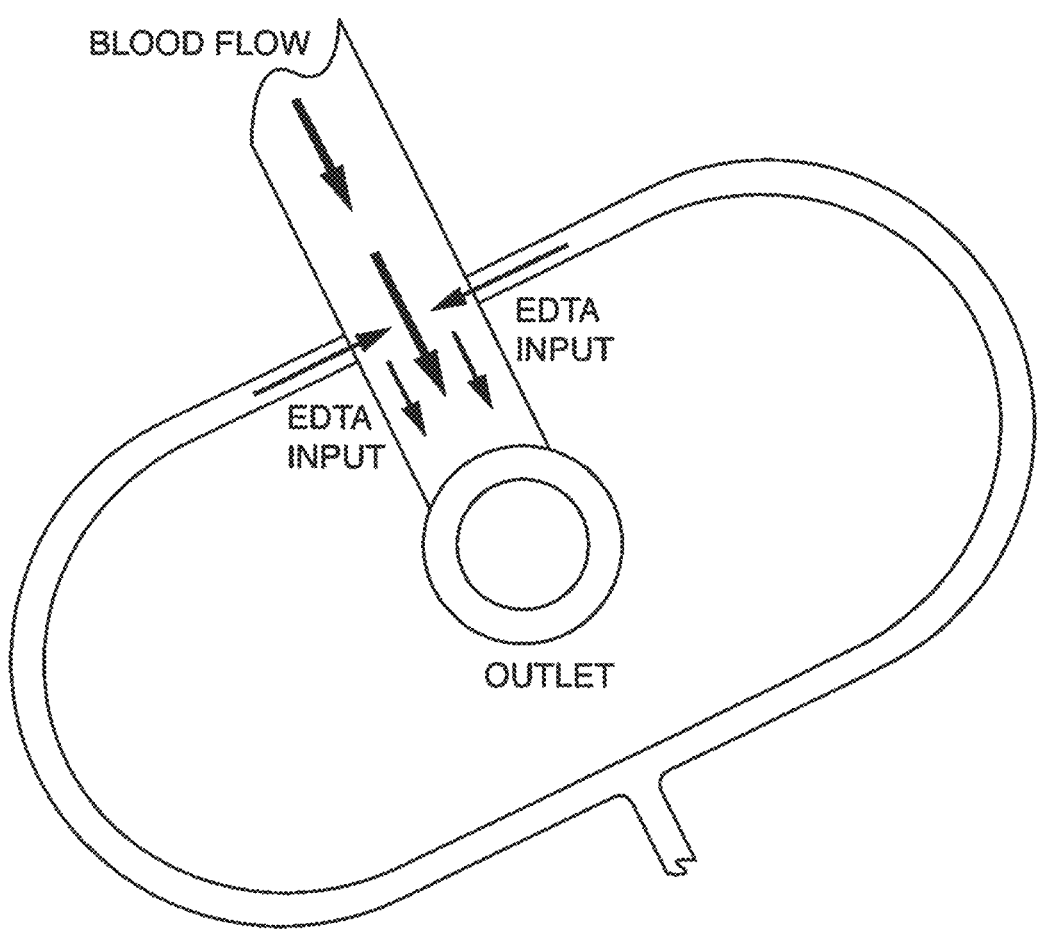
FIG. 12 is a schematic of one embodiment of a microfluidic device showing the end of the microchannel and outlet port in fluidic communication with two additive channels comprising anticoagulant, so that the sample leaving the microchannel remains fluid as it approaches the outlet port and exits the microfluidic device.

FIG. 12 shows an embodiment with two additive channels are employed. As the sample flows towards the outlet (output port), an anticoagulant (e.g. EDTA) is introduced from both sides of the microchannel via the two additive channels in fluidic communication therewith. The EDTA enters and coats the sides of the microchannel (FIG. 12, see arrows), reducing the chance that the blood will contact the walls of the microchannel. As the blood flows (see arrows) the EDTA mixes with that portion of the blood coming in contact with it. FIG. 12 is a schematic of one embodiment of a microfluidic device showing the end of the microchannel and outlet port in fluidic communication with two additive channels comprising anticoagulant, so that the sample leaving the microchannel remains fluid as it approaches the outlet port and exits the microfluidic device. It is not meant that 100% of the EDTA (or other anticoagulant) coats the sides of the microchannels. Indeed, some of the EDTA mixes with the blood sample flowing through the microchannel (see large arrows demonstrating fluid flow from the channel towards the outlet). In other words, EDTA flowing from the EDTA input contacts blood flowing through the microchannel (demonstrated by smaller directional arrows pointing towards the outlet) then flows as a mixed solution out of the Outlet port. It is desired that the amount of EDTA (or other agent) be sufficient to prevent the blood from coagulating in the channel. Thus, a ratio of EDTA to blood is contemplated in some embodiments.

Figure 13:
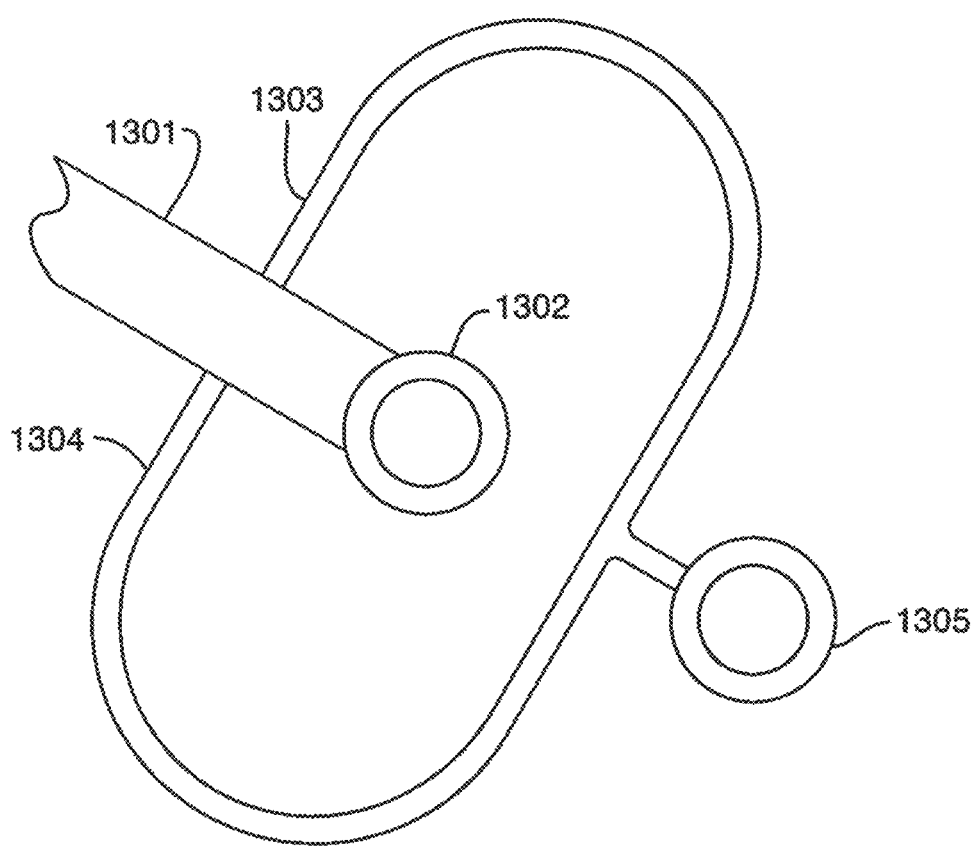
FIG. 13 is a schematic of a partial top view of one embodiment of a microfluidic device showing one end of the microchannel terminating at a first port, the microchannel in fluidic communication with two additive channels (one on either side) connecting to a second port (e.g. for adding the additive).

FIG. 13 is a schematic of a partial top view of one embodiment of a microfluidic device (the complete device is not shown) showing one end of the microchannel 1301 terminating at a first port 1302, the microchannel in fluidic communication with two additive channels 1303 and 1304 (one on either side) connecting to a second port 1305 (e.g. for adding the additive). Thus, in one embodiment, an additive channel located at a port has a single input port for the additive. In other words, one additive channel may have an individual additive input port, not shared with another additive channel. However, it is not meant to limit the number of additive channels connected to one additive input port, see exemplary embodiments in FIG. 13, wherein one embodiment shows 1305 as a single input port for two fluidically connected additive channels, 1303 and 1304. Thus, in one embodiment, two "additive channels" are plumbed together to a single additive input port, sometimes this port is referred to as an "EDTA input", see FIGS. 34 and 35. While the term EDTA input is used herein, it is not meant to limit the type of anticoagulant introduced into an EDTA input, such that other types of anticoagulants such as citrate, etc., may also be added for flowing through an EDTA input as an additive channel.

Figure 14:
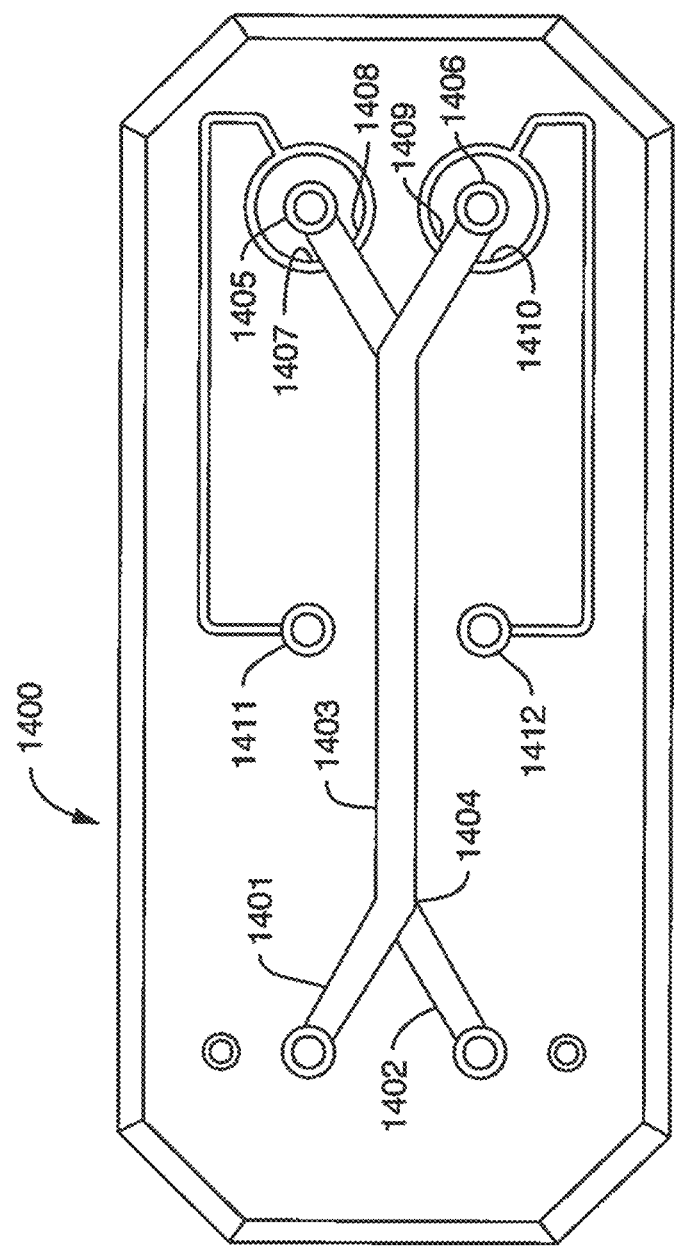
FIG. 14 is a schematic of a complete top view of one embodiment of a microfluidic device showing two microchannels aligned with one another (i.e. the main body of the first channel is above the main body of the second channel), where each end of each microchannel terminates at a port, wherein each microchannel is in fluidic communication with two additive channels (one on either side just prior to the port), each additive channel connecting to separate port (e.g. for adding the additive).

FIG. 14 is a schematic of a complete top view of one embodiment of a microfluidic device 1400 showing two microchannels 1401 and 1402 aligned with one another (i.e. the main body 1403 of the first channel is above the main body 1404 of the second channel), where each end of each microchannel terminates at a port 1405 and 1406, wherein the first microchannel is in fluidic communication with two additive channels 1407 and 1408 (one on either side just prior to the port), wherein the second microchannel is in fluidic communication with two additive channels 1409 and 1410 (one on either side just prior to the port), each additive channel connecting to separate port 1411 and 1412 (e.g. for adding the additive).

Figure 15:
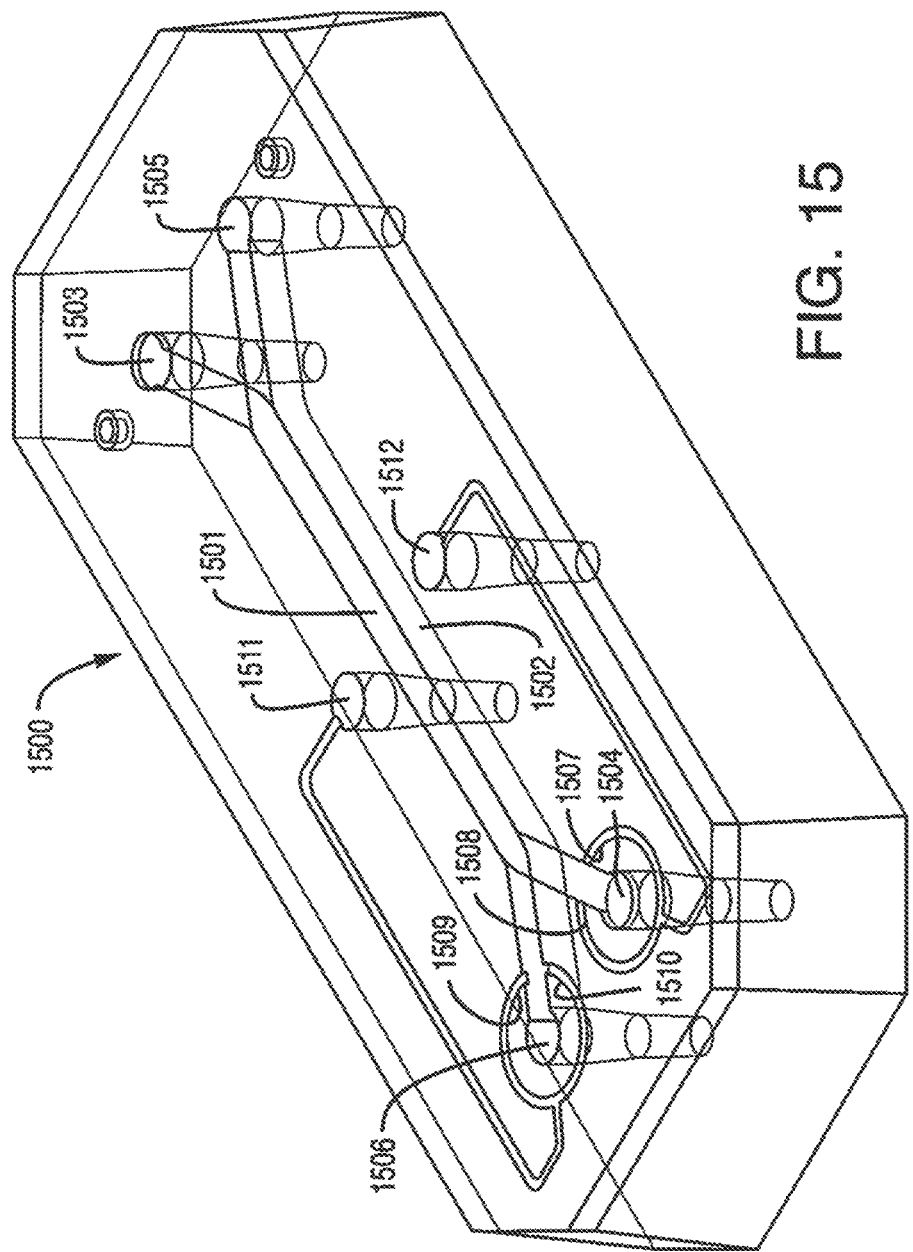
FIG. 15 is a schematic side view of the embodiment of a microfluidic device shown in FIG. 14, where each of two microchannels terminates at a port, each microchannel in fluidic communication with two additive channels (one on either side near the port), each additive channel connecting to a separate port (e.g. for adding the additive).

FIG. 15 is a schematic side view of the embodiment of a microfluidic device 1500 shown in FIG. 14, where each of two microchannels 1501 and 1502 terminates at first and second ports 1504-1506, wherein the first microchannel is in fluidic communication with two additive channels 1507 and 1508 (one on either side just prior to the port), wherein the second microchannel is in fluidic communication with two additive channels 1509 and 1510 (either side near the port), each additive channel connecting to a separate port 1511 and 1512 (e.g. for adding the additive). 1503 and 1505 are sample inlet ports.

Figure 16:
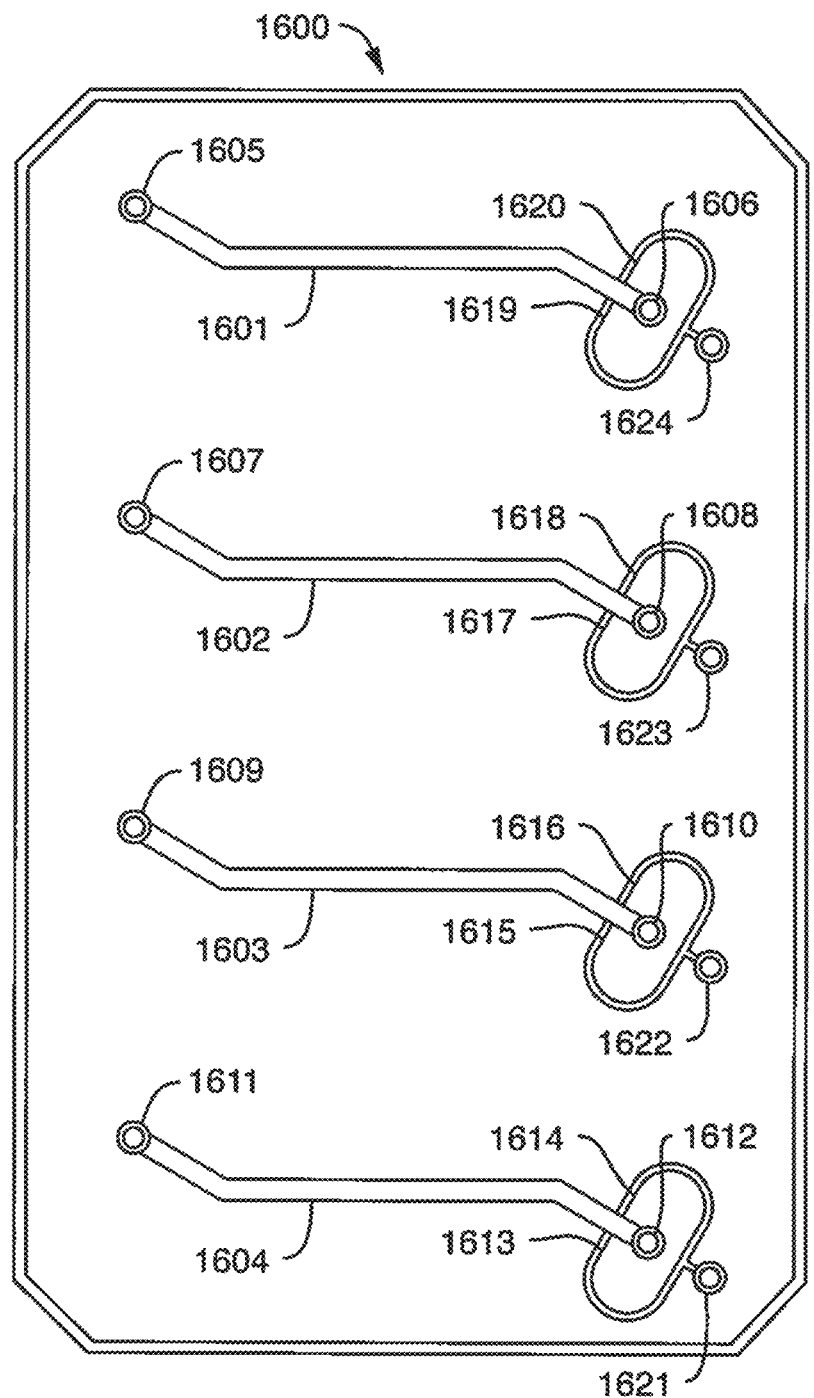
FIG. 16 is a schematic top view of one embodiment of a microfluidic device having four microchannels in parallel, where each end of each microchannel terminates at a port, wherein each microchannel is in fluidic communication with two additive channels (one on either side just prior to the port), each additive channel connecting to separate port (e.g. for adding the additive).

FIG. 16 is a schematic top view of one embodiment of a microfluidic device 1600 having four microchannels 1601-1604 in parallel, where each end of the first microchannel 1601 terminates at first 1605 and second ports 1606, where each end of the second microchannel 1602 terminates at first 1607 and second ports 1608, where each end of the third microchannel 1603 terminates at first 1609 and second ports 1610, where each end of the fourth microchannel 1604 terminates at first 1611 and second ports 1612, wherein each microchannel is in fluidic communication with two additive channels 1613-1620 (one on either side just prior to the port), each additive channel connecting to separate port 1621-1624 (e.g. for adding the additive).

Figure 17:
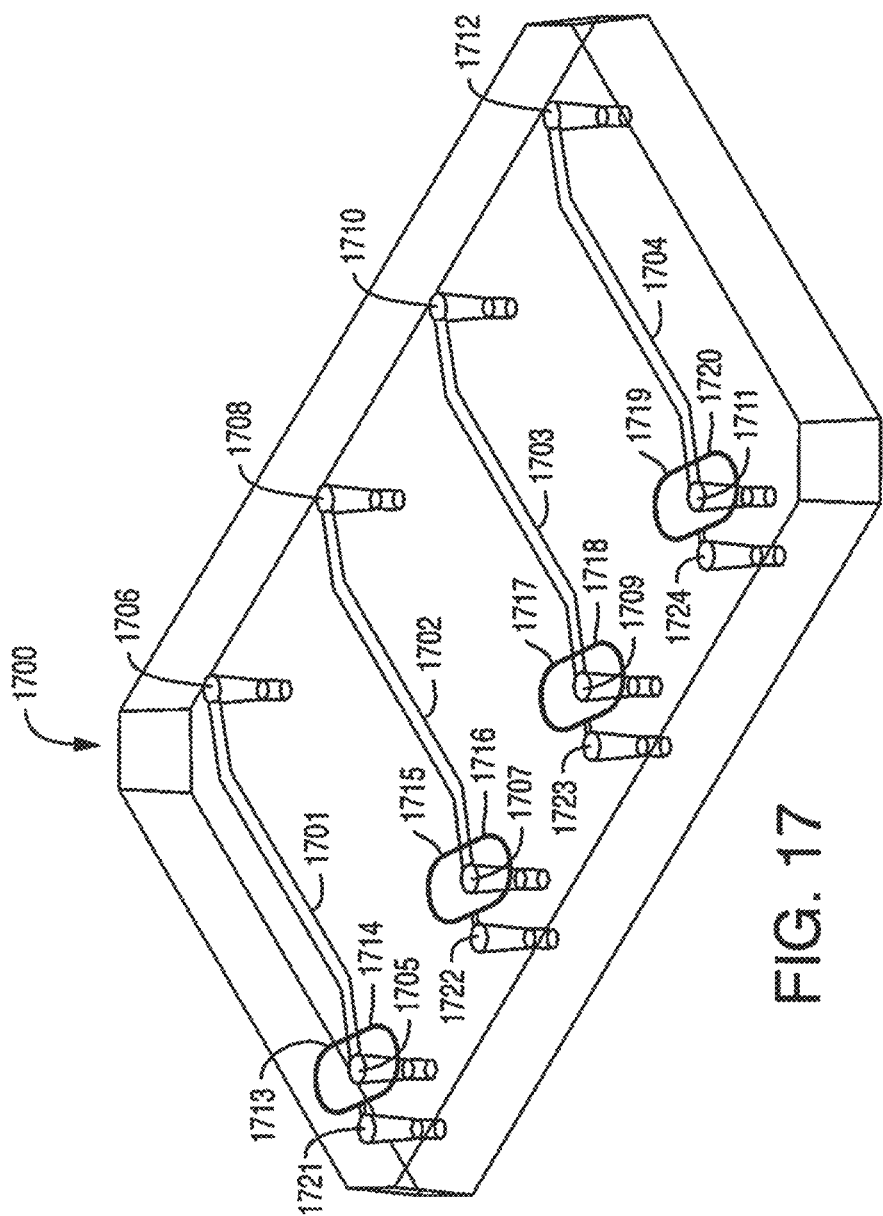
FIG. 17 is a schematic side view of the embodiment of a microfluidic device shown in FIG. 16, where each of four microchannels have first and second ports, wherein each microchannel is in fluidic communication with two additive channels (one on either side just prior to the port), each additive channel connecting to separate port (e.g. for adding the additive).

FIG. 17 is a schematic side view of the embodiment of a microfluidic device 1700 shown in FIG. 16, where each end of the first microchannel 1701 terminates at first 1705 and second ports 1706, where each end of the second microchannel 1702 terminates at first 1707 and second ports 1708, where each end of the third microchannel 1703 terminates at first 1709 and second ports 1710, where each end of the fourth microchannel 1704 terminates at first 1711 and second ports 1712, wherein each microchannel is in fluidic communication with two additive channels 1713-1720 (one on either side just prior to the port), each additive channel connecting to separate port 1721-1724 (e.g. for adding the additive).

Figure 39:
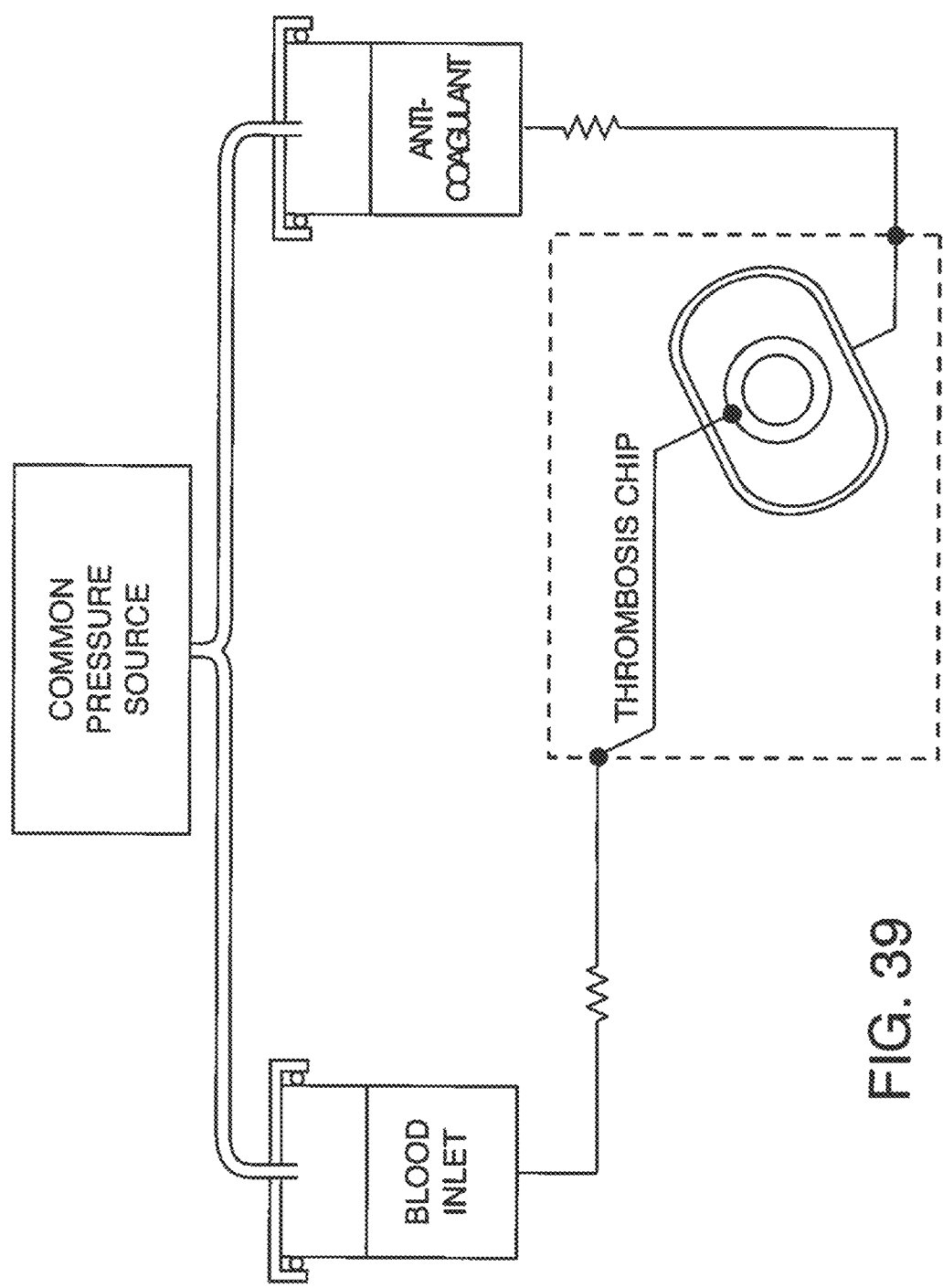
Figure 40C:
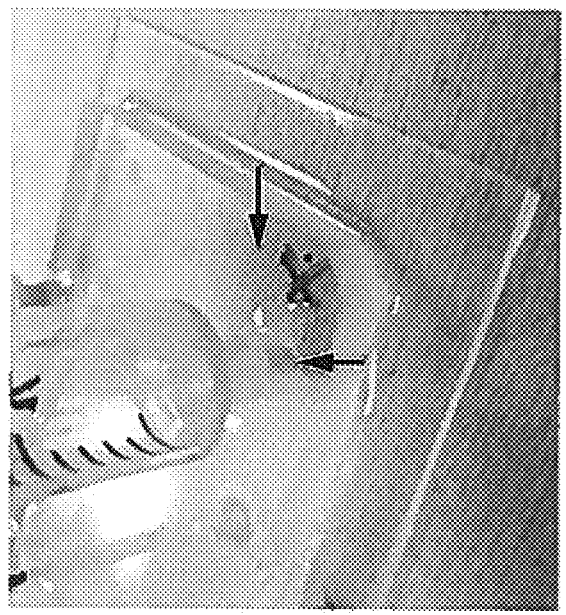
FIGS. 40A-C shows an exemplary photographs of both types of reservoirs, external (as an exemplary syringe) and internal (as on chip), at the blood inlet of a microfluidic chip.
Figure 40A:
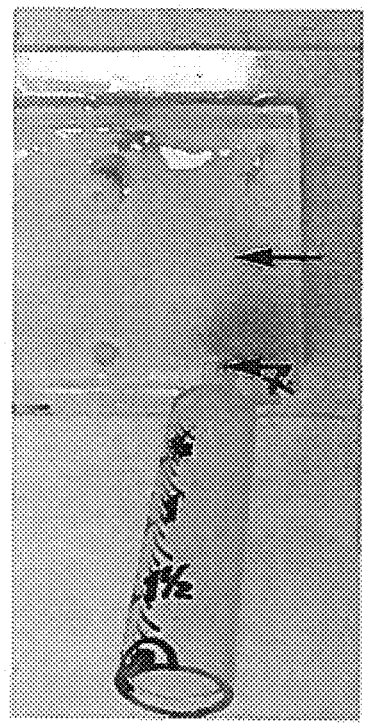
Figure 40B:
Figure 41A:
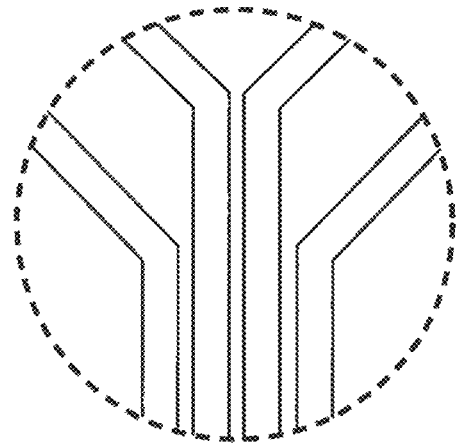
Figure 41B:
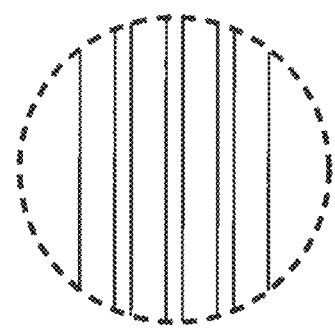
Figure 41C:
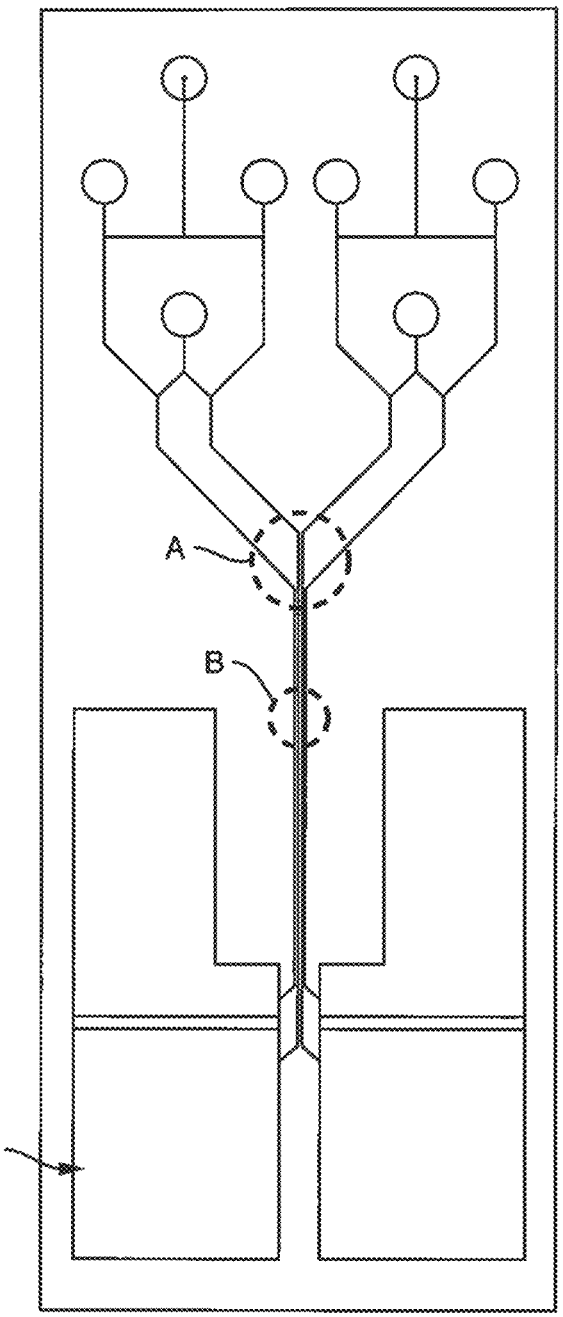
Figure 42C:
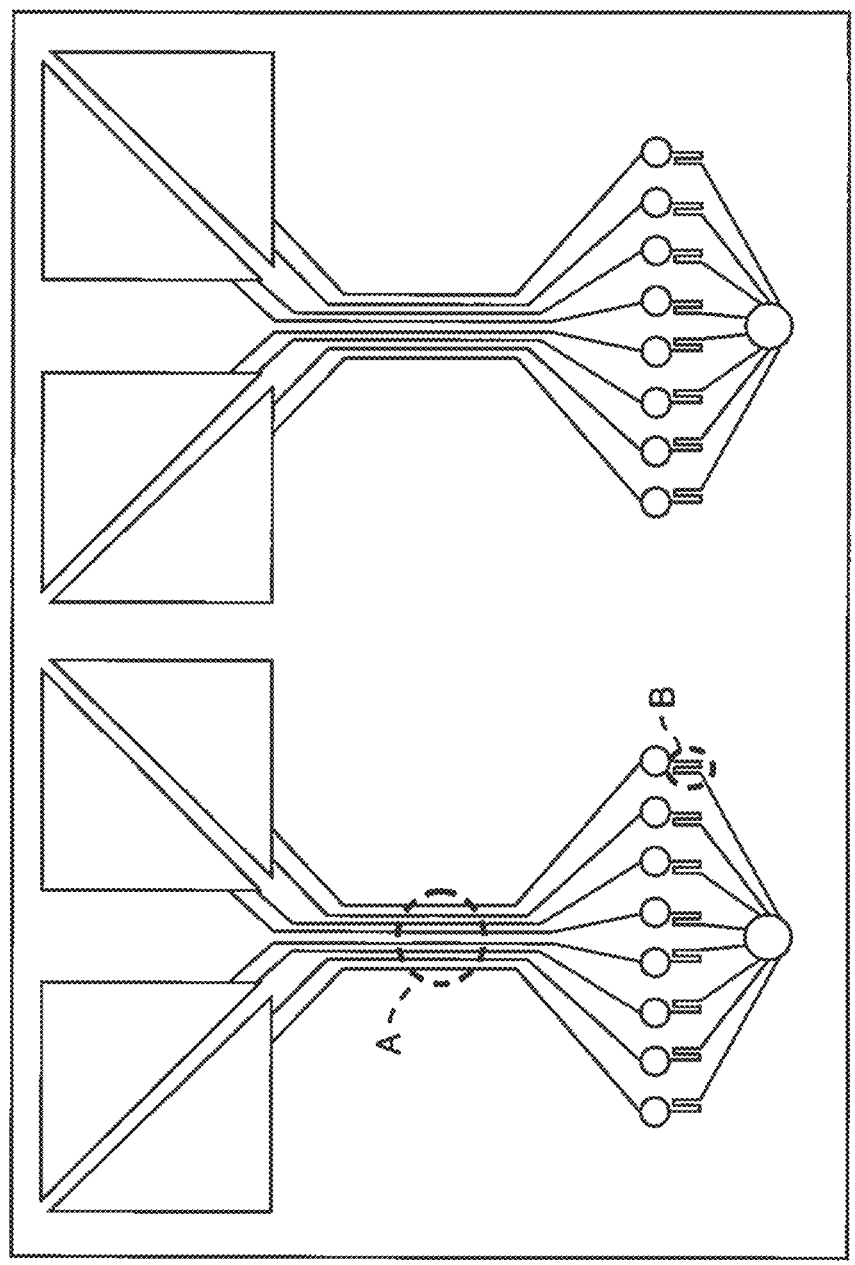
FIGS. 42A-D shows exemplary schematic drawings of one embodiment of a microfluidic chip device demonstrating additional details of some of the components as shown in FIGS. 37 and 38.
Figure 42A:
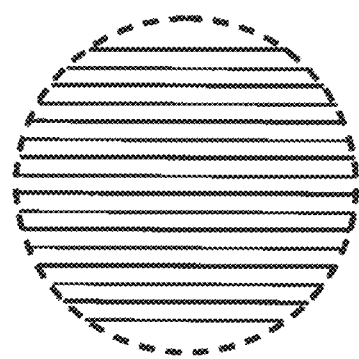
Figure 42B:
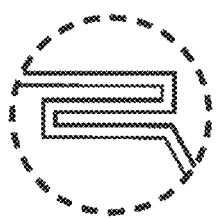
Figure 42D:
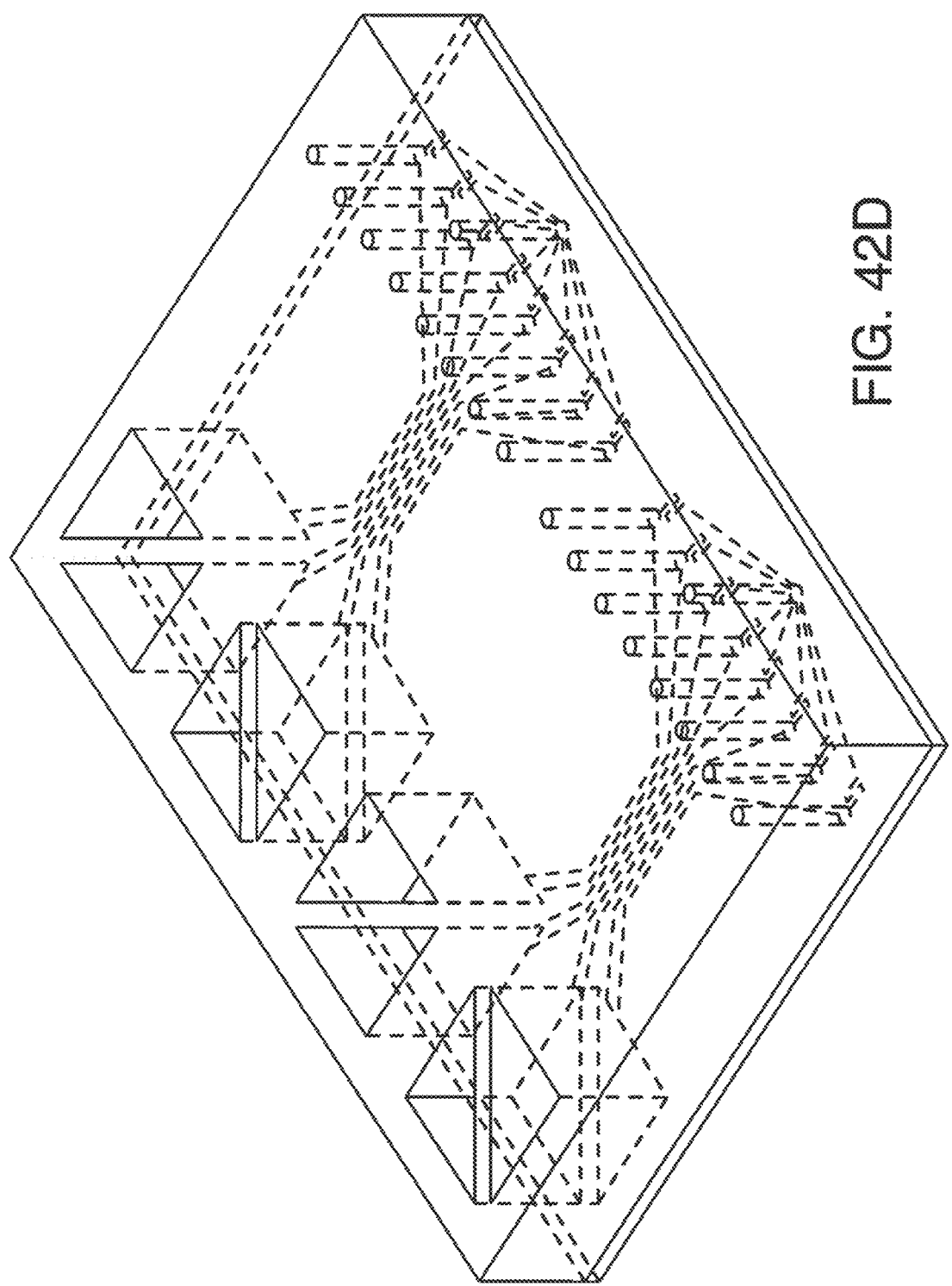

Some of the figures above illustrate a version of the chip with additive channels on one side. This can be the output side or the input side, or both. Were the additive channels are on the output side, this could be used, for example, for adding anticoagulant (e.g. to permit capturing blood that has gone through the chip for downstream analysis, and also for avoiding clot formation in the output, which can lead to clogging and reduced flow). However, the design can be flipped, with similar additive channels on the input side. These may be used, for example, to add calcium to blood (containing anticoagulant) in order render the blood capable of coagulation in preparation for a coagulation-related test or experiment. As one example, see FIG. 39.

Thus, in one embodiment, wherein a microfluidic chip has an upper and lower microchannel, each connected to an inlet port and outlet port, one microchannel may have two "additive channels" located at the termination port (i.e. OUTLET port). However, it is not meant to limit the number of ports (i.e. microchannels) having at least one additive channel.

Indeed, in other embodiments, each outlet port, i.e. each microchannel, may have two "additive channels" located at each of the termination ports (i.e. OUTLET ports), see exemplary embodiments in FIG. 14 and FIG. 15. In one embodiment, wherein a microfluidic chip has an upper and lower channel, one or both microchannels may have two "additive channels" located at the inlet ports. In yet a further embodiment, wherein a microfluidic chip has an upper and lower channel, both channels may have two "additive channels" located at one or both inlet ports and two "additive channels" located at one or both outlet ports, see, FIG. 39.

The presence of additive channels is not limited to microfluidic devices having upper and lower channels. Thus, any sample inlet port may also have additive channels which are in turn connected to one or more input ports. In one embodiment, such additive channels for sample inlets may enable the addition of a de-anticoagulating reagent, e.g. calcium, in addition to other agents for testing in blood flowing through a microfluidic channel towards an outlet port. In yet further embodiments, a microfluidic channel may have additive channels at both the sample inlet port and sample outlet port.

I. Engineering a Microfluidic-Chip Device.

The design of a biomimetic microfluidic-chip device for "on chip" modeling associated with blood as described herein, was made after using previous chamber designs that were found not suitable for perfusion of human blood because, in part, the blood components would immediately begin coagulating as they flowed through tubing, channels, etc. Thus, in order to overcome this limitation, one embodiment of a microfluidic-chip device referred to as a Vessel-On-Chip has at least one or more additive channels that are not part of a previous organ-on-chip designs, as described herein.

Thus, in one embodiment, a microfluidic-chip device comprising two microchannels, one upper channel and one lower channel coated with vascular endothelial cells is referred to as a Vessel On-Chip because it was proven to be suitable for endothelial cell growth and maintaining tissue barrier function. In part, one embodiment of a microfluidic chip design described herein, has a modification of a previous lung-on-chip where the lung-on-chip has a 400 μm chamber, to maximize the contact area existing between endothelial cells and perfused human blood. Thus, in one embodiment of a microfluidic-chip device, the width of the chamber is 1 mm, scaled up from the 400 μm chamber of the lung-on-chip (FIG. 1 and FIG. 2: channels 203) in a Vessel-On-Chip.

Briefly, the microfluidic-chip (200) is made of a transparent elastomer (PDMS) lined with two main microfluidic chambers (203) (FIG. 18A-1 and FIG. 18A-2) separated by a thin porous membrane 208 (FIG. 2). The geometry of the vascular compartment (lower channel in FIG. 18A-1 and FIG. 18A-2) was slightly modified to incorporate an additional anticoagulant port, which is an element used for eluent sampling and downstream analysis of soluble biomarkers as described herein. Notably, while in a lung-on-a-chip design endothelial cells were lining only the lower surface of the porous membrane, here we applied a robust protocol to ensure full surface coverage of the vascular compartment and formation of a whole lumen of human endothelial cells. Within 48 hours post-seeding, endothelial cells formed a confluent monolayer as shown by the expression of intercellular junctional VE-Cadherin (FIG. 18B) covering the entire surface of the chamber. When perfused with cell culture medium, the endothelial cell monolayer remained stable for at least 6 days post-seeding, as confirmed via light microscopy and a vascular permeability assay (FIG. 19A and FIG. 19B).

The internal surface of the microfluidic system was then coated with Type I collagen and fibronectin before seeding human umbilical vein endothelial cells (HUVEC). In some embodiments, collagen is used to coat the walls of the chip for inducing cell attachment. In some embodiments a mixture of collagen and fibrin is used to coat the walls of the chip for inducing cell attachment.

A. Providing a Monolayer of Cells within the Chip Channel.

Cells were seeded in two steps, first onto the bottom surface then onto the apical surface of the vascular chamber to obtain an even distribution of cells along the whole microfluidic channel. Within 48 hours post-seeding, endothelial cells formed a compact monolayer as shown by the expression of intercellular junctional VE-Cadherin (FIG. 18B stained VE-Cadherin), such that a layer of cells are on the internal walls (not just on the membrane) so that every surface has a cell layer covering the entire surface of the chamber. When perfused with cell culture medium, the endothelial cell monolayer remained stable for at least 6 days post-seeding, as confirmed via light microscopy (FIG. 19A) and a vascular permeability assay (FIG. 19B).

B. Characterization of Vessel On-Chip with Activating Factors and an Anti-Platelet Drug: Recapitulating Thrombosis On-Chip.

To test the actual thrombotic activity of our biomimetic vessel-on-chip we perfused freshly isolated human blood through one embodiment of the disclosed system.

Briefly, human blood was drawn in citrate buffer and used within 4 hours. Platelets were stained using fluorescently labeled non-blocking antibodies for the platelet surface marker CD41 and low dosages of fluorescent fibrinogen were added in order to visualize fibrin deposition. Blood was re-calcified in order to re-establish the full coagulation potential, then introduced in the biomimetic vessel-on-chip from the main inlet (embodiments of inlets shown in FIG. 18A-1, FIG. 18A-2 and FIG. 19C). The outlet of the chip was connected to a pulling syringe pump with a system of tubing and connectors made of medical grade silicon that excludes any metal components or potential causes of platelet activation (FIG. 5A).

Figures 2, 18A:
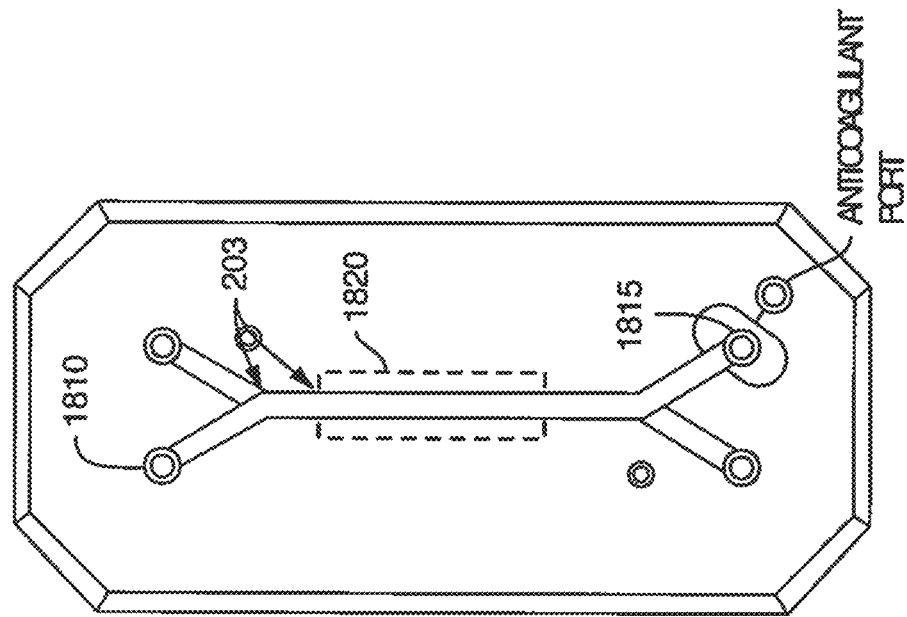
Figures 1, 18A:
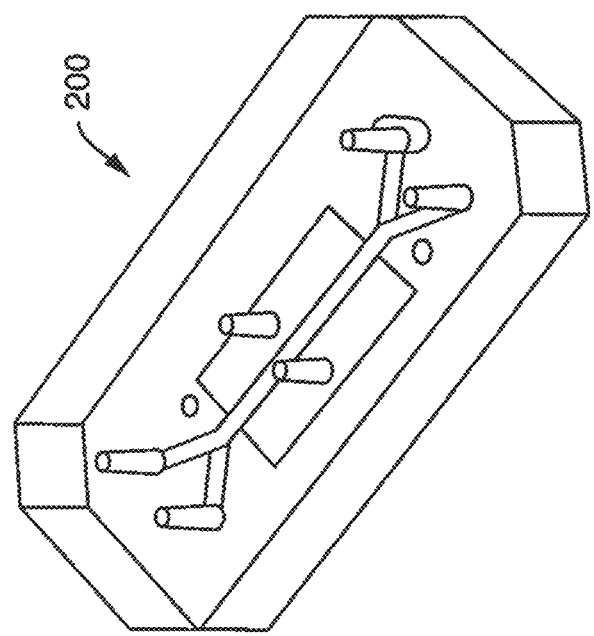
Figure 19A:
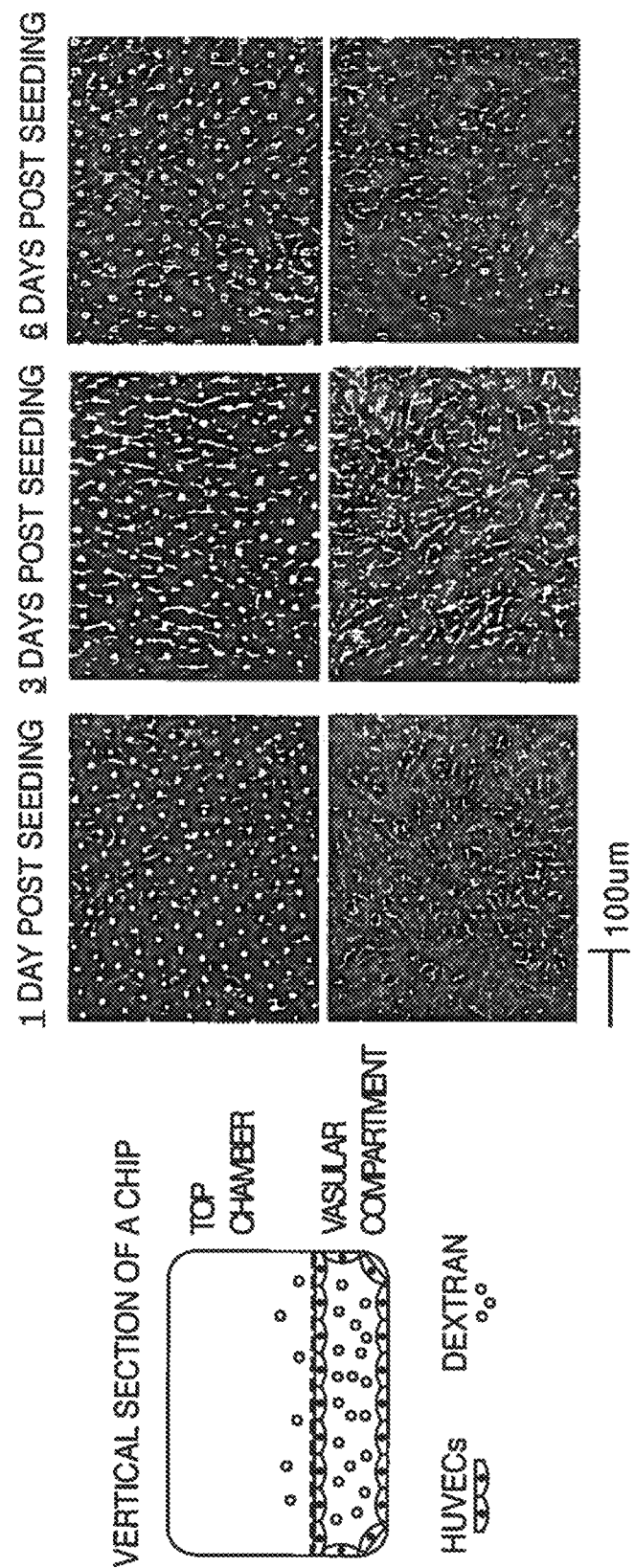
FIGS. 19A-D show schematic illustrations of one embodiment of microfluidic chips as a Thrombosis-On-Chip, micrographs of cells and a chart showing vascular leakage values representing tissue integrity.
Figure 19C:
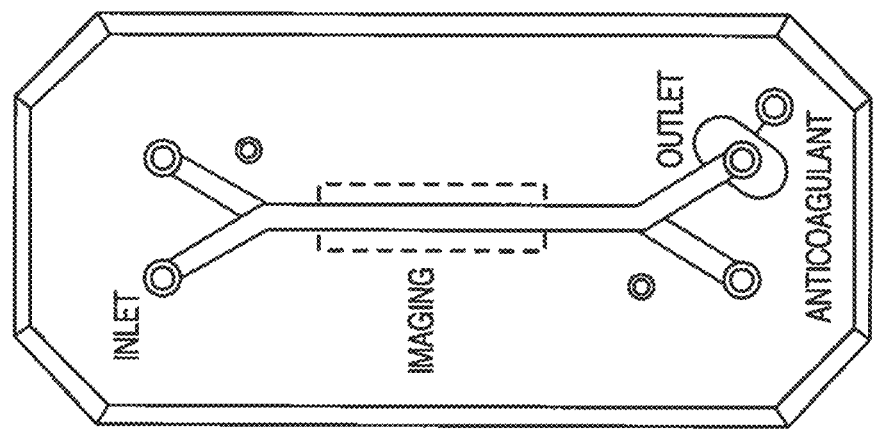
Figure 19B:
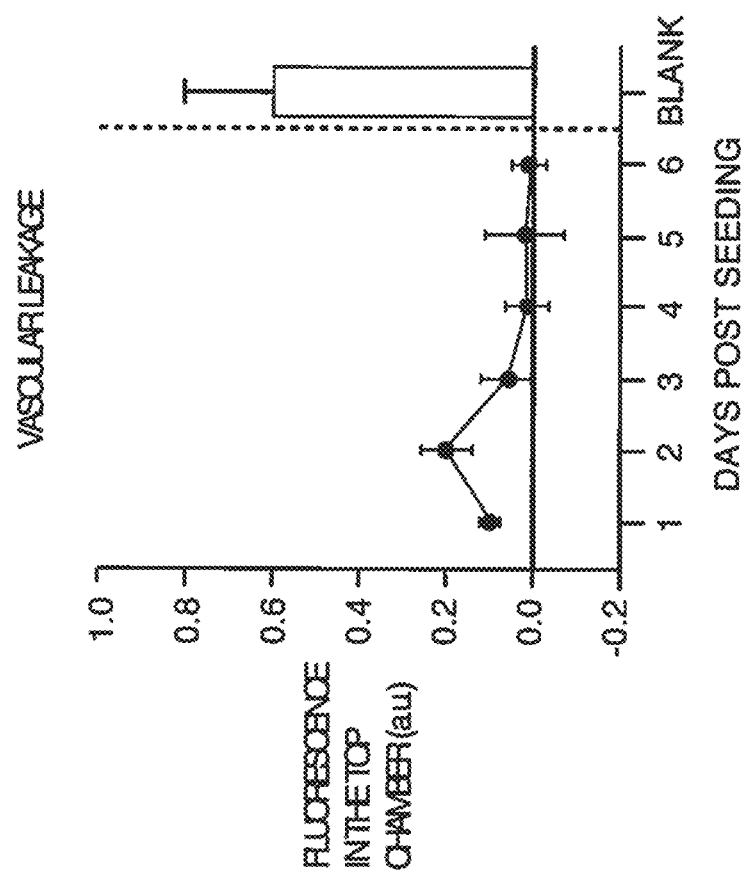
Figure 19D:
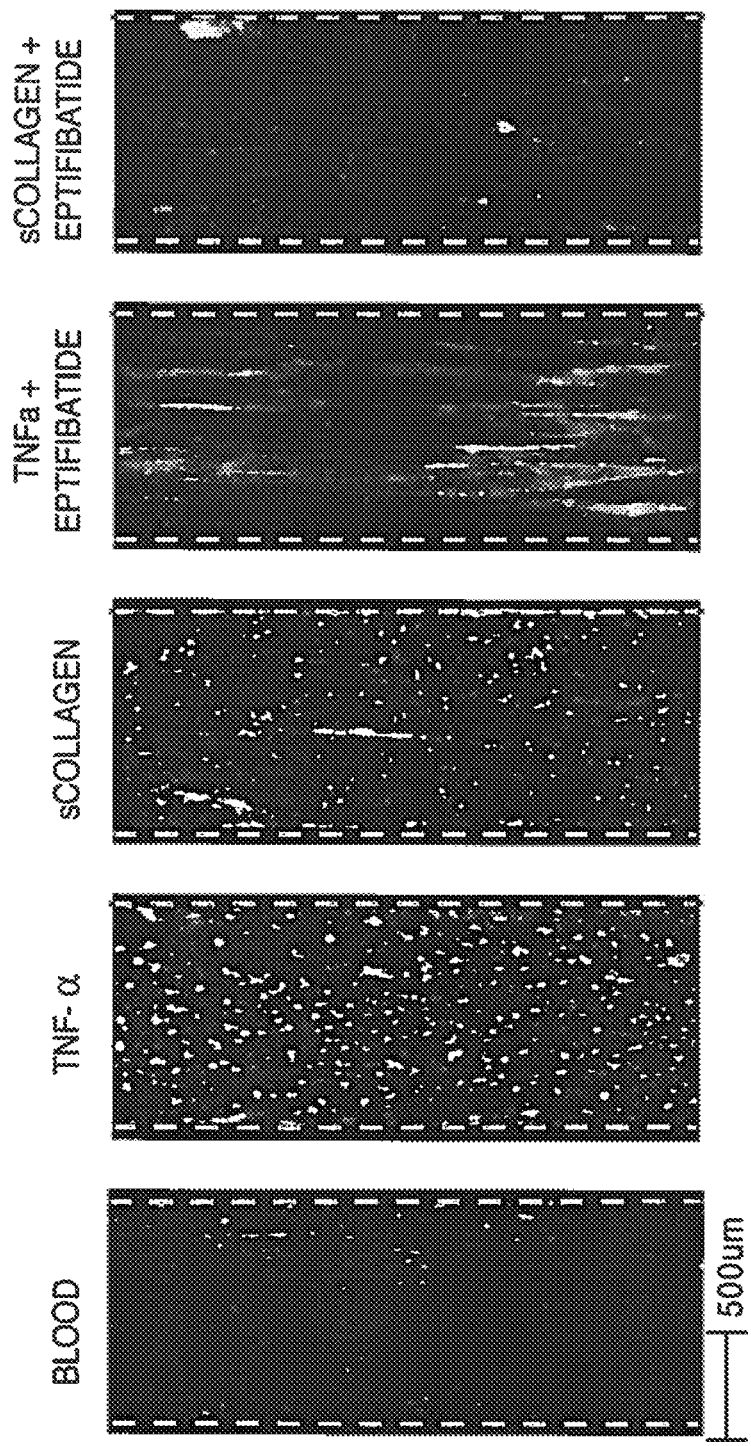

After 14 minutes of perfusion, the flow was interrupted and the chips were immediately imaged via fluorescence microscopy (FIG. 18C and FIG. 19D). In healthy conditions, endothelial cells will provide an antithrombotic surface where blood can flow smoothly, and indeed we detected minimal platelet adhesion or fibrin deposition in our vessel-on-chip after blood perfusion in control conditions, FIG. 18C, Blood.

1. Vascular Endothelium Controls Blood Clotting in a Microfluidic-Chip Device.

Vascular tissue can also act as a signaling platform for different blood cells to be recruited under conditions of tissue inflammation[38]. Previously[35], we used endothelial pre-treatment with Tumor Necrosis Factor-α, to mimic tissue inflammation, inducing expression of factors such as tissue factor, von Willebrand factor, and adhesion molecules associated with coagulation.

For testing on embodiment of a microfluidic-chip device, called a Vessel-On-Chip as described herein, we used endothelial pre-treatment with TNF-α (50 ng/ml, 6 hours) to mimic tissue inflammation, and soluble collagen a standard platelet activator (sCollagen, 10 μg/ml), a standard platelet activator frequently used in vitro and in vivo for other systems[39] to explore how the to explore how the Vessel-On-Chip, as described herein, responded to vascular activation and platelet activation, respectively.

Figures 20A, 20B:
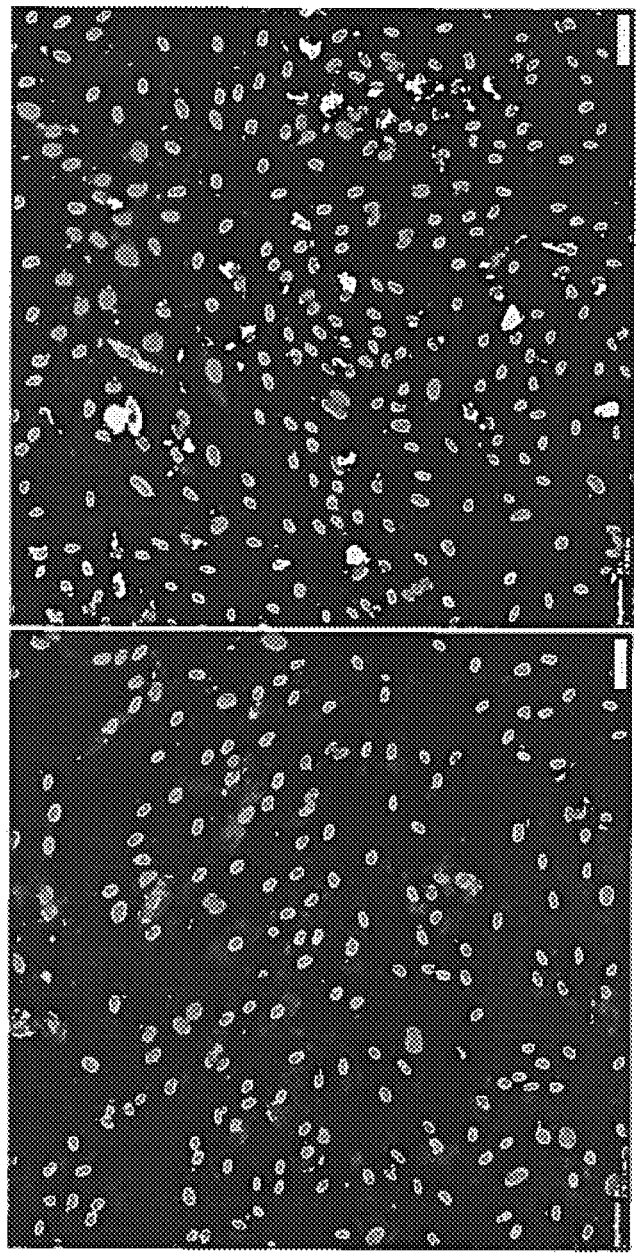
FIGS. 20A-B show exemplary micrographs of endothelium immunostained with anti-ICAM1 antibodies demonstrating exemplary expression of ICAM1 that was higher in TNF-α stimulated endothelium than the control cells.

The inflammation of endothelium by TNF-α was verified by observing increased expression of anti-ICAM1 in the endothelium compared to the control (for example, see FIG. 20). The use of TNF-α or sCollagen treatments on thrombosis in a Vessel-On-Chip led to more aggressive patterns of platelet aggregation and fibrin deposition on the endothelium, as demonstrated by increased areas of platelet coverage and fibrin signal intensity (FIG. 18E-1, and FIG. 18E-2). Diverse structural characteristics of blood clots induced by the two experimental stimuli were captured via scanning electron microscopy (SEM) as colored images in FIG. 18D. In particular, TNF-α pre-treatment of the vascular endothelium induced formation of compact clots composed of red blood cells and platelets, surrounded by fibrin (FIG. 18D, TNF-α.

In contrast, thrombosis by sCollagen involves direct activation of the classic intrinsic coagulation pathway, which leads to general fibrin formation and parallel activation of platelets by binding of sCollagen to their integrin receptor $\alpha 2\beta 1$[41]. Blood incubated with sCollagen formed a meshwork of complex fibrin-rich clots that incorporated red blood cells and platelets FIG. 18D, sCollagen). Additionally, the remarkable alteration of red blood cell morphology (FIG. 18D, sCollagen) is associated with retraction of fibrin during later stages of blood clotting[42,43]. The SEM images provide convincing evidence of de novo formation of fibrin-rich clots in vitro, a relevant pathophysiological endpoint for thrombosis.

These differences are consistent with the mechanism for thrombosis by both agents, i.e. thrombosis by TNF-α is primarily driven by activation of the endothelium and release of factors that promote adhesion and platelet-to-platelet interactions which then leads to local thrombin activation, fibrin formation and clot stabilization 40.

2. Testing Anti-Coagulation Compounds in a Vessel-On-Chip.

In order to continue a functional characterization of our thrombosis model, we challenged the two main pro-thrombotic conditions (TNF-α and sCollagen) using Eptifibatide. Eptifibatide refers to a small cyclic heptapeptide capable of blocking platelet aggregation by mimicking the active residue of fibrin involved in platelet aggregation during blood clotting, thus inhibiting integrin $\alpha IIb/\beta III$[34], the endogenous platelet receptor for fibrinogen. Eptifibatide was approved by the Food and Drug Administration (FDA). When used in a Vessel-On-Chip at a clinically relevant concentration of 2 ug/ml,[44] it significantly inhibited platelet aggregation and fibrin clot formation when the endothelium was inflamed with TNF-α, but its inhibitory effect was modest following treatment with sCollagen (FIG. 18E, n=4). Image analysis of multiple experiments (FIG. 18E, n=4) revealed that platelet adhesion was completely inhibited but a significant amount of fibrin signal was still detectable in samples treated with TNF-α (FIG. 19D), suggesting that fibrin deposition over an inflamed endothelium might happen independently from platelet aggregation. This finding is consistent with the mechanism of action of sCollagen, which binds to a different platelet integrin receptor and which stimulates coagulation via the platelet-independent intrinsic pathway.

Figure 18B:
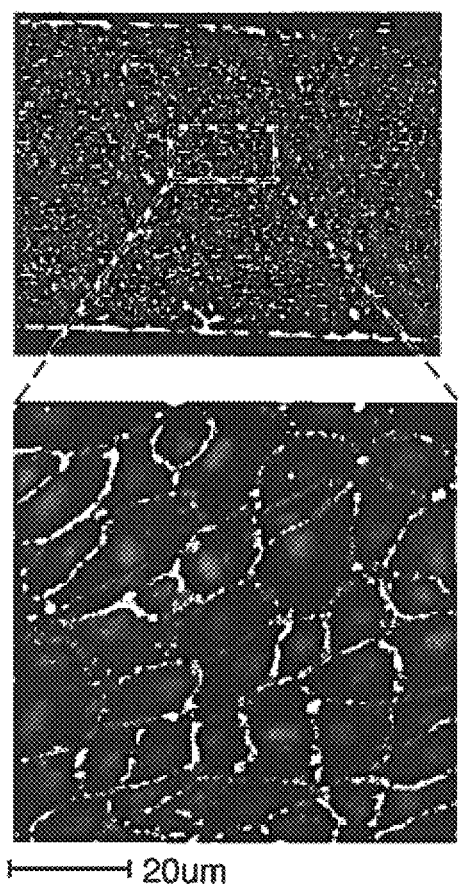
Figures 1, 2, 18E:
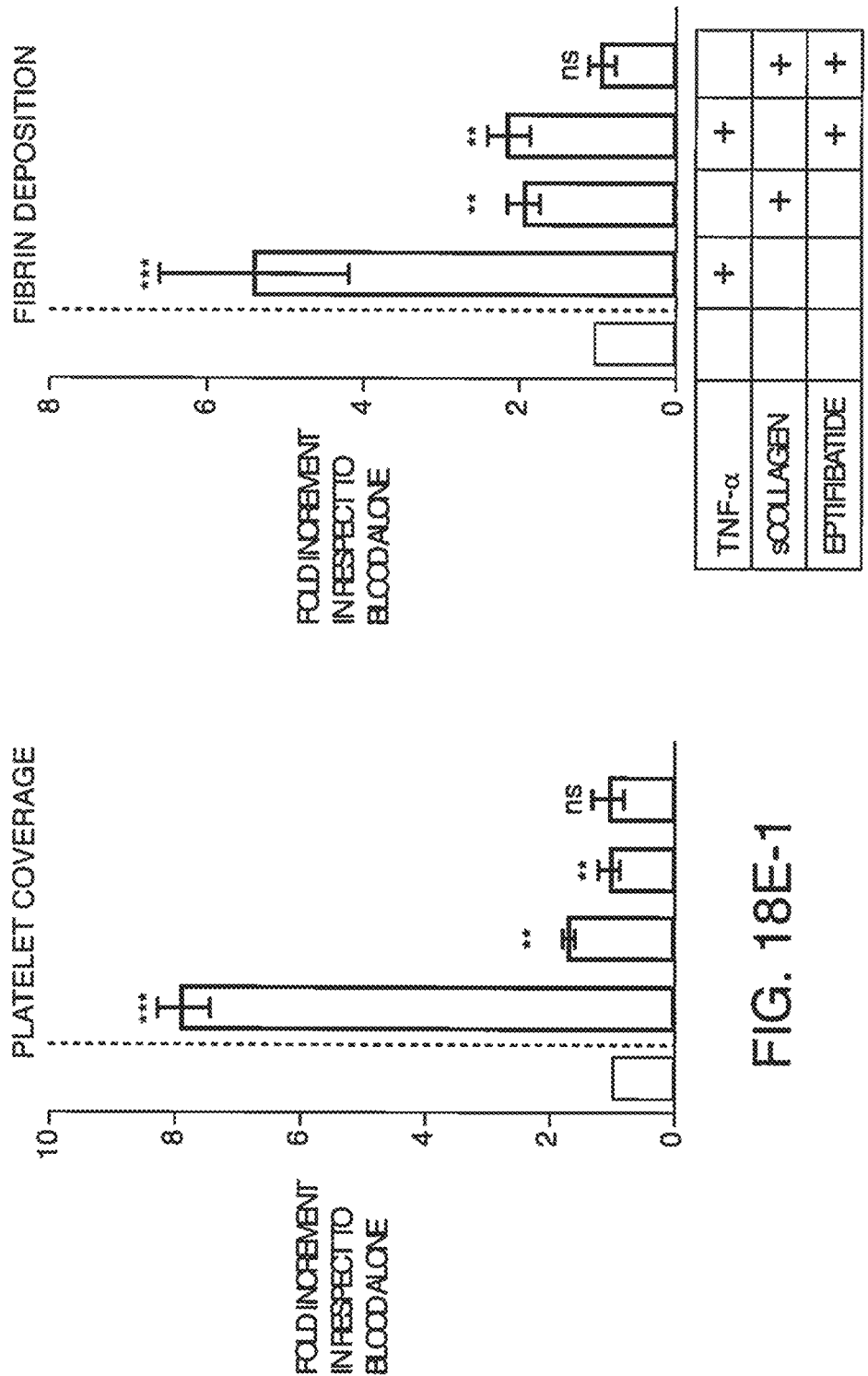

FIGS. 18A1-A2 through FIGS. 18E-1 and FIGS. 18E-2 demonstrates one embodiment of On-chip reconstitution of thrombosis showing schematic illustrations of an exemplary embodiment for a microfluidic-chip, micrographs of cells and charts comparing blood clotting events induced by several compounds. FIG. 18A-1, schematic representation of one embodiment as a Thrombosis-On-Chip (200). FIG. 18A-2 schematic representation of the chip (200) showing the main features: inlet port (1810), main channel and imaged area (1820), outlet port (1815), and the on-chip anticoagulant port. FIG. 18B Top, endothelial morphology by fluorescent VE-cadherin staining (stain as white lines). Bottom, high magnification section of endothelial cells stained for VE-cadherin. FIG. 18C shows that under control conditions (whole blood alone) platelets and fibrin shown as white spots and line, are sparse and detectable at the edge of the imaged areas. Endothelial exposure to TNF-α or pre-incubation of blood with soluble collagen (sCollagen) led to formation of a high number of larger aggregates containing a platelet rich core decorated with fibrin. FIG. 18D shows scanning electron micrographs of cells showing typical ultrastructure of blood clots formed on-chip, in control conditions ('Blood') the sparse platelets are dispersed on an endothelial surface, in stimulated conditions ('TNF-α' and 'sCollagen') activated platelet aggregates and fibrin networks with trapped red blood cells are attached to an endothelial cell surface. FIG. 18E-1 and FIG. 18E-2 shows charts showing FIG. 18E-1 platelet coverage and FIG. 18E-2 fibrin deposition (both charts using the lower treatment key shown in FIG. 18E-2) that were significantly increased in stimulated Platelet coverage, fibrin deposition were significantly increased in stimulated, pro-thrombotic conditions in multiple donors (n=4, S.E.M., * p<0.05, ns=not significant), and the effects were suppressed by adding the drug Eptifibatide. Overall, there is a highly significant difference between the TNF-alpha treated with and without Eptifibatide and between sCollagen treatment with and without Eptifibatide.

3. On-Chip Anti-Coagulation Allows Sampling of Outflowing Blood: Vessel-On-Chip Biomarker Assessment.

Microfluidic chambers were described as models of thrombosis ((Tsai, et al., In vitro modeling of the microvascular occlusion and thrombosis that occur in hematologic diseases using microfluidic technology. *J. Clin. Invest.* 122: 408-418 (2012); Neeves, et al., The use of microfluidics in hemostasis: clinical diagnostics and biomimetic models of vascular injury. *Curr. Opin. Hematol.* 20:417-423 (2013); Westein, et al., Atherosclerotic geometries exacerbate pathological thrombus formation poststenosis in a von Willebrand factor-dependent manner. *Proc. Natl. Acad Sci. U.S.A* 110: 1357-1362 (2013); Westein, et al., Monitoring in vitro thrombus formation with novel microfluidic devices. *Platelets* 23:501-509 (2012), including endothelium (Branchford, et al., Microfluidic technology as an emerging clinical tool to evaluate thrombosis and hemostasis. *Thromb. Res.* 136: 13-19 (2015); Li, et al., Microfluidic Thrombosis under Multiple Shear Rates and Antiplatelet Therapy Doses. *PLoS ONE* 9:e82493 (2014)) and using imaging as the functional readout to study blood clotting. Furthermore, because blood eventually coagulates inside system components and tubing, eluent sampling from microfluidic chambers becomes virtually impossible. In fact, once blood coagulates in any of these published microfluidic chambers, the cells become virtually inaccessible and sampling of outflowing blood typically is not possible. Thus, even though inclusion of biomarkers of coagulation to complement functional imaging readouts of platelet function is desired, the large amount of uncontrolled coagulation prevents this type of analysis. In other words, blood eventually coagulates inside system components and tubing, eluent sampling from the on-chip vessel becomes virtually impossible.

Figures 22A, 22B:
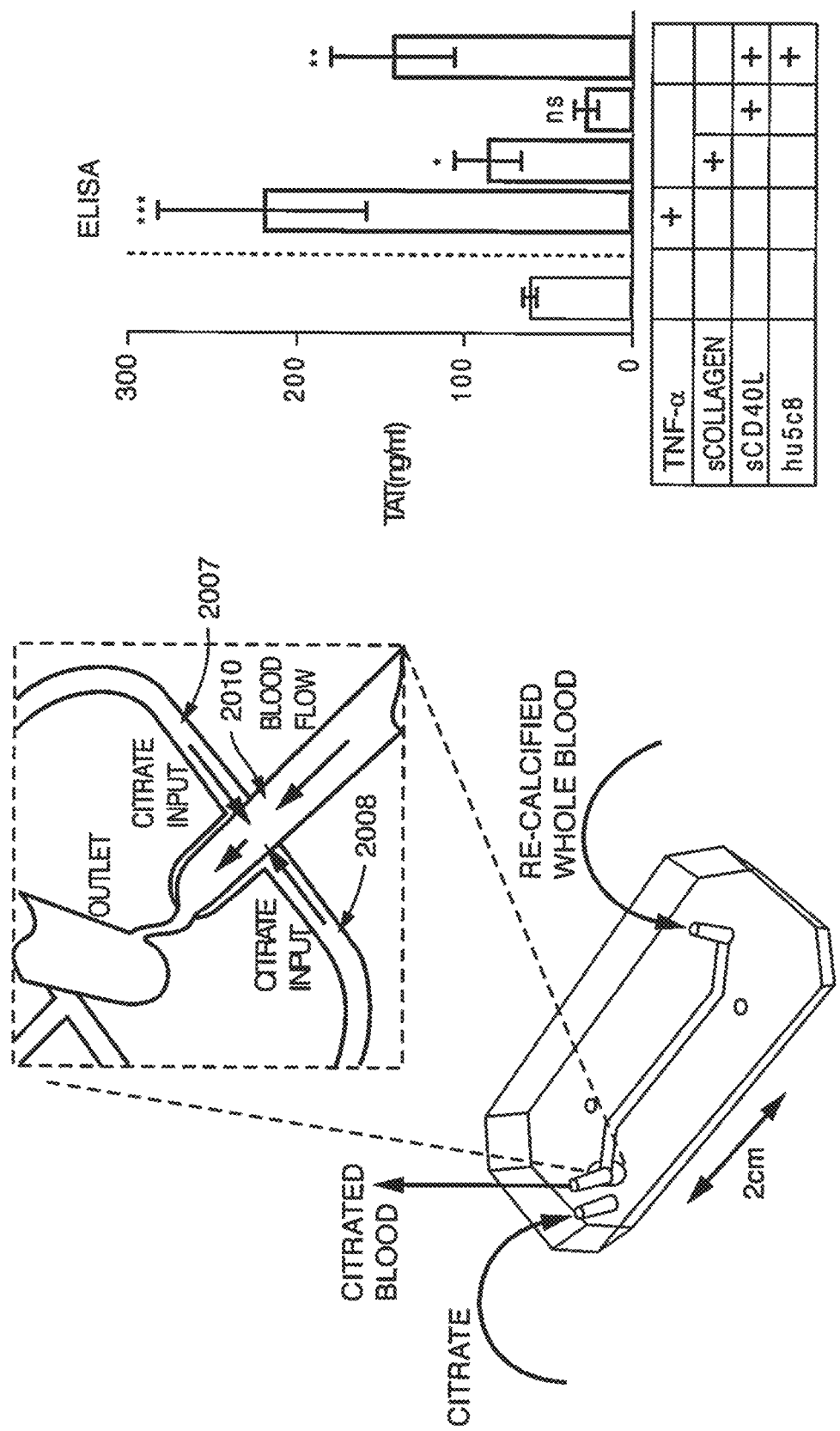
FIGS. 22A-B show one embodiment of a Vessel-On-Chip, where out-flowing blood allows sampling and analysis of effluent in addition to a chart demonstrating comparative TAT levels following several different treatments.

Aiming to overcome these limitations of previous microfluidic devices, we added at least a third microfluidic channel (i.e. an additive channel) to the outflow port of a chip, forming one embodiment of an On-Chip device, alternatively a microfluidic chip device, where anticoagulants, e.g. sodium citrate or EDTA, are introduced through input channels and are mixed with blood upon flowing out of the microfluidic chip (embodiments illustrated in FIG. 12, FIG. 18A-2; FIG. 19C; FIG. 22A), for exemplary embodiments of a microfluidic On-Chip device. Thus, a microfluidic On-Chip device is contemplated to provide a stable platform for assessment of thrombosis.

In order to functionally test the system, re-calcified blood was perfused through the inlet while anticoagulant, e.g. citrate buffer, was introduced online from the port situated next to the outflow port. Thus, blood obtained from the effluent of chips equipped with the anticoagulant port or without anticoagulant port were compared (FIG. 6). From a qualitative point of view the difference was striking. Introduction of sodium citrate through the anticoagulant port allowed for collection of soluble (not clotted) blood at the end of each experiment that remained in the liquid status (FIG. 6).

Thrombin converts fibrinogen into fibrin during clot formation, and anti-thrombin plays a role in maintaining homeostasis by inhibiting the effect of thrombin. Formation of TAT in the microdevice confirms that local and intrinsic generation of thrombin, a potent platelet agonist, occurs in the model and that counter regulatory mechanisms for coagulation are retained. Thus, blood sampled from the Vessel-On-Chip was analyzed for thrombin anti-thrombin complex (TAT), an accepted clinical biomarker for procoagulation[48,49]. TAT refers to a factor released upon activation of the coagulation cascade and one of the biomarkers associated with thrombotic events occurring in patients affected with deep vein thrombosis (DVT) or Systemic lupus erythematosus (SLE)[45,46]. An enzyme-linked immunosorbant assay (ELISA) was used to quantify the thrombin anti-thrombin complex (TAT).

Figure 23:
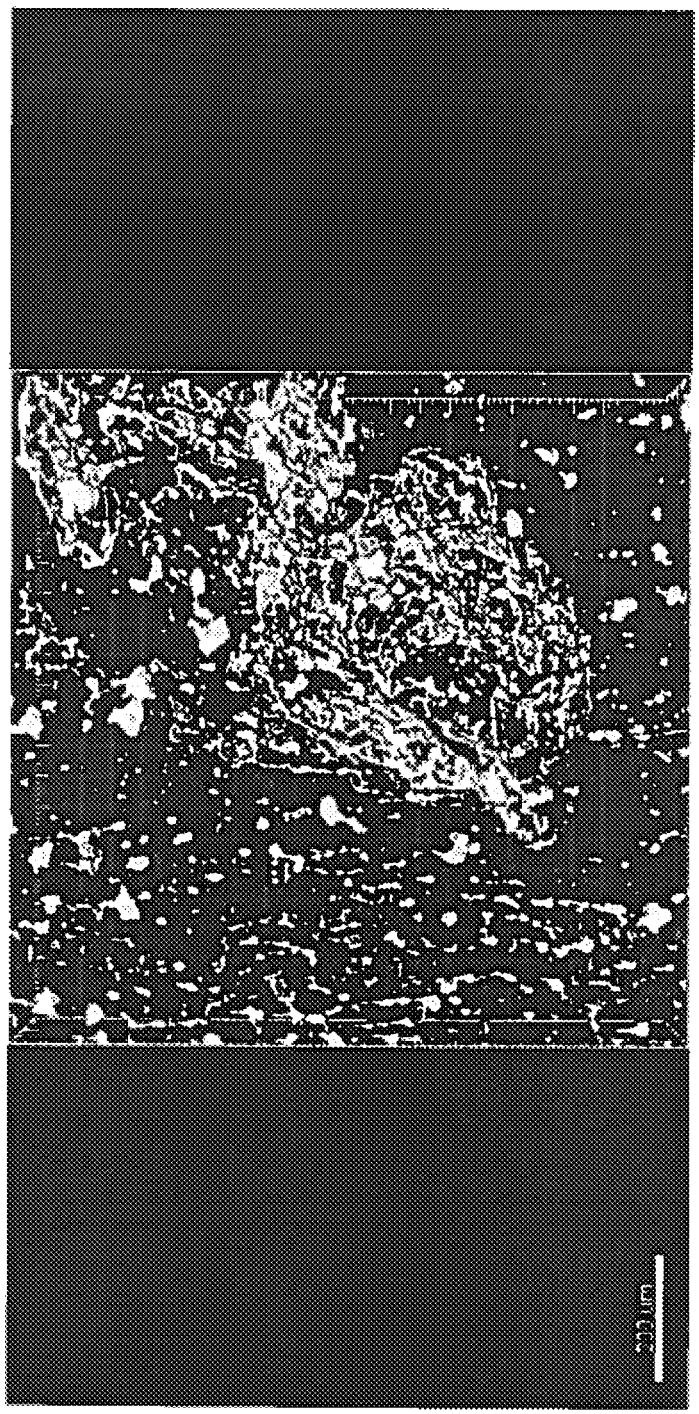
FIG. 23 shows an exemplary micrograph obtained from a movie demonstrating 3D reconstruction of IC-induced Clot on Chip. A typical blood clot induced by IC5c8 treatment includes nucleate cells and microthrombi (with platelets) trapped within the fibrin meshwork. When this figure is in color: nucleate cells are DAPI stained colored purple; fibrin is colored cyan and platelets are colored yellow.

We discovered that levels of TAT (FIG. 22B) were significantly increased following treatment with TNF-α or combined hu5C8/sCD40L, and minimally increased with sCollagen, demonstrating a good correlation with the imaging endpoints described herein. Furthermore, a 3D movie captured the formation of a blood clot induced by IC5c8 treatment as microthrombi trapped within a fibrin meshwork including platelets and nucleate cells (DAPI staining). A still image of an induced clot in the Vessel-On-Chip is shown in FIG. 23.

Figure 24:
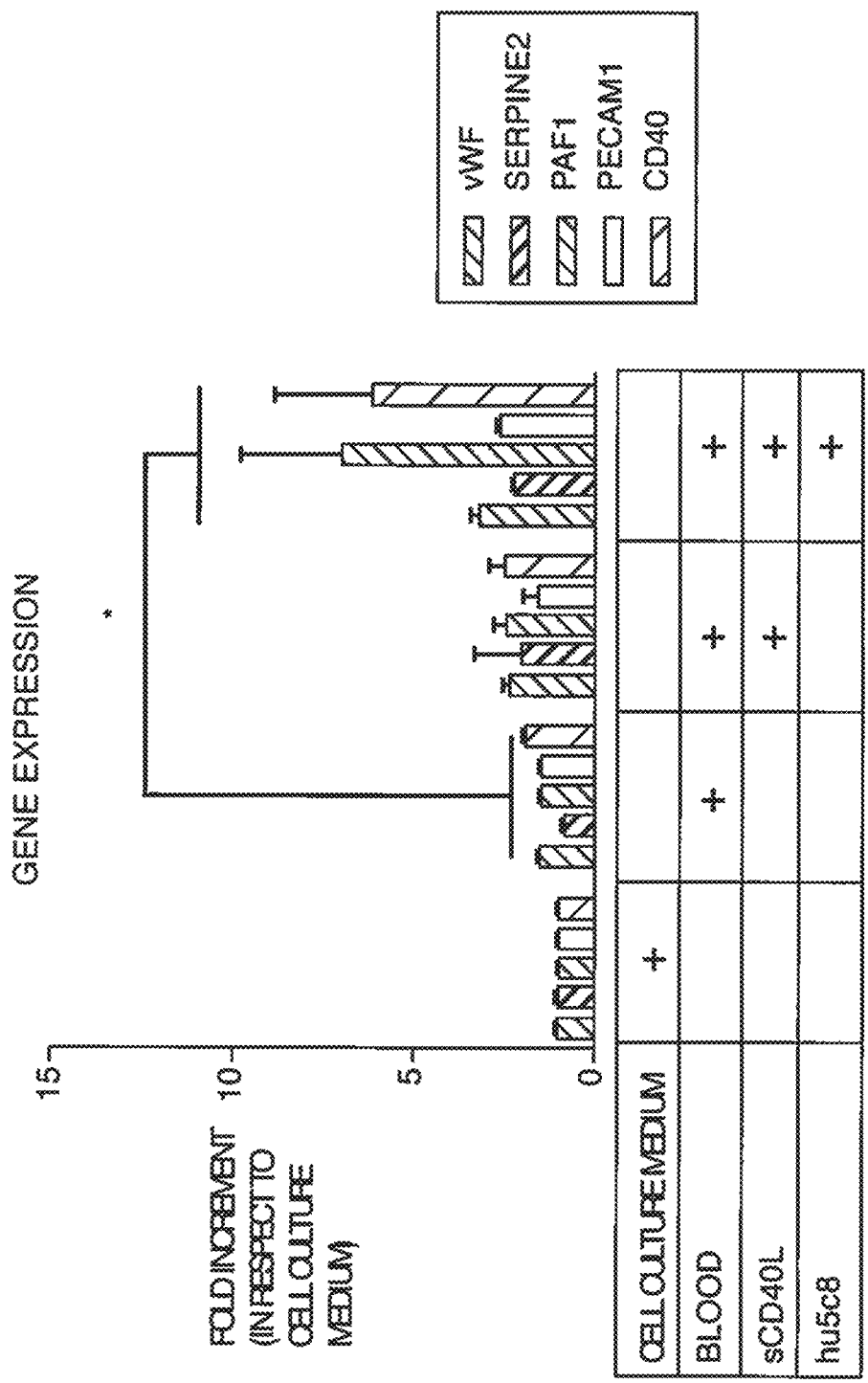
FIG. 24 shows a chart comparing gene expression data obtained from chips treated with blood alone or in combination with sCD40L and hu5c8 and normalized in respect to cells perfused with standard cell culture medium. In particular, PAF1 (polymerase associated factor) and CD40 show higher expression in blood treated with sCD40L and hu5c8 treated blood. Other genes measured included vWF (Von Willebrand Factor), SERPINE2 (Serpin Family E Member 2), and PECAM1 (Platelet And Endothelial Cell Adhesion Molecule I).

In addition to anti-thrombin, evidenced by TAT formation, mRNA levels of the SERPINE class of inhibitors of blood coagulation proteases, plasminogen activator inhibitor −1 (PA1-1) and SERPINE-2 (Serpin Family E Member 2), were increased 8- and 2-fold, respectively (FIG. 24). There were no observed changes in D-dimer in eluates from blood treated with hu5C8/sCD40L combined, suggesting that the rate of procoagulation exceeded fibrinolysis in the assay conditions or that longer incubation times may be required to observe formation of fibrinolytic products.

Levels of TAT were increased following endothelial pre-treatment with TNF-α or when blood was activated with sCollagen, showing a good correlation with the imaging endpoints described above.

Surprisingly, Eptifibatide treatment did not inhibit the TAT increment associated with TNF-α-induced inflammation while it entirely suppressed the TAT increment due to sCollagen treatment. Apparently, the biochemical pathway leading from TNF-α-induced vascular inflammation to activation of the coagulation cascade is independent of platelet aggregation as shown on the disclosed microfluidic chip device (in one embodiment, as a Thrombosis-On-Chip) which recapitulated the phenomena.

We conclude that the biomimetic Vessel-On-Chip (as a Thrombosis-On-Chip) allows for both qualitative and quantitative assessment of events characterizing blood clotting. The system is indeed able to recapitulate clinically relevant aspects of thrombosis including platelet adhesion, aggregation, fibrin deposition and release of biomarkers of procoagulation, such as TAT, in addition to characterizing blood clotting. Thus, a microfluidic chip device as described herein, provides a unique capability to study real time thrombotic events in microphysiological system.

4. In Vivo Thrombosis Induced by Hu5C8, a Candidate Therapeutic Monoclonal Antibody, is Mimicked In Vitro by Preformed $IC_{5c8}$.

Once the robustness of the biomimetic Vessel-on-chip was established, in part as defined endpoints for thrombosis measurements as shown herein, we used the system to study the pro-thrombotic effects of the anti-sCD40L monoclonal antibody, hu5c8. Hu5c8 (Ruplizumab) refers to a humanized monoclonal IgG1 antibody against CD40L alternatively named anti-sCD40L or anti-CD154. Hu5c8 blocks the interaction of CD40 with its ligand CD154 (CD40L) thus blocking T-cell: B-cell interactions in antibody mediated autoimmune disorders, such as systemic lupus erythematosus (SLE) where it was tested in a clinical trial. However, CD40L is rapidly expressed on the surface of platelets and is released in a soluble form after platelet activation and thrombus formation.

Several human clinical trials with the immunosuppressant antibody-based drug, hu5C8, were terminated due to unexpected thrombosis and cardiovascular events in patients. These life-threatening side-effects were not discovered during preclinical testing due to the lack of predictive assays. Here we show that a biomimetic vessel on-chip can detect the thrombotic effects of hu5C8. The vessel-on-chip contains microcultures of human endothelium and flowing human whole blood, and it recapitulates complex endpoints for thrombosis, including endothelial activation, platelet adhesion, platelet aggregation, fibrin clot formation and expression of clinically relevant biomarkers. The data produced with our on-chip system is consistent with data from the clinic and other human-relevant tests, highlighting the major significance of this on-chip assay for future preclinical evaluation of drug candidates.

Platelet activation assays conducted to study thrombosis risk for this molecule typically use optimized but not clinically relevant stoichiometric ratios of hu5C8 and sCD40L to generate high-ordered immune complexes (ICs), which is useful for mechanistic studies, but less relevant for assessment of risk for clinical use. Further, based on previous studies, hu5C8 is able to bind the trimeric form of sCD40L in a non clinically relevant 3 to 1 stoichiometric ratio to form ICs ($IC_{5c8}$) that ultimately cause rapid platelet activation (illustrated in FIG. 25A).[12,21]

We investigated whether Hu5C8 added to a biomimetic Vessel-On-Chip would be able to recapitulate the thrombotic events associated with the anti-CD154 mAb hu5C8. We leveraged the physiological realism of a Vessel-On-Chip so we tested physiologically relevant concentrations of an $IC_{5c8}$ preparation made with a ratio of 30,000:1 at clinically relevant doses of hu5C8 (240 μg/ml)[47], benchmarked to a dose of 20 mg/kg in cynomolgus monkey, to determine whether we could produce a detectable thrombotic effect on the biomimetic vessel. This is the same dose in humans that caused thrombosis[28]. We also used disease relevant concentrations of sCD40L (10 ng/ml), which are typical values reported in human lupus patients (Kato, et al. "The soluble CD40 ligand sCD154 in systemic lupus erythematosus." *Journal of Clinical Investigation.* 104(7):947-955, 1999).

Blood alone or blood treated with hu5C8 alone (240 µg/mL), sCD40L (10 ng/ml) alone or with combined hu5C8/sCD40L from 4 donors was processed and perfused through the biomimetic vessel at a flow rate of 60 µl/minute, which yields a wall shear stress (0.5 Pa, 5 dyne/cm$^2$) comparable to values found in veins under physiological conditions[47].

Figure 21C:
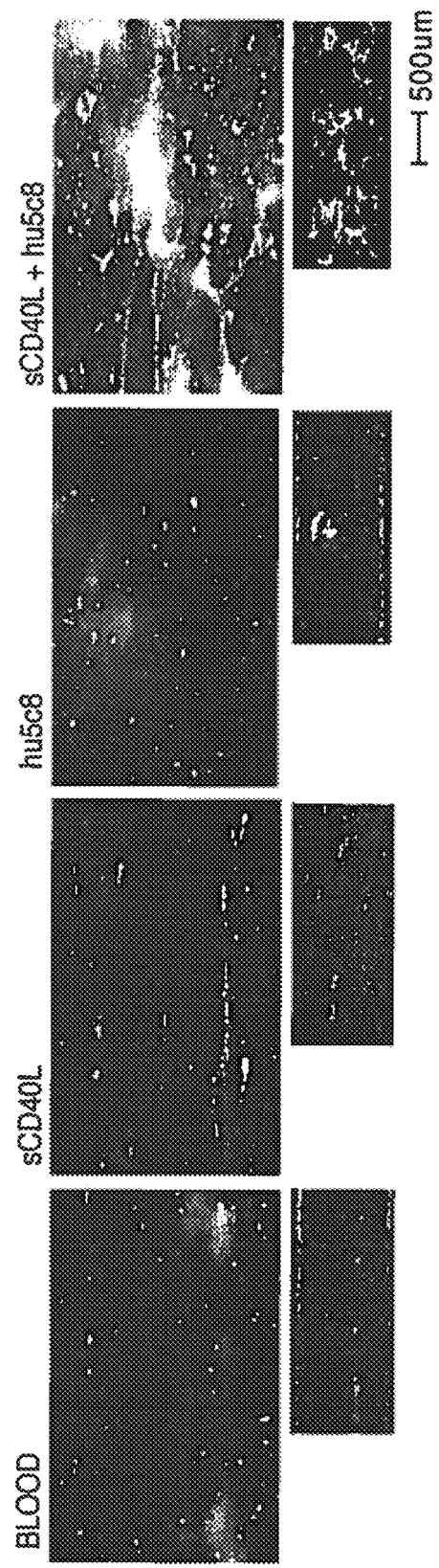
Figure 21D:
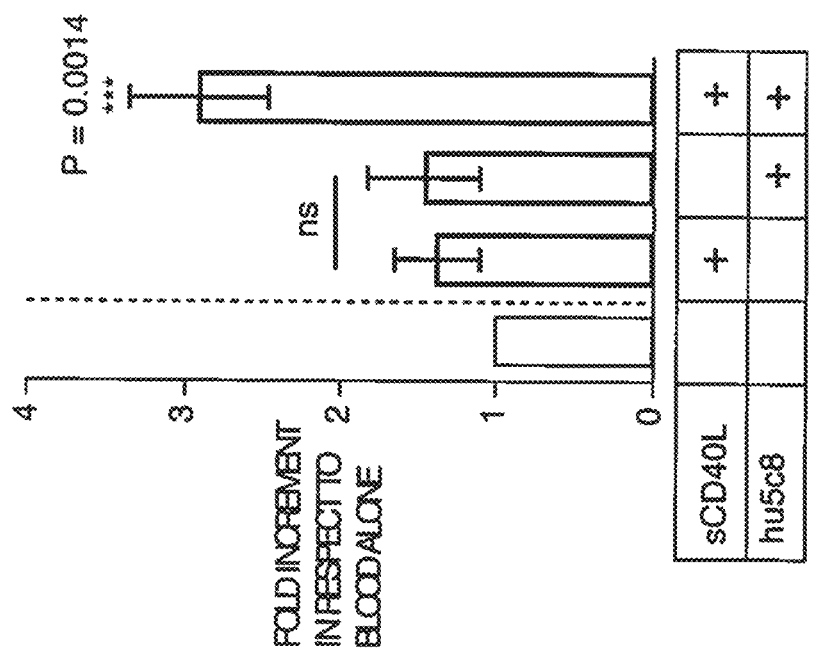
Figure 21E:
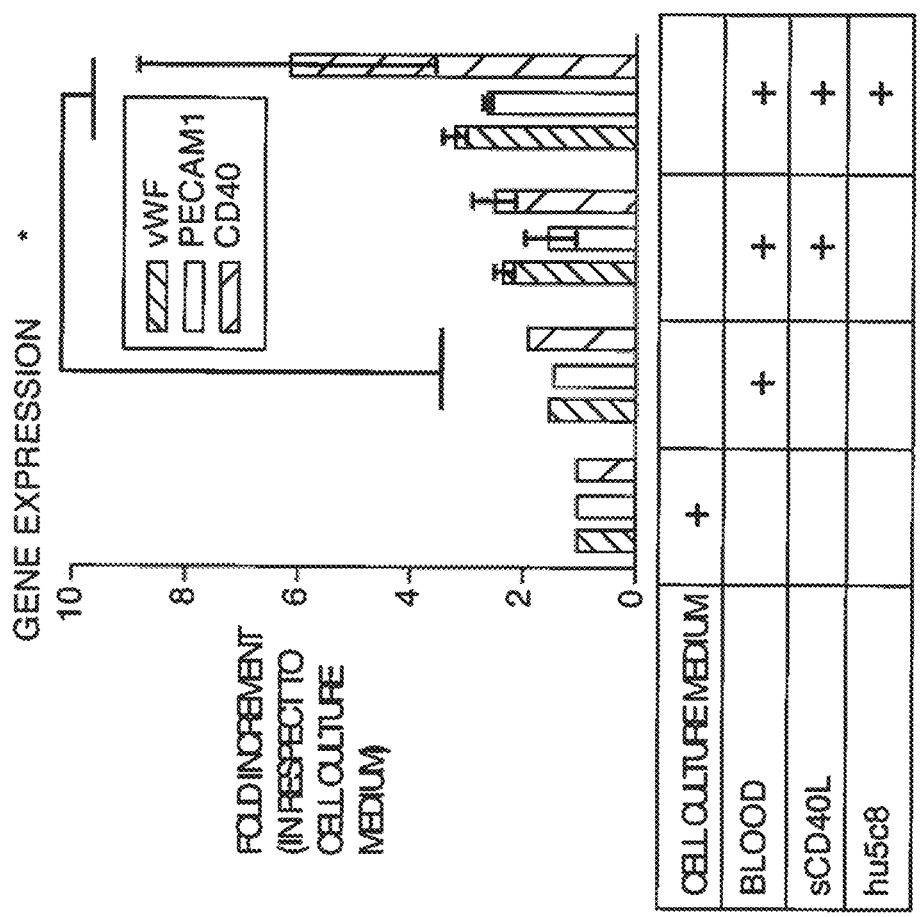
Figure 25B:
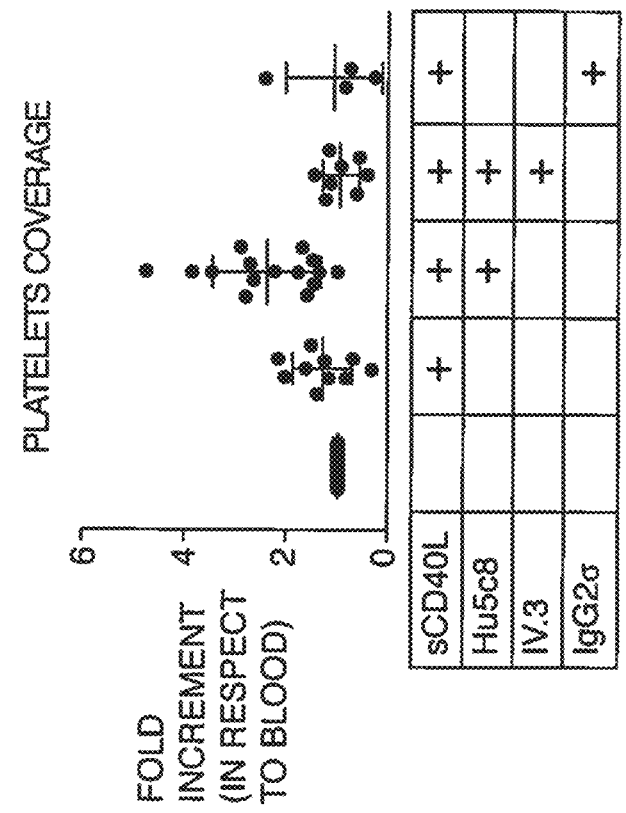
FIGS. 25A-D reveal exemplary mechanistic insights into the thrombosis induced by huSC8/sCD40L-combined on-chip, specifically comparing treatments of sCD40L; $IC_{5C8}$; $IC_{IV.3}$; and $IC_{IgG\sigma}$.
Figure 25A:
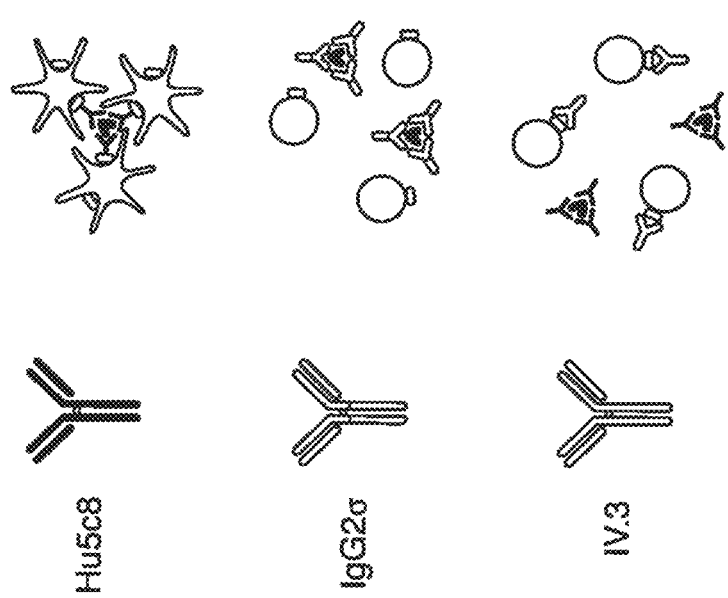
Figure 25D:
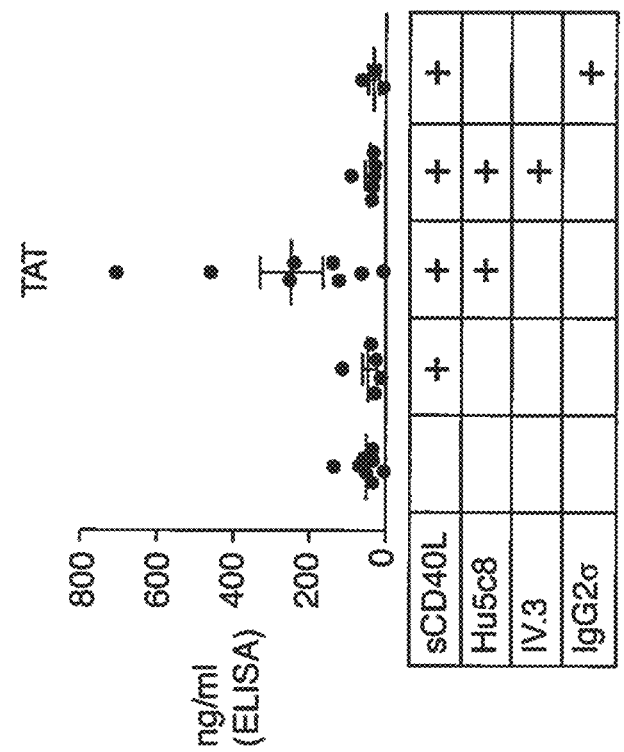
Figure 25C:
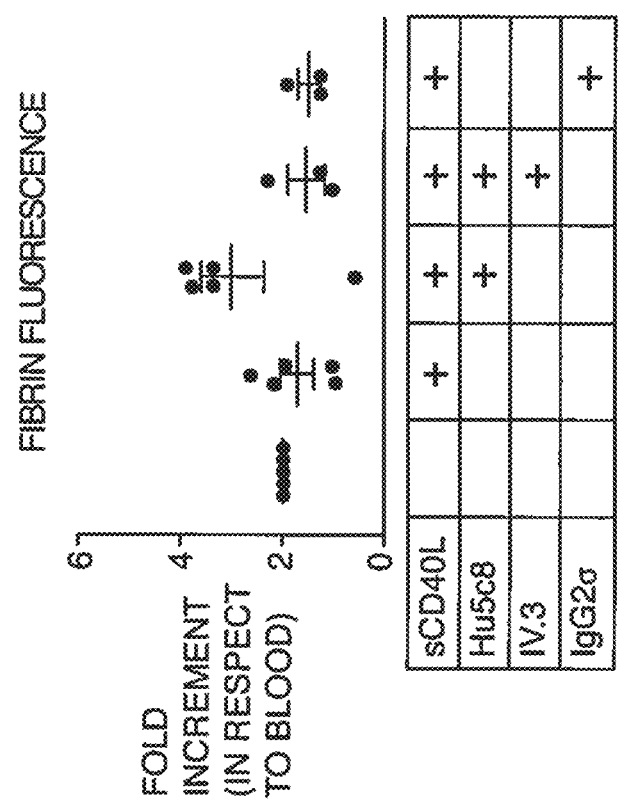
Figure 26B:
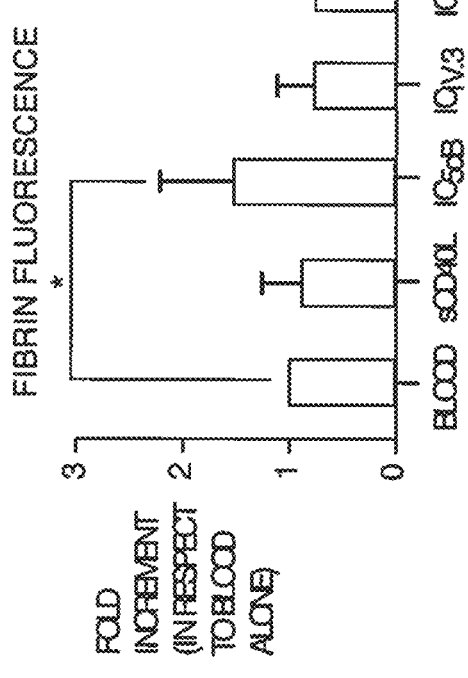
FIGS. 26A-C show exemplary charts comparing untreated blood to treatments of sCD40L; $IC_{5C8}$; $IC_{IV.3}$; and $IC_{IgG\sigma}$ as in the previous figure.
Figure 26A:
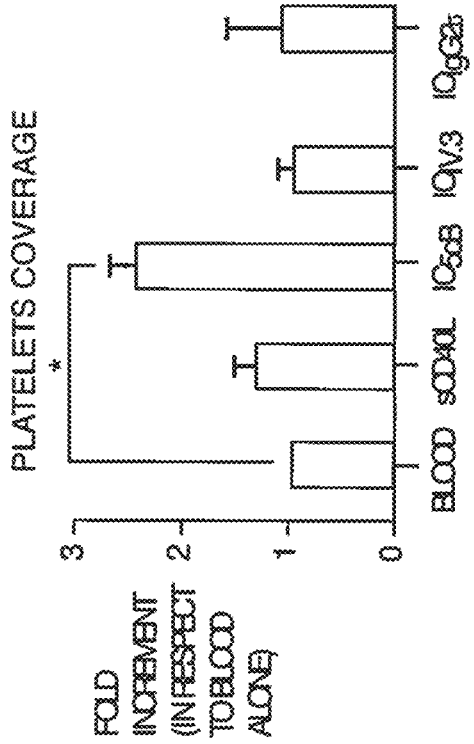
Figure 26C:
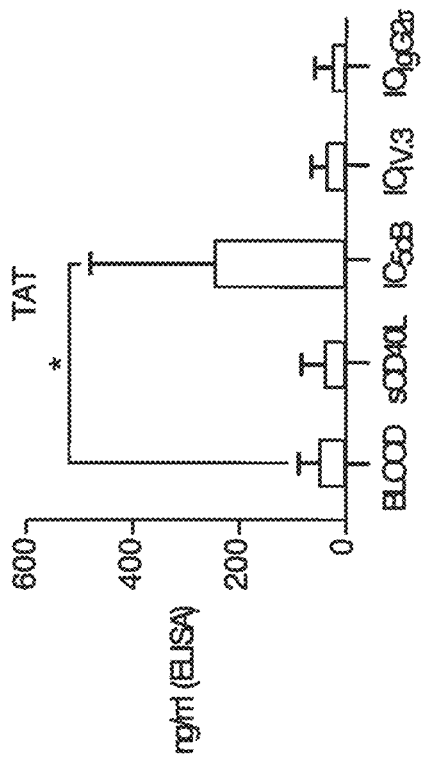
Figures 27A, 27B:
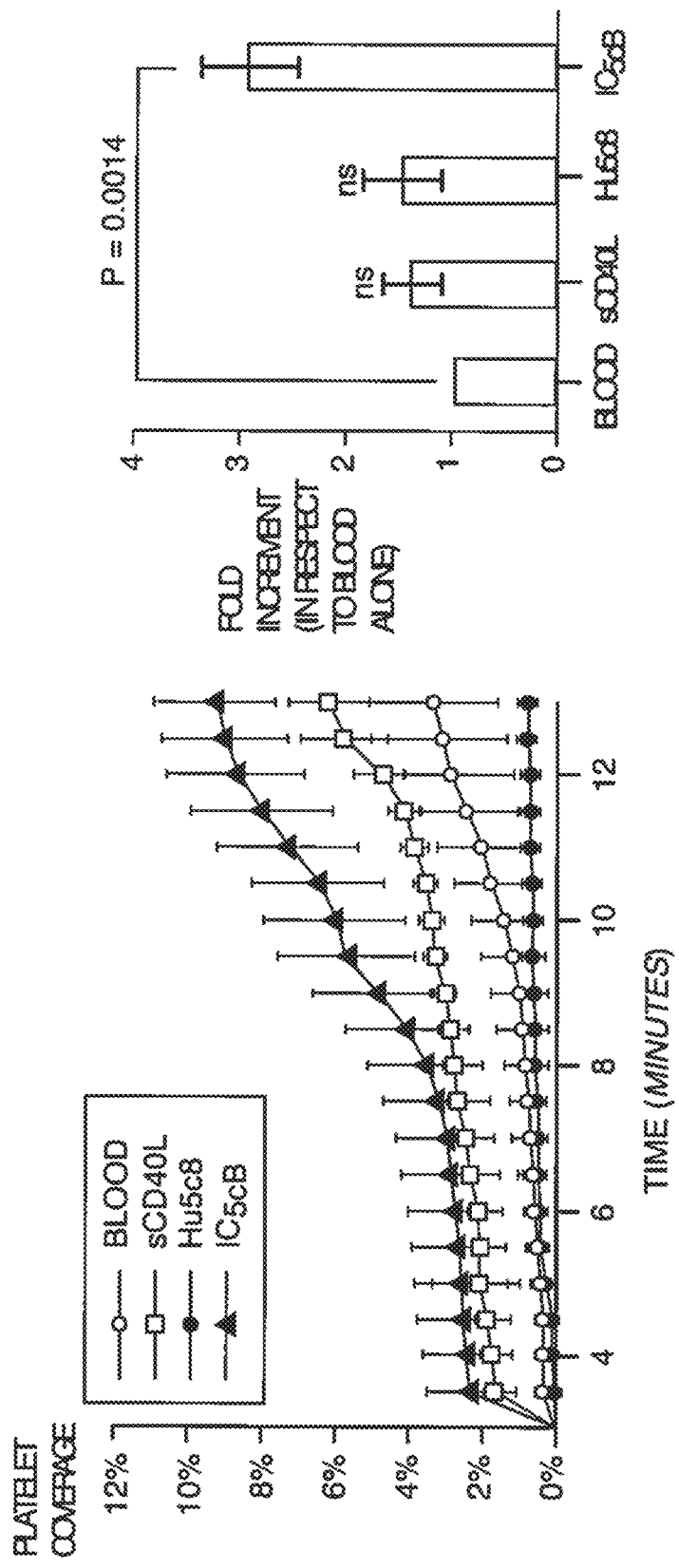
FIGS. 27A-E show exemplary charts, a stained image of blood clots and scanning electron micrographs comparing treatments of blood to untreated blood.
Figure 27C:
Figures 27D, 27E:
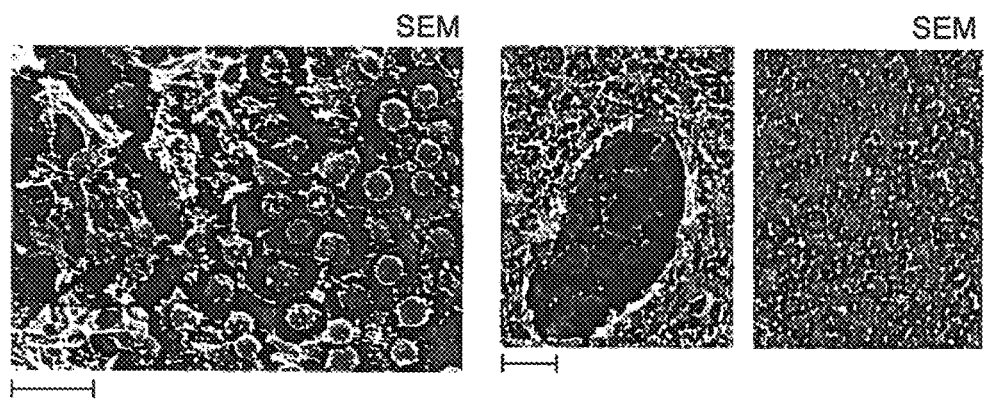

There were no significant treatment-related effects with sCD40L or hu5C8 compared to untreated blood, whereas treatment with hu5C8/sCD40L combined promoted platelet aggregate formation and fibrin deposition on the endothelium (FIG. 25B, FIG. 25C). In line with the hypothesis that binding of hu5C8 to sCD40L promotes platelet activation and aggregation (FIG. 25A), ultimately causing thrombosis in vivo, scanning electron microscopic imaging of the vessel-on-chip perfused with blood containing hu5C8/sCD40L combined revealed the presence of small microthrombi rich in fibrin (FIG. 21B). Additionally, image analysis of platelet coverage conducted on 4 different donors all tested in duplicates, confirmed that the combination of hu5C8 and sCD40L rather than hu5C8 or sCD40L alone, promotes higher clot formation within the biomimetic vessel-on-chip (FIG. 21D). Modest, but significantly increased expression of von Willebrand Factor (vWF), Platelet-Endothelial Adhesion Molecule-1 (PECAM-1, CD31), and CD40 were observed in samples treated with combined hu5C8/sCD40L but not other tested samples, suggesting activation of the endothelium (FIG. 21E).

5. $IC_{5c8}$ Mediated Thrombosis On-Chip Requires FcγRIIa Interaction.

Mechanistic studies[26,50] using platelet assays suggest that a high-ordered ICs of hu5c8 and sCD40L activate platelets via interaction of IgG with FcγRIIa[22,50] receptors expressed on platelets. Recent studies conducted on humanized mice expressing the human Fcγ receptors (FCGR2A) have shown that this receptor plays a role in thrombosis leading to the IC-mediated toxicity[12,16,21]. Notably, the authors of the study reported evidence of platelet aggregation and pulmonary thromboembolism within 10 minutes after injecting the mice with preformed ICs. In order to investigate if the $IC_{5c8}$-induced thrombosis that we observed in our vessel-on-chip system also relies on an Fc-mediated mechanism, we used two different tool molecules: IgG2σ and IV.3 (FIG. 25A). The IgG2σ variant of hu5C8 has an engineered Fc region[48] that eliminates affinity for the FcγRIIa, while the monoclonal antibody IV.3 is a blocking antibody binding to FcγRIIa. Briefly, equimolar concentrations of IgG2σ or hu5c8 were incubated with 10 ng/ml of sCD40L for 20 minutes to form $IC_{IgG2\sigma}$ or $IC_{5c8}$, respectively.

Some of the blood samples were treated with IV.3 (1 µg/ml) for 10 minutes to block the FcγRIIa, and then incubated for 20 more minutes with ICs. Finally, blood alone (control) or blood incubated with $IC_{5c8}$, $IC_{IgG2\sigma}$ or IV.3 was perfused through the biomimetic microfluidic-on-chip for about 10 minutes. We tested 15 donors and all the tested conditions described above were tested in duplicates and analyzed as percentage of platelet coverage based on fluorescence microscopic imaging (FIG. 25B). Five of the donors were also tested for fibrin deposition (FIG. 25C). Finally, effluents plasma obtained from a total of 7 of the donors (including the 5 mentioned before) were used to assess TAT via ELISA (FIG. 25D). Results of platelet coverage and fibrin deposition were normalized with respect to blood alone per each donor tested in order to reduce the sample-to-sample variability naturally occurring in blood samples. Both the use of IgG2σ variants or FcγRIIa blockage via IV.3 suppressed the hu5C8-mediated thrombosis, which is consistent with results that others obtained with 5c8 with mutated low-affinity Fc regions[13]. Notably, there is a large variation in donors, with some responding strongly and others none to the $IC_{5c8}$ at all.

We have observed that some donors have higher sCD40L in the blood and we speculate that this might be one of the factors contributing this donor-to-donor variability (data not shown). The fact that not all blood donors show a pro-thrombotic effect when treated with $IC_{5c8}$ matches the observation that thrombotic and thromboembolic complications of hu5C8 in clinical trials[4] were relatively rare. In addition, RNA from the chip was analyzed for expression of pro-thrombotic markers including vWF, CD40 and PAF-1. We found that IC had increased expression of pro-thrombotic markers (FIG. 24).

As described herein, we have reported and demonstrated a novel biomimetic microfluidic system containing an on-chip blood vessel that can be used to detect early stages in drug-induced thrombosis and thromboembolism. The system includes at least three elements that are necessary for studying blood clotting: a confluent endothelial tissue, human whole blood with an active coagulation cascade and physiologically relevant shear forces. We have demonstrated that the system can be used to analyze multiple aspects of thrombosis, such as platelet adhesion, aggregation, fibrin formation and TAT release, all in a single assay and some of which in real-time.

Moreover, we have shown that the system mimics pro-thrombotic responses due to vascular endothelial activation and sCollagen-mediated coagulation and platelet activation. Notably, thrombotic events recapitulated in the system can be inhibited by clinically relevant dosages of the anti-platelet medical drug Eptifibatide.

Additionally, we have shown that the relatively rare and mechanistically complex pro-thrombotic effect of the anti-CD154 mAb hu5C8 can be recapitulated in our system at clinically relevant dosages. Hu5C8 mediated increases in platelet adhesion, fibrin clot formation, and increases in TAT release in the presence of pathophysiological concentrations of sCD40L were all attenuated by blocking interactions with FcγRIIa or by use of a hu5C8 variant with a low binding affinity to FcγRIIa. These findings provide confidence that there is a low risk for thrombosis in the clinic for a new generation anti-CD154 mAbs that have been modified not to interact with FcγRIIa receptors[23]. Taken together, our results clearly demonstrate that the microfluidic-on-chip blood could be used as a safety model to de-risk issues related to thrombosis in the drug development process, and potentially as an efficacy model for discovery of anti-thrombotic compounds and dissection of complex molecular mechanisms. The studies described herein, reinforces the conclusions from other studies on hu5C8-mediated thromboembolism. The results of our study unequivocally demonstrate the potential added value of microfluidic-on-chip technology in the preclinical testing of medical drugs.

Additional references herein incorporated by reference:
1. Daoussis, D., Andonopoulos, A. P. & Liossis, S.-N. C. Targeting CD40L: a Promising Therapeutic Approach. Clin. Vaccine Immunol. 11, 635-641 (2004).
2. Peters, A. L., Stunz, L. L. & Bishop, G. A. CD40 and autoimmunity: The dark side of a great activator. Semin. Immunol. 21, 293-300 (2009).

3. Kirk, A. D. et al. Treatment with humanized monoclonal antibody against CD 154 prevents acute renal allograft rejection in nonhuman primates. Nat. Med. 5, 686-693 (1999).
4. Kirk, A. D. et al. CTLA4-Ig and anti-CD40 ligand prevent renal allograft rejection in primates. Proc. Natl. Acad. Sci. U.S.A 94, 8789-8794 (1997).
5. Kenyon, N. S. et al. Long-term survival and function of intrahepatic islet allografts in rhesus monkeys treated with humanized anti-CD154. Proc. Natl. Acad. Sci. 96, 8132-8137(1999).
6. Elster, E. A. et al. Treatment with the humanized CD154-specific monoclonal antibody, hu5CS, prevents acute rejection of primary skin allografts in nonhuman primates. Transplantation 72, 1473-1478 (2001).
7. Pierson, R. N. et al. Prolongation of primate cardiac allograft survival by treatment with ANTI-CD40 ligand (CD154) antibody. Transplantation 68, 1800-1805 (1999).
8. Zhang, T., Pierson, R. N. & Azimzadeh, A. M. Update on CD40 and CD154 blockade in transplant models. Immunotherapy 7, 899-911 (2015).
9. Huang, W. et al. The effect of anti-CD40 ligand antibody on B cells in human systemic lupus erythematosus. Arthritis Rheum. 46, 1554-1562 (2002).
10. Boumpas, D. T. et al. A short course of BG9588 (anti-CD40 ligand antibody) improves serologic activity and decreases hematuria in patients with proliferative lupus glomerulonephritis. Arthritis Rheum. 48, 719-727 (2003).
11. Liossis, S.-N. C. & Sfikakis, P. P. Costimulation Blockade in the Treatment of Rheumatic Diseases: BioDrugs 18, 95-102 (2004).
12. Chan, A. C. & Carter, P. J. Therapeutic antibodies for autoimmunity and inflammation. Nat. Rev. Immunol. 10, 301-316 (2010).
13. Kuwana, M. Effect of a single injection of humanized anti-CD154 monoclonal antibody on the platelet-specific autoimmune response in patients with immune thrombocytopenic purpura. Blood 103, 1229-1236 (2003).
14. Kimura, K. et al. Study of Plasma Levels of Soluble CD40 Ligand in Systemic Lupus Erythematosus Patients Who Have Undergone Plasmapheresis. Ther. Apher. Dial. 9, 64-68 (2005).
15. Danese, S. Activated platelets are the source of elevated levels of soluble CD40 ligand in the circulation of inflammatory bowel disease patients. Gut 52, 1435-1441 (2003).
16. Freedman, J. E. CD40-CD40L and Platelet Function: Beyond Hemostasis. Circ. Res. 92, 944-946 (2003).
17. Henn, V. et al. CD40 ligand on activated platelets triggers an inflammatory reaction of endothelial cells. Nature 391, 591-594 (1998).
18. Prasad, K. S. S., Andre, P., Yan, Y. & Phillips, D. R. The platelet CD40L/GP IIb-IIIa axis in atherothrombotic disease. Curr. Opin. Hematol. 10, 356-361 (2003).
19. P. Ferroni, B. S. P., F. Santilli, B. S. P., F. Guadagni, B. S. P., S. Basili, B. S. P. & G. Davi, B. S. P. Contribution of Platelet-Derived CD40 Ligand to Inflammation, Thrombosis and Neoangiogenesis. Curr. Med. Chem. 14, 2170-2180 (2007).
20. Andre, P., Nannizzi-Alaimo, L., Prasad, S. K. & Phillips, D. R. Platelet-Derived CD40L: The Switch-Hitting Player of Cardiovascular Disease. Circulation 106, 896-899 (2002).
21. Duffau, P. et al. Platelet CD154 Potentiates Interferon-Secretion by Plasmacytoid Dendritic Cells in Systemic Lupus Erythematosus. Sci. Transl. Med. 2, 47ra63-47ra63 (2010).
22. Langer, F. et al. The role of CD40 in CD40L- and antibody-mediated platelet activation. Thromb. Haemost. 93, 1137-1146 (2005).
23. Xie, J. H. et al. Engineering of a Novel Anti-CD40L Domain Antibody for Treatment of Autoimmune Diseases. J. Immunol. 192, 4083-4092 (2014).
24. Koyama, I. et al. Thrombophilia associated with anti-CD154 monoclonal antibody treatment and its prophylaxis in nonhuman primates. Transplantation 77, 460-462 (2004).
25. Roth, G. A. et al. Thrombophilia associated with anti-CD154 monoclonal antibody treatment and its prophylaxis in nonhuman primates. Transplantation 78, 1238-1239; author reply 1239 (2004).
26. Wakefield, Ian, Harari, Olivier, Hutto, David, Burkly, Linda, Ferrant, Janine, Taylor, Fred, et al; An Assessment of theThromboembolic Potential of CDP7657, a Monovalent Fab' PEG Anti-CD40L Antibody, in Rhesus Macaques. Arthritis Rheum Abstr. 62, Suppl 10:1243 (2010).
27. Shock, A. et al. CDP7657, an anti-CD40L antibody lacking an Fcc domain, inhibits CD40L-dependent immune responses without thrombotic complications: an in vivo study. Arthritis Res. Ther. 17, (2015).
28. Sidiropoulos, P. I. & Boumpas, D. T. Lessons learned from anti-CD40L treatment in systemic lupus erythematosus patients. Lupus 13, 391-397 (2004).
29. van der Meer, A. D. & van den Berg, A. Organs-on-chips: breaking the in vitro impasse. Integr. Biol. Quant. Biosci. Nano Macro 4, 461-470 (2012).
30. Bhatia, S. N. & Ingber, D. E. Microfluidic organs-on-chips. Nat. Biotechnol. 32, 760-772 (2014).
31. Ingber, D. E. Reverse Engineering Human Pathophysiology with Organs-on-Chips. Cell 164, 1105-1109 (2016).
32. Westein, E. et al. Atherosclerotic geometries exacerbate pathological thrombus formation poststenosis in a von Willebrand factor-dependent manner. Proc. Natl. Acad. Sci. U.S.A. 110, 1357-1362 (2013).
33. Tsai, M. et al. In vitro modeling of the microvascular occlusion and thrombosis that occur in hematologic diseases using microfluidic technology. J. Clin. Invest. 122, 408-418 (2012).
34. Westein, E., de Witt, S., Lamers, M., Cosemans, J. M. E. M. & Heemskerk, J. W.
   M. Monitoring in vitro thrombus formation with novel microfluidic devices. Platelets 23, 501-509 (2012).
35. Jain, A. et al. Assessment of whole blood thrombosis in a microfluidic device lined by fixed human endothelium. Biomed. Microdevices 18, (2016).
36. Huh, D. et al. Reconstituting organ-level lung functions on a chip. Science 328, 1662-1668 (2010).
37. Huh, D. et al. A Human Disease Model of Drug Toxicity-Induced Pulmonary Edema in a Lung-on-a-Chip Microdevice. Sci. Transl. Med. 4, 159ra147-159ra147 (2012).
38. Yau, J. W., Teoh, H. & Verma, S. Endothelial cell control of thrombosis. BMC Cardiovasc. Disord. 15, (2015).
39. Nishizawa, E., Wynalda, D., Suydam, D., Sawa, T. & Schultz, J. Collagen-induced pulmonary thromboembolism in mice. Thromb. Res. 1, 233-241 (1972).
40. Monroe, D. M. Platelets and Thrombin Generation. Arterioscler. Thromb. Vasc. Biol. 22, 1381-1389 (2002).
41. Jung, S. M. & Moroi, M. Platelets Interact with Soluble and Insoluble Collagens through Characteristically Different Reactions. J. Biol. Chem. 273, 14827-14837 (1998).

42. Cines, D. B. et al. Clot contraction: compression of erythrocytes into tightly packed polyhedra and redistribution of platelets and fibrin. Blood 123, 1596-1603 (2014).
43. Tutwiler, V., Wang, H., Litvinov, R. I., Weisel, J. W. & Shenoy, V. B. Interplay of Platelet Contractility and Elasticity of Fibrin/Erythrocytes in Blood Clot Retraction. Biophys. J. 112, 714-723 (2017).
44. Phillips, D. R. & Scarborough, R. M. Clinical pharmacology of eptifibatide. Am. J. Cardiol. 80, 11B-20B (1997).
45. Hagemeyer, C. E. & Peter, K. Targeting the platelet integrin GPIIb/IIIa. Curr. Pharm. Des. 16, 4119-4133 (2010).
46. Kato, K. et al. The soluble CD40 ligand sCD154 in systemic lupus erythematosus. J. Clin. Invest. 104, 947-955 (1999).
47. dela Paz, N. G. & D'Amore, P. A. Arterial versus venous endothelial cells. Cell Tissue Res. 335, 5-16 (2009).
48. Speiser, W. et al. D-dimer and TAT measurement in patients with deep venous thrombosis: utility in diagnosis and judgement of anticoagulant treatment effectiveness. Thromb. Haemost. 64, 196-201 (1990).
49. Inoh, M., Tokuda, M., Kiuchi, H., Kurata, N. & Takahara, J. Evaluating systemic lupus erythematosus disease activity using molecular markers of hemostasis. Arthritis Rheum. 39, 287-291 (1996).
50. Robles-Carrillo, L. et al. Anti-CD40L Immune Complexes Potently Activate Platelets In Vitro and Cause Thrombosis in FCGR2A Transgenic Mice. J. Immunol. 185, 1577-1583 (2010).
51. Prasad, K. S. S. et al. Soluble CD40 ligand induces 3 integrin tyrosine phosphorylation and triggers platelet activation by outside-in signaling. Proc. Natl. Acad. Sci. 100, 12367-12371 (2003).
52. Huh, D. et al. Microfabrication of human organs-on-chips. Nat. Protoc. 8, 2135-2157 (2013).
53. Csomor, K. & KdrpAti, E. Effect of vintoperol on platelet aggregation and experimental thrombosis. Arzneimittelforschung. 44, 36-40 (1994).
54. Eptifibatide for Intravenous Administration—FDA.

VI. Collagen Coating of Multichannel Microfluidic Chips.

In some embodiments, the collagen solution for coating of the microchannels is prevented from entering an "on-chip" reservoir. Prevention includes, but is not limited to, using an amount of coating solution that is less than the channel volume. For example, when a channel volume is 4 ul, 3.5 ul of collagen solution is added, in part because the entire channel is not coated. In some embodiments, a collagen solution is used for coating 4 and 8 microchannel chips. In one embodiment, the entire chamber was coated, prior to the addition of cells, with extracellular matrix (ECM), e.g. fibronectin, various collagen types or combinations thereof, including but not limited to an exemplary ECM consisting of a mixture of rat tail collagen I and fibronectin.

V. Exemplary Methods of Using Embodiments of a Microfluidic-Chip Device.

In one embodiment, a blood sample is drawn into a tube containing anticoagulant to inactivate the coagulation cascade at collection. The sample can be tested or evaluated in a microfluidic device or chip. As a portion of the sample enters the chip (e.g. via an input port), a solution of calcium and magnesium (present in one or more additive channels positioned at or near the input port in fluidic communication therewith) is introduced into that fraction of the sample making contact with the solution. The reagents in the solution re-activate the native coagulation cascade, but only for that portion of the blood sample making contact with it. The active blood (e.g. blood capable of clotting) flows through the chip, e.g. through the microchannel. Where the microchannel contains cells, the active blood can interact with these cells within the "active" region of the microchannel.

In a preferred embodiment, the blood exiting the "active" region makes contact (and is even mixed) with additional anticoagulant (present in one or more additive channels in fluidic communication with the microchannel and/or output port), so that that portion of the sample exiting the microfluidic channel (and leaving the chip through an output port) remains substantially clot-free or unclotted. In this manner, the blood remains in a liquid state after testing (i.e. downstream of the "active" region).

In some embodiment, the additive channel at the outlet can be used to add other reagents (e.g. for staining), fixatives (e.g. for capturing the cells and platelets in their state immediately after contact with the cells in the chip), oil to form blood-containing droplets (e.g. for sequestering blood samples from different time-points in the run, and analyzing them separately afterwards), etc. The addition of an additive channel near the outlet allows (is a versatile way) quick treatment of blood samples as they leave the chip. Such treated blood samples are contemplated to enable downstream analysis including but not limited to new types of analysis from the use of the additive channel for treating blood components as it leaves the chip.

Replicates of the microfluidic-chip device may be made and run in parallel or at different times in order to show consistency in the results, i.e. the data is good.

It is not intended that the present invention be limited by the type of testing done on the blood (or other fluid) introduced into the microfluidic device. One aspect described herein relates to a method of determining cell function. In one embodiment, the method comprises (a) flowing a fluid sample over a surface comprising a monolayer of cells of a first type thereon; and (b) detecting interaction between cells of a second type in the fluid sample and the monolayer of cells of the first type. The function of the cells of the second type in the fluid sample can then be determined based on the detected cell interaction. In some embodiments, the monolayer of cells of the first type can comprise endothelial cells, and the cells of the second type in the fluid sample can comprise blood cells, e.g., platelets (see FIG. 10). In one embodiment, the endothelial cells are living cells. In another embodiment, they are fixed cells (i.e. cells treated with a fixative). Accordingly, another aspect provided herein relates to a method of determining platelet function, which comprises (a) flowing a fluid sample over a surface comprising an endothelial cell monolayer thereon; and (b) detecting interaction between blood cells (e.g., platelets) in the fluid sample and the fixed endothelial cell monolayer.

VI. "Active" Region of the Microchannel.

In some embodiments, a microfluidic chip unit presents an "active volume," "active region" or "active area" in which the desired conditions and fluid-dynamic regimes for flowing blood are re-created, such that a microchannel contains endothelial cells lining the channel surface enclosing the "active volume." Designating an active volume area for observations and measurements is to avoid measuring background activation of blood, e.g. when it merely touches the micro-device surfaces. Designating an active volume area also allows direct investigation of the interaction of the blood with an endothelial cell layer, thus eliminating edge effects of the cell layer or the microfluidic channel. Further, an active volume area identifies the same locations in parallel for different microchannels.

VII. "On-Chip" and "Off-Chip" Fluid Reservoirs.

In some embodiments, reservoirs containing blood samples are used with tubing for use in fluidic loading of blood samples onto the chip. In some embodiments, such tubing is flexible. In some embodiments, reservoirs containing blood samples are loaded using materials and methods that do not use flexible tubing. Instead blood samples may be loaded into on-chip reservoirs using short rigid connectors, such as leurs, for one example, which are attached to syringes. In some examples, an off-chip reservoir may be loaded with a blood sample then inserted into a modified on-chip reservoir, wherein such modification allows for receiving the preloaded off-chip reservoir. Thus, in preferred embodiments, blood samples are loaded into microfluidic chip reservoirs allowing blood samples to flow into microchannels of microfluidic devices without using tubing attached to inlet ports. In fact, in some embodiments, inlet ports are replaced with fluid reservoirs. Thus, in some embodiments, fluid reservoirs are "on-chip", wherein in one nonlimiting example, said reservoirs are molded into the microfluidic device. In some embodiments, fluid reservoirs are "off-chip" reservoirs, wherein in one nonlimiting example, a syringe may be considered an "off-chip" reservoir. In some embodiments, an "off-chip" reservoir may be inserted into the space created "on-chip" during fabrication of the microfluidic device.

In one embodiment, a microfluidic device has "on-Chip" molded fluid reservoirs for receiving blood samples in amounts larger than able to flow into the microfluidic channels at one time. In one embodiment, an "on-Chip" reservoir refers to an opening that is designed to be molded directly into the chip during chip fabrication for providing a microfluidic device without the use of tubing for inflowing blood samples onto a chip. The use of an "on-chip" reservoir, in part, eliminates material concerns from the tubing (one less material to worry about), and simply leads to fewer parts to "plumb up" i.e. fluidically connect together. Thus, a blood sample is added to a large reservoir opening within the chip then pushed or pumped through the small opening into the microfluidic channel.

The design of the on-chip reservoir is contemplated to reduce shear forces on blood components, including but not limited to proteins and cells, flowing into and out of circular tubes/channels fluidically connected to reservoirs. Physics principles, in part relating to Hagen-Poiseuille's Law, which basically states that shear stress decreases to the 4th power with increasing radius. Thus when applied to tube diameter and shear stress indicates that a small increase in tubing radius has a significant effect on decreasing shear stress. Thus, shear stress in the reservoir and inlet channel is contemplated as low, i.e. little or no effect on sample components, in part because the dimensions are large compared to the part of the channel where measurements/ analysis is made. In another embodiment, a microfluidic device has an "on-Chip" reservoir that is not molded into the chip, referring to a reservoir that is filled with a blood sample prior to insertion into the large opening molded into the chip. In this embodiment, a blood sample is loaded into a disc shaped reservoir then inserted into the large opening in the chip. In one embodiment, as the disc reservoir moves, e.g. pushed, into the large opening in the chip, a smaller covered opening in the disc reservoir aligns with the end of the microchannel which snaps open the disc opening for allowing the blood sample to flow from the disc into the microchannel. Thus in one embodiment, after alignment of the openings allows fluidic communication between the blood sample in the disc reservoir, gravity pulls the blood sample through the microchannel. In one embodiment, after alignment of the openings allows fluidic communication between the blood sample in the disc reservoir and the microchannel, a micropump pushes the blood sample through the microchannel. In one embodiment, after alignment of the openings allows fluidic communication between the blood sample in the disc reservoir and the microchannel, a vacuum or pump attached to the outflow port pulls the blood sample from the reservoir through the microchannel and out the outflow port.

In yet another embodiment, a microfluidic device has an "off-Chip" fluid reservoir referring to a fluid reservoir that is not fabricated as part of the chip. Thus an "off-chip" reservoir contains a blood sample that has a part, or is capable of connection to a part, that in turn is capable of insertion into at least a portion of the large opening molded into the chip for dispensing a blood sample into the chip. including, but not limited to a syringe as one example of a reservoir. As one example of a reservoir, a plastic luer connector attaches a syringe reservoir to a chip device, such that at least in part, the large opening in the device reduces shear on blood flowing in from the reservoir. In some embodiments, each channel is prepped and imaged at once.

In some embodiments, a large "on-chip" reservoir is designed to be large enough to reduce the shear on the blood introduced into the microfluidic channels from the reservoir, in part because excessive shear is known to induce coagulation.

In some embodiments, the opening between the reservoir and microchannel is designed to be large enough to reduce the shear on the blood introduced into the microfluidic channels from the reservoir, in part because excessive shear is known to induce coagulation.

Figure 29:
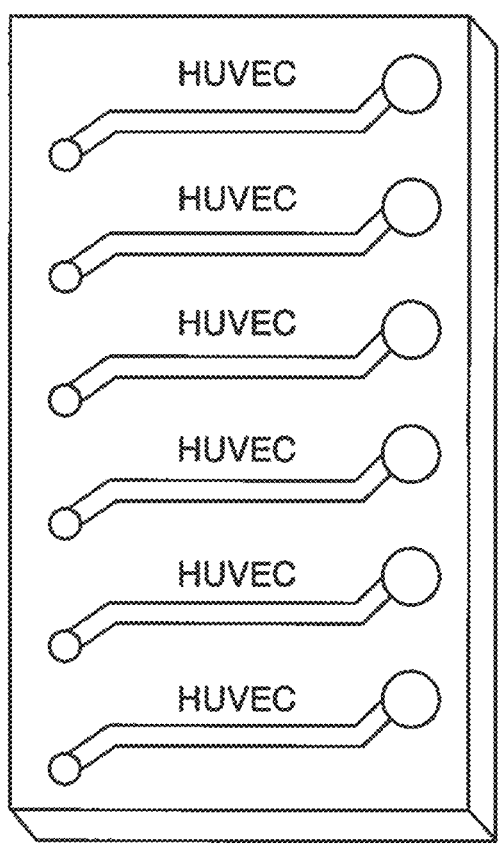
FIG. 29 shows a schematic drawing of one embodiment of an exemplary six-channel microfluidic device where each end of a microchannel terminates at a port. In some embodiments, the inlet port is a large opening, such as shown on the right. In some embodiments, the large opening serves as an "on-chip" fluid reservoir (or connects to a reservoir). In some embodiments, HUVEC cells coat at least a portion of the inside of a microchannel. In some embodiments, HUVEC cells coat the entire microchannel. In some preferred embodiments, the outlet port is located at the opposite end from the inlet port.

One embodiment is shown in a schematic drawing as an exemplary six-channel chip is shown in FIG. 29. FIG. 29 shows a schematic drawing of an exemplary six-channel device, where, in some embodiments, a large opening as an "on-chip" fluid reservoir is provided at the end of a microchannel.

VIII. Geometries of Fluid Channels.

Figure 30A:
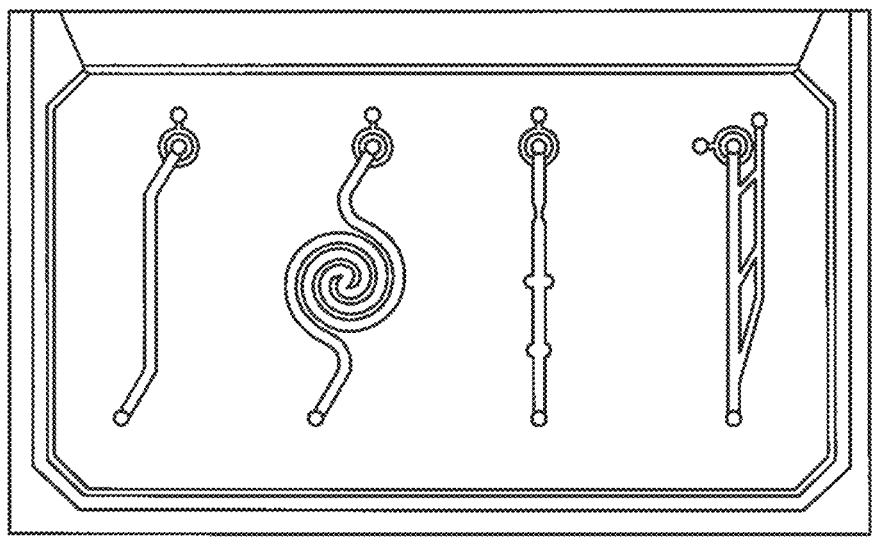
FIG. 30A-C shows schematic drawings of an exemplary four channel microfluidic device illustrating four exemplary embodiments of pre-set microchannel geometries contemplated for use in recreating specific fluidic dynamics of the blood flow.
Figure 30B:
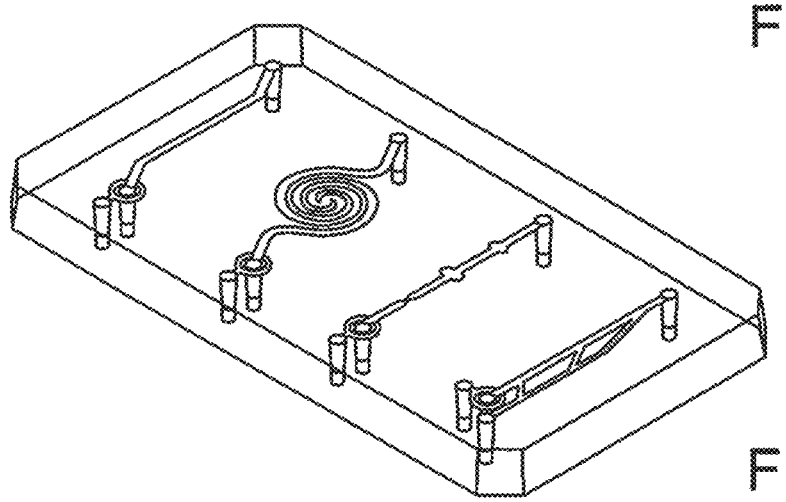
Figure 30C:
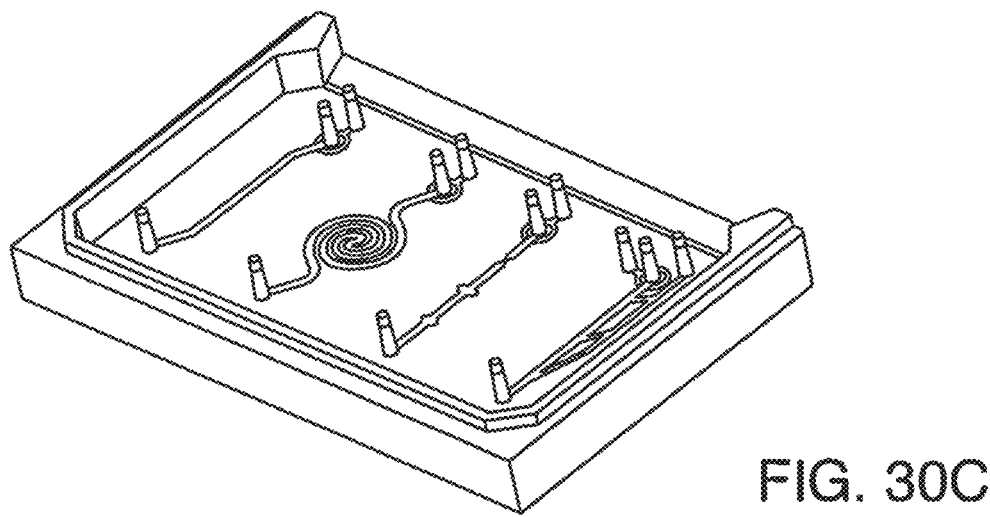

The microfluidic channel can be designed in different geometries, for example, as shown in illustrations in FIGS. 30A-C. In some embodiments, different microchannel geometries can be grouped together, see FIG. 30A. In yet further embodiments, different geometries are grouped together for viewing in one or more microscope or video camera fields of vision.

In some embodiments, different microchannel geometries are individually isolated and connected in various way through their inlet and outlet. For instance, FIG. 29 shows a chip where microchannels are arranged in parallel, but they can also be arrange in series. For instance, for testing different lengths of microchannels, connecting multiple channel units of the same type or connecting different types in series is contemplated for testing coagulation effects of different distances of fluid flow on blood-cells flowing in single or multiple geometries.

Many variations of geometries are contemplated for use in channel design, construction and use. In fact, nonlimiting examples of a specific geometry of a microfluidic channel, includes but is not limited to linear, linear with curves, spiral, discontinuous widths, bifurcating channels, etc., to individually test the effect of specific geometry on blood flow through the microfluidic device.

Fluids flowing through these devices are not limited to blood. Indeed, microfluidic systems are designed to perfuse different fluid such as blood, plasma, culture medium, etc. Such that, analysis of events within these devices are not limited to fluids. Indeed, interactions are contemplated for analysis of any particle or groups of particles flowing through different types of geometric shapes of channels of the microfluidic devices, including but not limited to particles found in blood, e.g. blood clotting components, red blood cells, white blood cells, etc.

Biophysical blood cell-endothelial interactions in regions where abrupt changes in the vascular geometry induce complex local hemodynamic conditions that are relevant to disease pathophysiology.

Further, it is not meant to limit the types of geometries or types of fluid dynamics, such that other types of geometry for providing custom fluidic dynamics of blood flow are contemplated. In fact, although three of the four geometries shown each have two additive channels fluidically attached to one input port, one of the embodiments shown in FIG. 30A, far right has a bifurcating-channel, thus, the microfluidic channel has three ports, two, one on each side of the chip without additive channels, while the third port has additive channels fluidically attached to one input port. In one embodiment, one outlet has two additive channels, fludically connected to one input port which is used for analysis of the outflow thus coagulation downstream of the second channel, without additive channels, is immaterial. Further, because each additive channel input is contemplated to have its own pump, the second outlet port would not require a second additive channel pump. However, in some embodiments both outlet ports have additive channels. In this embodiment, each additive channel input port is contemplated to be attached to a separate pump. In other embodiments, one pump may be used for multiple additive channel input ports. In yet another embodiment, a microfluidic device contemplated for use has a bifurcating-channel geometry without additive channels at the inlet or outlet ports. In one embodiment shown, the three geometries on the left have one port without additive channels with the port on the other end having additive channels and one input for two channels.

FIG. 30A-C shows schematic drawings of an exemplary 4 channel microfluidic device illustrating four exemplary embodiments of pre-set microchannel geometries contemplated for use in recreating specific fluidic dynamics of the blood flow. FIG. 30A shows one embodiment of a schematic top view of a 4 channel chip having four exemplary pre-set microchannel geometries with the same Outflow rate, e.g. having a 100 um Outflow, also shown in FIG. 30B and FIG. 30C (bottom view), FIG. 30B shows a schematic bottom view diagram of an exemplary 4 channel microfluidic device. FIG. 30C shows one embodiment of a schematic 3-D angular view of a 4 channel microfluidic device contemplated for use as a mold for fabricating chips shown in FIG. 30A and FIG. 30B.

IX. EDTA Outflow

In some embodiments, a fluidically interconnected double port is located in the outflow part of the device. This technical feature, called "EDTA outflow" refers to a round channel that intersect the main channel to provide a continuous mixing of two different fluids and/or solutions. An EDTA outflow is contemplated for use in at least two different types of applications. In the first type of application, an EDTA outflow is used for adding compounds in solution, such as drugs, anti-coagulants, etc., into the incoming fluid (blood, serum, medium) in a continuously manner. In one embodiment of this application the concentration of the incoming solution will be established according to the specific use or to the specific final concentration one desires to achieve. Such that, the concentrations of compounds in the incoming solutions may be chosen from a range of concentrations. In one embodiment the type of solute will be varied depending upon the effect under experimentation. In one embodiment the geometry and the dimensions of the "EDTA outflow" channel will be varied according to the specific use. In one embodiment specific final concentration one desires to achieve). In a second type of application the "EDTA outflow" channel is mainly used to add EDTA (or similar chelators) to the blood flowing out of the chip with the ultimate goal to avoid coagulation of the blood in the outlet port and allow the collection of blood for analysis. In this second type of application is also contemplated the use of the port to directly add fluorescent dies, antibody or other detection solution to screen the blood. This last application is particularly interesting when the aim is that to detect molecule with short or very short half-life.

Other blood chelators are contemplated including but not limited to: EDTA, Heparin, Citrate, Dimercaprol (2,3-dimercapto-1-propanol), Ethylenediamine, Phorphine and Heme group. "EDTA outflow" channel dimensions might need to be adjusted according to the specific chelator or solution added. Note: the "EDTA outflow" channel can be used to prevent blood from coagulate inside the channel during experiments that require direct injection of blood from freshly isolated patient (we contemplate this application for use in personalized medicine screening and/or testing). "EDTA outflow" channel is a critical feature of the devise to take in consideration.

X. Viewing/Imaging Microchannels Using Side-by-Side Imaging Fields.

In some embodiments, the active region of a microfluidic channel may have optically transparent viewing areas such that observations of components inside of the microchannel are visible to an observer viewing the microfluidic device. Thus, at least half of the upper area of the active area of the microchannel and the chip material in between the active area and the observer are constructed of optically clear material. In some embodiments, the entire active area of the microchannel is made of optically clear material. In some embodiments, the entire microchannel is made of optically clear material. In some embodiments, the entire microfluidic chip device is made of optically clear material.

A. Viewing/Imaging Microchannels

In some embodiments, a viewer, or any means of enhanced viewing such as when using a microscope, e.g. still microscopy imaging during or at the end of the experiment; images (including but not limited to photographs) and videos of fluidic events imaged by video camera; video microscopy; optofluidic microscopy (OFM) (referring to the use of light-sources to record projection images of objects flowing above a sensor-array, and utilizing this flow to digitally achieve a spatial resolution beyond the pixel size of the sensors, lens-free optical tomographic microscope, lensfree optical on-chip microscopy, in one embodiment based on partially coherent on-chip holography, including but not limited to portable telemedicine microscopy, cellphone based microscopy and field-portable optical tomographic microscopy, etc., can access (view, observe, or see) are contemplated for use with microfluidic chip devices described herein. In one embodiment, multiple channels are within the range of motion of the microscope stage. In a preferred embodiment, sizes of active areas of channels match the viewing area of the imaging means such that the active areas are capable of being viewed within a single field-of-view of the viewing/imagining means. In other words, all of the microfluidic channels during a single experiment may be viewed. As one example, events in four channels used simultaneously during an experiment are capable of being imaged within one field of view. In a preferred embodiment, a single image captures multiple experimental conditions or replicates.

In some embodiments, combinations of systems are contemplated. As one nonlimiting example, coupling automated imaging and segmentation systems with microfluidic devices is contemplated to increase through put of samples.

B. Side-By-Side Imaging Fields

In some embodiments, side-by side imaging fields are located at or beneath the active area of the microchannel. It is not meant to limit the outside dimensions of these imaging fields. Thus, in one non-limiting example, the outside dimensions is defined as that area that may be observed by a light microscope within a single field-of-view of the microscope. In some embodiments, there are subdivisions creating smaller areas within the outside dimensions of the imaging field. In some exemplary embodiments, an imaging field may be referred to as a Tile. One exemplary Tile Area is 1350 um by 1350 um which is entirely visible viewed with an Olympus Light Microscope, see FIG. 31A. In one embodiment, a 12 Tile is provided, wherein each Tile Area, or quadrant, is 1350 um by 1350 um, forming a 12 quadrant having 4 tiles across and 3 tiles length (down), i.e. a total of 5.4 mm across (4 quadrants) and 4.05 mm in length (3 quadrants), see FIG. 31B. However, it is not meant to limit either the size of the Tile or the number of Tiles (quadrants). In some embodiments, each of the Tiles (quadrants) is subdivided into smaller quadrants. In further embodiments, each of the subdivided quadrants is subdivided into smaller quadrants.

In one embodiment, each microchannel of a microfluidic chip is associated with a set of quadrants, such that observations in that set of quadrants may be linked to events in that microchannel. In some embodiment, subdivisions may be located so that each microchannel is located in one set of subdivided quadrants. It is not meant that each microchannel is limited to one Tile. Thus, in some embodiments, there is more than one Tile associated with each microchannel, such that each microchannel may have more than one Tile associated with the channel, including but not limited to the collection area(s)s for that microchannel.

Figure 31A:
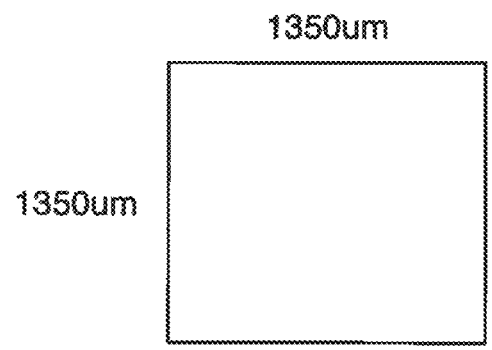
FIGS. 31A-B show exemplary schematic diagrams of Tile Areas and quadrants representing fields of view, e.g. one embodiment for analyzing events in microfluidic channels, showing fields of view (FOV) as observed when viewed through an optical system including but not limited to an Olympus Light Microscope. The field of view is determined by the field captured by the camera or the ocular.
Figure 31B:
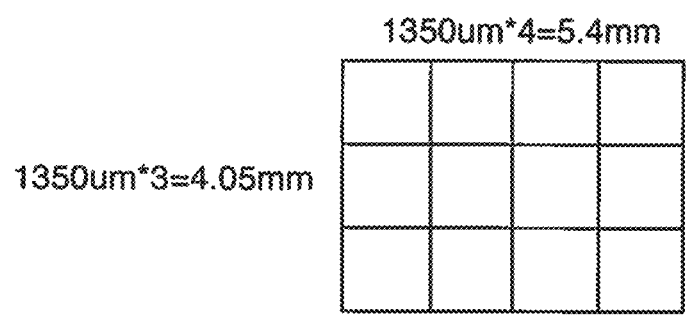

FIGS. 31A-B show exemplary schematic diagrams of Tile Areas and quadrants representing fields of view, e.g. one embodiment for analyzing events in microfluidic channels, showing fields of view (FOV) as observed when viewed through an optical system including but not limited to an Olympus Light Microscope. FIG. 31A shows an outline representing one field of view (FOV) on a microscope stage, when viewed using a 10× ocular, e.g. a 1350 um by 1350 um area, i.e. one Tile Area as viewed with an Olympus Light Microscope. FIG. 31B shows an exemplary representation of the total viewing area (e.g. as determined by the range of motion of the stage controls) where the total viewing area includes but is not limited to 12 Tile Areas, e.g. 12 quadrants, for a total view area 5.4 mm wide and 4.05 mm in length, wherein each Tile Area or quadrant representing one FOV. In one embodiment, twelve (12) tiles are contemplated for viewing in under a 30 sec frame rate limit (1 frame every 30 seconds) for photography, including but not limited to videophotography, of events occurring within at least one active region in a microchannel.

Thus, in some embodiments, microfluidic chips described herein, further comprise Tile for providing a means, in part, to compare events in identical locations within each microchannel for making comparisons between samples. In other words, any microfluidic chip described herein may further comprise a Tile, e.g. a 12 Tile.

XI. Variations of Microfluidic Devices.

In some embodiments, the microfluidic device are contemplated to have a semi-permeable membrane to separate the fluidic part of the device from a juxtaposed channel or chamber having live mesenchymal and/or epithelia and parenchymal cells. This setup is desirable when the goal of the investigation is to understand the effect of multiple cell types or the effect on the blood behavior of mesenchymal, epithelial and parenchymal cells in response to external stimuli and stresses.

The cells retained in the membrane region of the device, where cells that can communicate through the membrane with the cells seeded into the juxtaposed channel or chamber.

XIII. Further Embodiments of Additive Channel Designs for Use as Microfluidic Chip Devices.

Several designs are contemplated for microfluidic Vessel-On-Chips, for use in analyzing blood clotting. Goal: Design more efficient chip to allow higher throughput testing of various blood conditions. In some embodiments, such chips have endothelial cells, e.g. HUVACs. In some embodiments, such chips do not contain endothelial cells.

In some embodiments, chips may have a single microchannel per sample. It is not intended to limit one sample to one microchannel per sample. Indeed, in some embodiments, chips may have two or more microchannels per sample for providing duplicates.

Figure 32A:
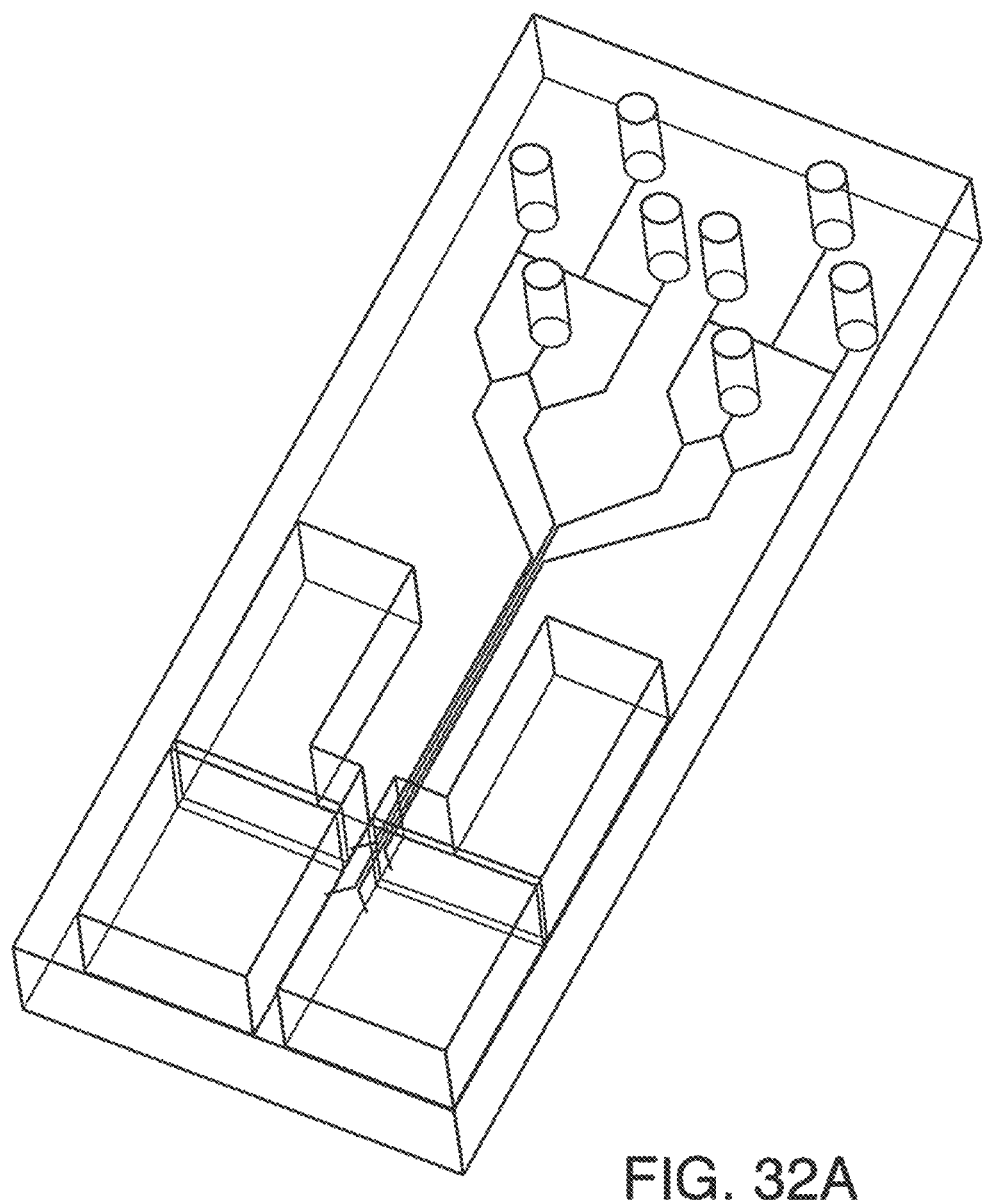
FIGS. 32A-C show exemplary schematic diagrams of one embodiment of a microfluidic chip having 4 channels on one chip.
Figures 32B, 32C:
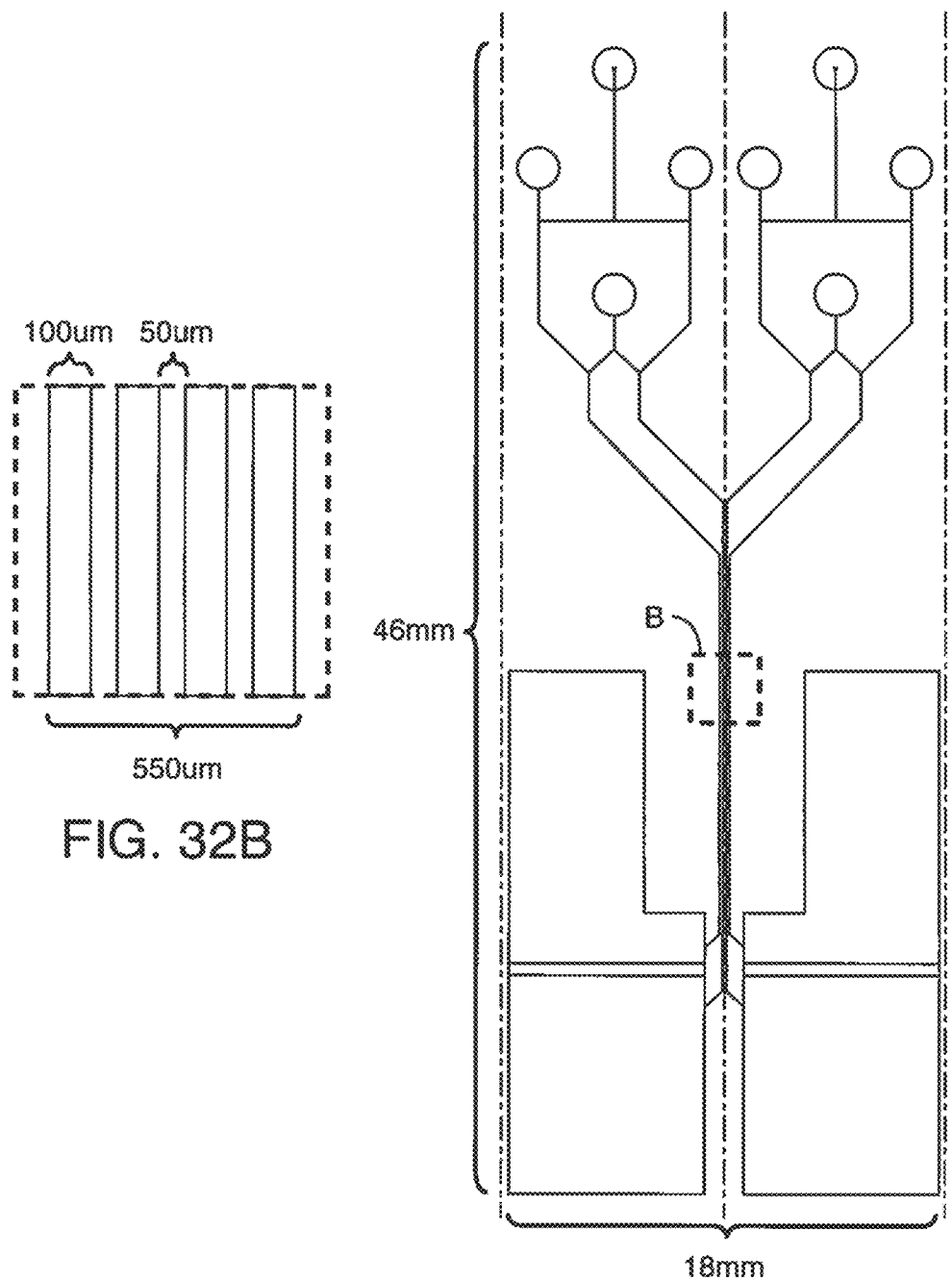

FIG. 32A-C shows an exemplary schematic diagram of one embodiment of a microfluidic-chip as 4 total channels on one chip. The four channels have exemplary dimensions of 100 um diameter channels spaced 50 um apart for providing an area such that all four channels may be viewed under a microscope, for one example, within one microscopic field of view. Alternatively, increase channel width to 200 um and test two conditions at once, for one example, within one microscopic field of view.

Figure 33:
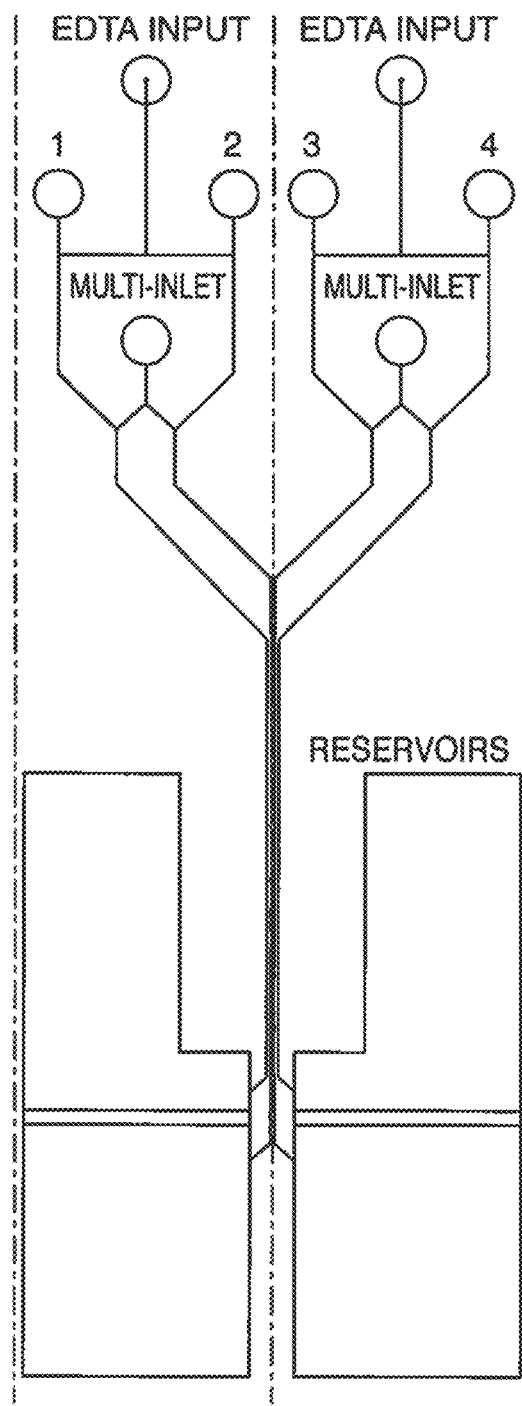
FIG. 33 shows an exemplary schematic diagram of features in one embodiment of a 4 channel chip. The numbers 1, 2, 3 and 4 (numbers next to dots) represent inlet/outlet ports for attaching to other components, including but not limited to tubing, e.g. for adding or removing fluids, pump (s) or other devices for inducing negative or positive pressure. Each port may be attached to separate or shared channel control(s), as described herein. Multi-inlets (represented by 2 lower dots) are located opposite the EDTA inputs (2 upper dots). In one embodiment, multi-inlets refer to inlets for cell seeding, cell rinsing, e.g using buffered solutions, media, common liquids used in cell culturing, and the like. It is not meant to limit the multi-inlets to inflowing fluids. In some embodiments, Multi-inlets are used for collecting outflowing fluids, e.g. cell media, samples, etc. In one exemplary embodiment, gravity driven flow for anticoagulants, e.g. EDTA solutions, added into the EDTA input, provides pressure (gravity) forces for pulsing EDTA into single additive channels below, in order to eliminate blood clotting in outflow from inlet/outlet ports for collecting and analyzing samples into the reservoirs. Thus in one embodiment, outflow to the reservoirs is collected from one or more inlet/outlet ports. On chip reservoirs are shown as blocked in the lower part of the drawing. As one example for providing pressure forces for pushing sample from the reservoirs through channels into the upper portion of the device, height of the reservoirs provides such pressure. For one example, four reservoirs are shown, each having >70 mm^ area. In one embodiment, a PDMS device height is 15 mm with a volume >1 mL. Black lines represent branches and microchannels, black dots represent locations where 2 branches microchannels merge into one, or where the microchannels connect to a reservoir, in one embodiment, one reservoir is connected to each (one) channel. It is not intended that the use of multi-inlets apply just to seeding ports and output ports, but also to the anticoagulant ports (EDTA), calcium ports, and sample/blood ports.

FIG. 33 shows an exemplary schematic diagram of features in one embodiment of a 4 channel chip. The numbers 1, 2, 3 and 4 (numbers next to dots) represent inlet/outlet ports for attaching to other components, including but not limited to tubing, e.g. for adding or removing fluids, pump(s) or other devices for inducing negative or positive pressure. Each port may be attached to separate or shared channel control(s), as described herein. Multi-inlets (represented by 2 lower dots) are located opposite the EDTA inputs (2 upper dots). In one embodiment, multi-inlets refer to inlets for cell seeding, cell rinsing, e.g. using buffered solutions, media, common liquids used in cell culturing, and the like. It is not meant to limit the multi-inlets to inflowing fluids. In some embodiments, Multi-inlets are used for collecting outflowing fluids, e.g. cell media, samples, etc. In one exemplary embodiment, gravity driven flow for anticoagulants, e.g. EDTA solutions, added into the EDTA input, provides pressure (gravity) forces for pulsing EDTA into single additive channels below, in order to eliminate blood clotting in outflow from inlet/outlet ports for collecting and analyzing samples into the reservoirs. Thus in one embodiment, outflow to the reservoirs is collected from one or more inlet/outlet ports. On chip reservoirs are shown in the lower part of the drawing. As one example for providing pressure forces for pushing sample from the reservoirs through channels into the upper portion of the device, height of the reservoirs provides such pressure. For one example, four reservoirs are shown, each having >70 mm^ area. In one embodiment, a PDMS device height is 15 mm with a volume>1 mL. The lines represent branches and microchannels, black dots represent locations where 2 branches microchannels merge into one, or where the microchannels connect to a reservoir, in one embodiment, one reservoir is connected to each (one) channel.

Figure 34:
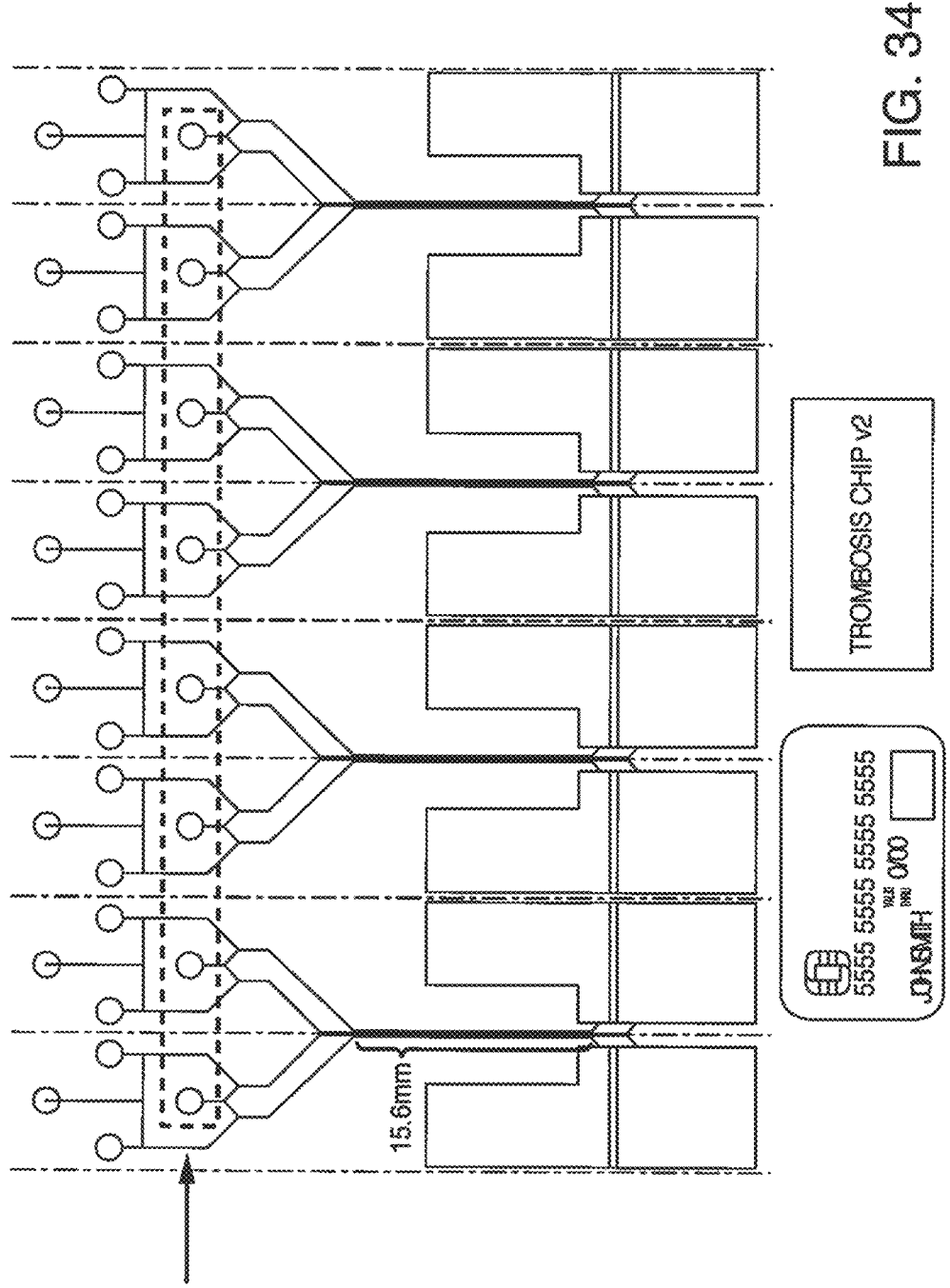
FIG. 34 shows an exemplary schematic diagram of one embodiment of a microfluidic chip device as 16 total channels on one chip device. The arrow points to a region containing sample input ports spaced for use with a multi-channel pipettor, i.e. each port corresponds to the dispensing end of the pipette tip, for simultaneously adding samples in each input port. One exemplary embodiment shows microchannels 15.6 mm in length. A chip device size comparison is shown at the bottom with a regular sized American credit card on the left compared to the chip device outline shown on the right.

As one example, FIG. 34 shows an exemplary schematic diagram of one embodiment of a Thrombosis-On-Chip as 16 total channels on one chip; 15.6 mm middle length same as lung-on-chip ~80 mm wide×50 mm high. A credit card (left) is shown for a size comparison. The arrow points to milt-inlet spacing which corresponds to multi pipette spacing. In other words, Multi-inlets are spaced 9 mm apart, which is the same spacing as 96-well plate where a multi-pipette may be used for inserting samples and/or solutions. Save significant amount of time with seeding/feeding cells and imaging.

FIG. 34 shows an exemplary schematic diagram of one embodiment of a microfluidic chip device as 16 total channels on one chip device. The arrow points to a region containing sample input ports spaced for use with a multi-channel pipetter, i.e. each port corresponds to the dispensing end of the pipette tip, for simultaneously adding samples in each input port. One exemplary embodiment shows microchannels 15.6 mm in length. A chip device size comparison is shown at the bottom with a regular sized American credit card on the left compared to the chip device outline shown on the right.

A. Exemplary Features for Use in Embodiments of a Microfluidic Chip Device.

In yet another embodiment of a microfluidic chip device, features include but are not limited to inlets and outlets for pumps, in part for providing separate channel fluid flow control, represented at numbers and circles as inlet/outlet ports on FIG. 33; multi-purpose inlets, i.e. multi-inlets, for cell seeding, rinsing, adding and removing common liquids, such as collagen for coating channels, cell media, cell treatments, e.g. cytokines, etc., represented as circles/ports on FIG. 33; EDTA input ports, for adding anticoagulants, etc., represented as circles/ports on FIG. 33; and on chip reservoirs, represented as blocked squares on FIG. 33.

In some embodiments, an EDTA input is located on the upper side of a chip such that gravity drives EDTA flow, in part for reducing the number of pump channels required for use on the entire chip. One (1), 2, 3 and 4 corresponds to 4 different devices used in a single experiment. Thus, advantages include but are not limited to sharing EDTA ports between constructs (reducing the need for additional pumps and/or pumping systems); joint seeding/washing/reagent ports, since the different constructs have to be prepared similarly (for example, seeding channels with endothelial cells at the same time).

The aim is to reduce the number of EDTA ports and, in turn, the complexity of interfacing with and driving many EDTA ports. However, when a single port is used to drive additive channel to several constructs, the flow rates in the additive channels may end up different. However this difference is undesirable, since a certain EDTA concentration should be the same in all outputs because a certain EDTA level is desired to prevent coagulation. In one embodiment, an EDTA concentration is 10 uM. In one embodiment, a single EDTA input drives a similar flowrate into each channel, thus the channel resistance is equal. In one embodiment, the channel lengths are equal. In one embodiment, resistors may be used for providing a similar, and in some embodiments, an equal flow rate between channels on a device.

Resistors and Regulators:

In one embodiment, a device comprises one input pressure regulator. In one embodiment, a device comprises two (or more) input pressure regulators. In one embodiment, a device having additive channels for both input (calcium) and output (EDTA) has three input regulators. In one embodiment, the flowrate of calcium should be a specific fraction of the flowrate of input blood and the output. In one embodiment, the EDTA flowrate is a specific fraction of the output flow rate.

In one embodiment, a pressure regulator pressurizes two reservoirs at once (e.g. we can divide a current device reservoir into two sections). In one embodiment, one of these reservoirs/sections would be for the input blood, the other for calcium. In one embodiment, resistors are used in the device, e.g. Pod, for the inlet. In one embodiment, an additional resistor is used for the calcium. In one embodiment, the resisters provide a single applied pressure to drive flow in two channels (e.g. blood and calcium), with the ratio of resistances will ensure that the two flowrates are at a specific ratio to each other.

For example: a single pressure source on a blood inlet plus a calcium inlet; a single pressure source on calcium inlet plus EDTA inlet and; a single pressure source on three inlets: blood, calcium, EDTA.

In one embodiment, the use of on-chip reservoirs are contemplated to overcome the material-compatibility of non-anticoagulated blood.

FIG. 33 shows an exemplary schematic diagram of features on one embodiment of a 4 channel chip. Inlets/outlets for pump/separate channel control are shown as 1, 2, 3 and 4 (numbers and dots). Multi-inlets refer to inlets for cell seeding/rinsing, common liquids. EDTA inputs. Gravity driven flow for EDTA to eliminate blood clotting for outflow collection. On chip reservoirs. Four reservoirs, all >70 mm^ area. When PDMS device height is 15 mm then volume >1 mL. Black lines represent microchannels, showing locations where 2 microchannels merge into one, or where the microchannels connect to a reservoir, in one embodiment, one reservoir is connected to each (one) channel.

B. Exemplary Methods for Using One Embodiment of a Microfluidic Chip Device.

An exemplary method of loading and using a microfluidic chip device is provided for a 4 channel device, such as shown in FIG. 33. To begin loading a device, plug EDTA inputs, and other open ports, such as ports labeled 1, 2, 3, 4 in FIGS. 35A-C and 36A-C.

Thus in one embodiment, unplug EDTA input for providing an outlet for analysis of outflowing fluid. In one embodiment, pressure from reservoir, provides pressure force sufficient to push or drive fluid through the channels. In one embodiment, height of reservoir, provides pressure force sufficient to push or drive fluid through the channels.

In some embodiments, flow is unidirectional. For example, a biological sample (e.g. blood or blood components, or other sample) enters the microfluidic device on one end and proceeds to flow in one direction to the outlet. In some embodiments, flow is bi-directional. For example, cell seeding (e.g. seeding of endothelial cells) might proceed from an inlet to an active region, growth region, or imaging region; however, a biological sample might proceed in the opposite direction (e.g. blood from an integrated, on-chip reservoir moving into the active region or imaging region from the other side of the chip).

Figure 35C:
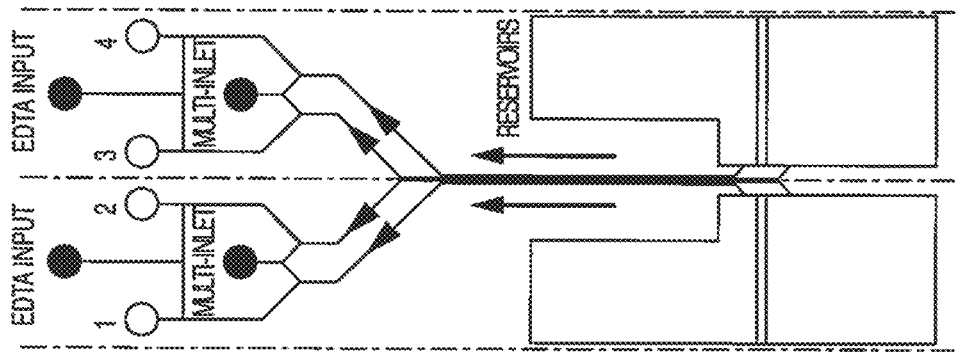
FIG. 35A-C shows exemplary schematic diagrams of one embodiment of a microfluidic chip device related to methods of use.
Figure 35B:
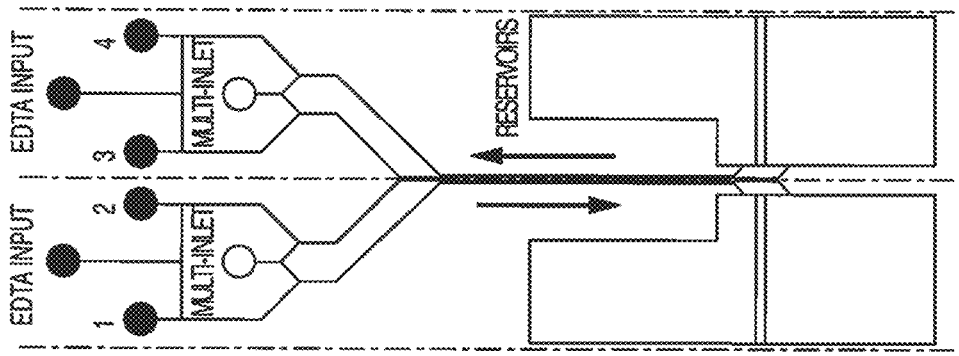
Figure 35A:
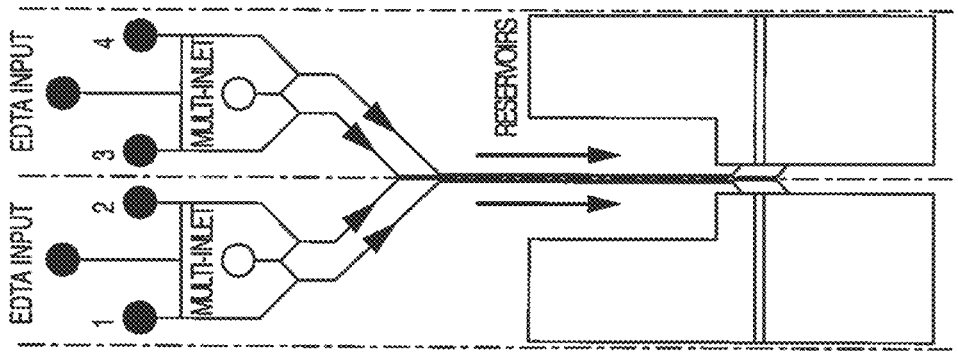

FIG. 35A-C shows exemplary schematic diagrams of one embodiment of a microfluidic chip device related to methods of use. FIG. 35A shows an exemplary schematic diagram of a device during cell seeding, where positive pressure, shown by the thick arrows pointing down representing the direction of fluid flow, is used to seed cells into channels, where cells are seeded into the multi-inlets while the other ports, 1, 2, 3, 4 and EDTA input are plugged (black circles), followed by cell attachment to the microchannels. Afterwards, medium is pushed through to rinse channels, see arrowheads in channels/branches between ports and the microchannles. FIG. 35B shows an exemplary schematic diagram of fluid flow in a device during cell feeding. Medium is added to reservoirs, using 200 ul pipette tips filled with medium inside multi-inlets, which additionally serve as plugs during feeding. Pressure used to push medium may be positive pressure represented by the arrow pointing down, in other embodiments the pressure is negative pressure represented by the arrow pointing up. FIG. 35C shows an exemplary schematic diagram of fluid flow in a device during chip prep, where 1, 2, 3, and 4 numbered ports are unplugged, while EDTA inlets and multi-inlet ports are plugged. Negative pressure (see direction upwards of thick arrows) is used to fill empty upper channels, then multi-inlets are also plugged. After filling, tubing is attached to inlets 1, 2, 3, and 4 of which at least one tube is attached to a pump.

Figure 36C:
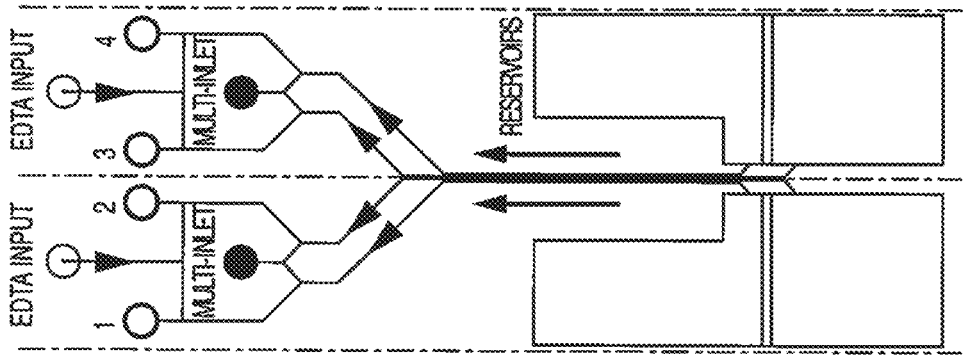
FIG. 36A-C shows exemplary schematic diagrams of one embodiment of a microfluidic chip during blood testing.
Figure 36B:
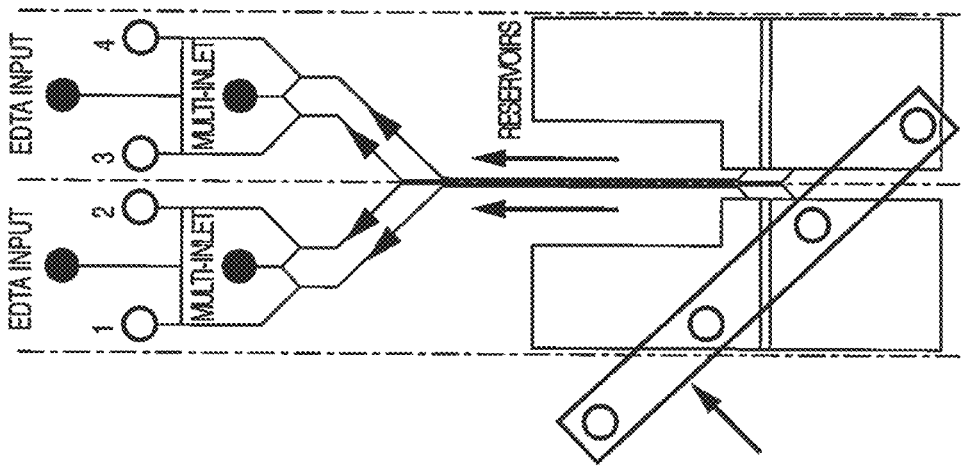
Figure 36A:
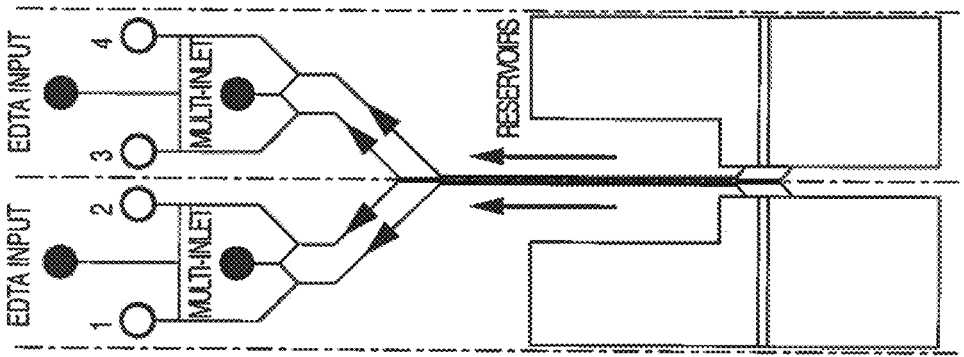

FIG. 36A-C shows exemplary schematic diagrams of one embodiment of a microfluidic chip during blood testing. FIG. 36A shows an exemplary diagram showing where blood is added to reservoirs along with any test agents. Thick arrows show the direction of fluid flow of blood out of the reservoirs, with smaller arrowheads showing the direction of flow upwards towards the inlets. FIG. 36B shows an exemplary diagram where the four open dots, shown diagonally within the open rectangle (arrow), represent the open (dispensing) ends of pipette tips where the other tip end is attached to a multi-pipetter so that fluid containing an agent, such as a conditional agent, e.g. a coagulation reagent in solution, such as Ca++, intended for adding to blood entering the test channels, is simultaneously added to three ports located below the three lower dots, one port each for three of the four reservoirs shown as black areas in the lower part of the chip, where each of the four microchannels is in fluidic communication with a corresponding reservoir. Thus, the solution is mixed into the blood contained in three reservoirs at one time. The remaining reservoir, when receiving a solution as a separate addition into the fourth reservoir port, not in line with the multi-channel pipette tips, upper right, is added/mixed separately from the other three reservoirs. In some embodiments, this fourth reservoir is used as a control without the addition of an agent in solution, such as a conditioning solution. FIG. 36C shows an exemplary diagram for preparing Outflow fluid for collection. Unplug EDTA input ports (dots at the top of the diagram), insert the dispensing end of 1 mL syringes for adding EDTA solution. Since a small amount of EDTA needed, flow downward is gravity driven, see arrowhead pointing down from the input. Each cm of liquid height=0.1 kPa in pressure; so that an optimal height of the on-chip device components is calculated for each type of chip.

As an example of a method of using a chip, one embodiment of the protocol might comprise the steps of: plug EDTA inputs, and inlet/outlets 1, 2, 3, and 4. Day 1: Cell growth and maintenance: Seeding: Using positive pressure, a solution containing cells are inserted into, e.g. flowed into a port, for seeding cells into channels; observe cell attachment; then push medium through to rinse channels; and cell feeding: Add medium to reservoirs, leave 200 ul pipette tips filled with medium inside multi-inlets. Can either use positive or negative pressure.

Day 2: Chip testing using microscope observations: unplug 1, 2, 3, and 4, then use negative pressure to fill up upper channels; plug multi-inlets. Attach tubing to inlets 1, 2, 3, and 4, and to a pump. For testing a sample, such as blood, add sample with desired agents, such as blood mixed with a test agent, e.g. an anticoagulation antibody. Then add a solution for inducing coagulation, such as into ports shown in FIG. 36B.

VIX. Dimensions and Spacing of Fluidic Microchannels for Embodiments of a Vessel-On-Chip.

It is not intended that the present invention be limited to only certain dimensions for the microfluidic channels. In one embodiment, the width of a microfluidic channel is 250 um in a microfluidic Vessel-On-Chip. It is not meant to limit the width of a microfluidic channel. For example, in other embodiments; the width of a microfluidic channel is 400 um. In yet other embodiments, where more than one channel is present in a chip, the width of microfluidic channels are different, for example, a combination of 250 um channel width and 400 um channel width in a microfluidic Vessel-On-Chip.

Accordingly, in one exemplary embodiment, the spacing between channels is 200 um channel spacing for a 4-channel chip. As one non-limiting example, a 4-channel chip comprises 250 um channel widths with 200 um channel spacing between channels.

Figure 37:
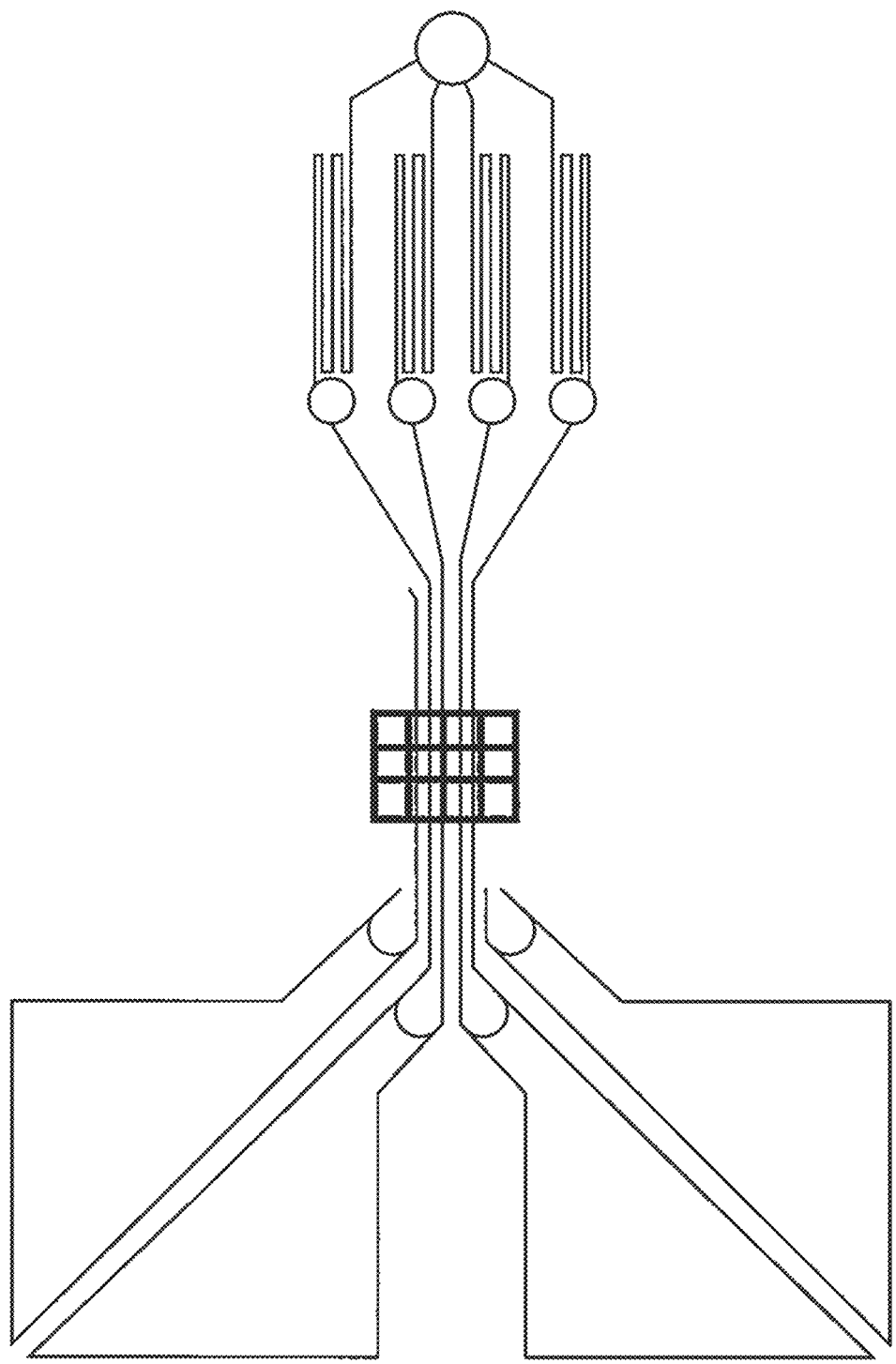
FIG. 37 shows an exemplary schematic diagram of one embodiment of a microfluidic chip as a four channel device. In this embodiment, a single input port (shown by the circle at the top of the diagram-upper arrowhead) is connected to four branching channels flowing through resistors (located in between the components identified by the upper two arrowheads) for regulating the fluidic flow rated for providing equal flow rates of fluids entering each of the four microchannels. Dots located after the resistors (middle arrowhead) represents each inlet per microchannel. The center black lines (as shown in detail in FIG. 31B), represents a side by side viewing area, in part for use in analyzing (including but limited to observing) events occurring in parallel active regions of the microchannels. The lower blocked rectangles (lower arrowhead) represents on-chip reservoirs where one reservoir is in fluidic communication with one of the microchannels. In a preferred embodiment, the dot at the very top is a common calcium port and the four circles are the blood inlets. This allows the calcium reagent to be the same across different test conditions, while the different sample inlets allow the testing of blood from different patients, or blood from same patient pre-mixed with different concentrations of a drug. The four resistors make sure that the same flow rate of calcium goes to all four test conditions.

As one illustrative example, FIG. 37 shows an exemplary schematic diagram of one embodiment of a Thrombosis-On-Chip as a 4 Additive Channel Design showing a side by side viewing area as detailed in FIG. 30B. In one embodiment, a 4 Additive Channel Design comprises 4 reservoirs feeding (i.e. in fluidic communication) into 1 channel each.

Accordingly, in one exemplary embodiment, the spacing between channels is 200 um channel spacing for a 8-channel chip. As one non-limiting example, an 8-channel chip comprises 250 um channel widths with 200 um channel spacing between channels.

As one example, FIG. 38 shows an exemplary schematic diagram of one embodiment of a Thrombosis-On-Chip as an 8 Additive Channel Design showing a side by side tile viewing area.

The arrow on the upper left points to 4 reservoirs that feed (i.e. fluidically connected) into 2 channels, one channel each for a duplicate. The arrow on the middle left points to 8 outlets to collect individual samples. These 8 outlets may also be used as 8 inlets (circles) for cell seeding/conditional testing (e.g. TNF conditioning). The arrow on the middle left points to a single EDTA inlet feeding 8 channels with resistors to equalize flow rate (e.g. separate pump connected) contemplated for use in infusion of EDTA. It is not meant to limit the number of EDTA inlets. Thus, in some embodiments, an 8 channel Additive Channel design may have two EDTA inlets, each feeding 4 channels. It is not meant to limit the EDTA inlet to EDTA, indeed any anticoagulant in addition to EDTA may find use for adding to the EDTA inlet The arrow on the right shows a microscopic viewing area as a Tile.

EXPERIMENTAL

Example 1

Materials And Methods

This example describes exemplary materials and methods used during the development of the present inventions.

Microfluidic Chip Manufacturing And Surface Activation:

Chip design and fabrication as used herein, were initially modified versions of previously described chips (See, Huh, D. et al. Microfabrication of human organs-on-chips. *Nat. Protoc.* 8:2135-2157 (2013). In further embodiments, chip designs used herein and contemplated chip designs are unlike previously published chips.

In one embodiment, the surface area of the vascular compartment of a microfluidic chip used herein is greater in comparison to the original lung-on-a-chip design because the original size was too small for optimal blood component interaction with endothelium. As described herein, a 1 mm wide and 200 µm tall chamber provided an increase in size of the vascular surface area exposed to laminar flow, as compared to an exemplary lung-on-chip. An anticoagulant port, referred to by several names, including but not limited to EDTA input, citrate input, etc., was added near the outflow port of the vascular chamber. Thus two ports (anticoagulant port and vascular outflow i.e. outflow) were linked through a microfluidic channel (dimension of 250 um wide by 100 um height) to allow for perfusion of anticoagulant solution during the experiment. In some embodiments, modifications were made in the coagulant port dimension. The outlet of the chip was connected to a pulling syringe pump with a system of tubing and connectors made of medical grade silicon that excludes any metal components or potential causes of platelet activation.

Before cell seeding, chips were sterilized by autoclaving followed by functionalizing the polydimethylsiloxane (PDMS) surface using oxygen plasma treatment (100 W, 15 sccm, 40 s; PlasmaEtcher PE-100, Plasma Etch, Reno, Nev.) afterward incubating with 1% (3-aminopropyl)-trimethoxysilane (APTMES; Sigma) in 100% anhydrous alcohol (Sigma) for 20 min at room temperature, flushed twice with 70% ethanol and twice with water before curing overnight at 60° C.

Cell Culture and Microfluidic Chip Preparation:

After PDMS surface functionalization and curing, the entire chamber was coated with extracellular matrix (ECM) consisting of a mixture of rat tail collagen I (100 µg/ml in phosphate buffered saline (PBS); BD Biosciences) and fibronectin (30 µg/ml in PBS; BD Biosciences) incubated at 37° C. for 2 hours before washing with PBS.

In order to minimize the biological variability of endothelial cells, two fresh vials (passage 1) of Human Umbilical Vein Endothelial Cells from pooled donors (HUVECs, Lonza, Inc., catalog number C2519A, accessed Jun. 5, 2017) were thawed at the start of the study. These HUVECs were cultured in Endothelial Growth Medium-2 (EGMTW-2 BulletKit™, Lonza, Inc., catalog number CC-3162, accessed Jun. 5, 2017) and passaged twice before being frozen at passage 3.

At the start of each experiment, two vials of cells were thawed and expanded for 3 days in EGM-2. Cells were gently detached with 0.05% Trypsin (BD Biosciences, 2-4 minutes incubation at room temperature) and $8 \times 10^6$ cells/ml were introduced into the ECM-coated microchannels. After incubating for 30 minutes at 37° C., cell attachment to the bottom surface of the chamber was assessed by microscopy. Then, a second flask of HUVECs was trypsinized and used to seed the upper surface of the microfluidic chamber by introducing the cell suspension, inverting the chip, and incubating at 37° C. for 30 minutes. Each microfluidic chamber was gently flushed with EGM-2 twice in order to remove unbound cells, then chips were incubated overnight at 37° C. The next day, chips were connected to a syringe pump (Chemyx Fusion 200) and perfused with EGM-2 for 3 days (30 µL/hr) to provide continuous supply of fresh media. On day 3, medium was switched to EGM-2 with low serum (1% FBS, no VEGF) to promote cell synchronization overnight. On day 4, chips were used for blood perfusion experiments.

Cell-Monolayer Integrity:

Transmission light microscopy was routinely used to assess cell-monolayer integrity prior to each experiment. Before every experiment, each one of the endothelialized channels was inspected via light microscopy. Samples showing any sign of discontinuity in the endothelium were discarded.

Vascular Leakage Assay as Test for Tissue Integrity:

The ability of cells to form a confluent monolayer was monitored for one week measuring vascular leakage of dextran (ThermoFisher). In order to measure vascular leakage the vascular channel was perfused with cell culture medium containing fluorescent dextran-cascade blue (3 kDa, ThermoFisher). The apical compartment was perfused with plain medium (without FBS). At various time points, the effluent from the chip was collected, and the relative fluorescence of the top and bottom compartments were measured using a standard plate reader. The endothelial cell monolayer was observed to remain stable to at least 6 days post-seeding.

TNF-Alpha Stimulation:

In some experiment endothelial cells were stimulate with 50 ng/ml of TNF (Sigma) for 6 hours in order to induce vascular inflammation before blood perfusion.

Experiments with Blood: Blood Samples and Endothelium:

Citrated human blood (Research Blood Components, Cambridge, Mass.) was used within 4 hours of a blood draw in order to minimize pre-analytical effects on platelet function. Before every experiment, each one of the endothelialized channels (i.e. microchannels having an endothelial cell layer) was inspected via light microscopy. Samples showing any sign of discontinuity in the endothelium were discarded.

Agents Added to Blood:

Blood incubated with combined sCD40L/hu5C8, IC or 10 ng/ml of soluble collagen (Soluble Calf Skin, Type I-C/N 101562, BIO/DATA, Corporation, Horsham, Pa. USA) was at room temperature for 20 minutes.

Cloning, Expression and Purification:

Generation of IgG2σ was previously described (Vafa, O. et al. An engineered Fc variant of an IgG eliminates all immune effector functions via structural perturbations. *Methods* 65:114-126 (2014)). 5c8 human IgG1 and human IgG2-Sigma Fc variants were produced in Sino Biological Inc. Gene fragments encoding the 5c8 heavy and light chains were synthesized and cloned into mammalian expression vectors. DNA was produced and used in transient transfections with HEK293. Antibodies were purified using Protein A affinity chromatography and formulated in phosphate-buffered saline (DPBS), pH 7.4.

Blood Pre-treatment and Perfusion: Formation of IC (Preformed IC):

Hu5C8, IgG2σ (control) (both provided by Janssen or provided as described herein) For studies with preformed IC, Hu5C8 or IgG2σ as an isotype control were combined with sCD40L (Tonbo Biosciences, San Diego, Calif.) in PBS, in a ratio of 1 molecule of sCD40L to 3000 molecules of antibody. After 20 minutes incubation at room temperature, the solution was diluted in a blood sample to reach the final concentration of 240 µg/ml (Hu5C8) and 10 ng/ml (sCD40L).

Platelets:

Platelets were labeled with human CD41-PE antibody (10 µL/ml, Invitrogen) directly added to the blood and incubated at room temperature for 5 minutes.

Platelet Aggregation/Activation:

As an exemplary thrombosis inducing agent, 15 µg/ml of sCollagen (BIODATA) was used to promote platelet aggregation (Huh, D. et. al. A Human Disease Model of Drug Toxicity-Induced Pulmonary Edema in a Lung-on-a-Chip Microdevice. *Sci. Transl. Med.* 4, 159ra147-159ra147 (2012).

Anticoagulant Drug:

As an exemplary standard antiplatelet (anticoagulant) drug, Eptifibatide was used as described herein. Eptifibatide has a well-known mechanism of action, such that a bolus of 180 mcg/Kg is frequently used to treat human patients.[54] We estimated that a concentration of 2.4 µM (about 2 µg/ml) is a clinical relevant concentration. As described herein for experiments including Eptifibatide, 2 µg/ml of Eptifibatide were incubated with blood samples for 15 minutes at room temperature before adding sCollagen or before flowing through TNF-inflamed biomimetic vessel.

Adding Blood to a Vessel-On-Chin and Flow Conditions:

A medical grade plastic reservoir was mounted on the chip, then 800 µl of the blood sample was pipetted into the reservoir. The chip was perfused with the blood by withdrawing it at a rate of 60 µl/minute using a syringe pump. The citrated blood was re-calcified 2 minutes after the beginning of each experiment by adding 100 µl/ml of a solution containing 100 mM calcium chloride and 75 mM magnesium chloride to the blood to permit calcium- and magnesium-dependent platelet function and coagulation.

Visualizing Fibrin Deposition:

When analyzing the formation of fibrin, 10 g/ml of fluorescently labeled fibrinogen (Alexa 488, Invitrogen) was also added to the blood. While fluorescent fibrinogen was barely detected as a diffused fluorescence, fibrin deposition on inflamed cells and sparse clots was easily distinguished since fibrin formed filamentous structures produce a signal intensity that is clearly observed above a background threshold.

Staining of Endothelial Cells:

Samples were washed twice in cell culture medium and then fixed in acetone/methanol 1:1 at −20° C. for 10 minutes. Each sample was then washed three times in PBS and incubated in blocking solution consisting of PBS and 10% normal donkey serum (Abcam) for one hour. After blocking, samples were washed in PBS twice and then incubated with anti VE-Cadherin monoclonal antibody (Abcam) diluted 1:100 in blocking solution at 4° C. overnight. The next day, samples were washed twice in PBS and incubated for 2 hours at room temperature with secondary Alexa Fluor 488 donkey anti-rabbit antibody (Abcam) diluted in PBS then washed twice in PBS. Finally Hoechst (Abeam) was used to stain cell nuclei at room temperature for 5 minutes, then samples were washed twice in PBS before being imaged.

Fluorescence Image Analysis:

Chips perfused with blood samples were immediately imaged via fluorescence microscopy (Olympus IX83, 10× objective UPLFLN10×2, Orca-Flash4.0 CMOS Camera). Each chamber was inspected along its entire length and S images (about 0.25 cm) were captured from the central area of the chamber. Image processing and quantification was performed with an automatic macro compiled in ImageJ and numerical values corresponding to platelet coverage or fibrin florescence were collected and statistically analyzed in Graphpad Prism V7.

Platelet Coverage:

A percentage of signal coverage (or Platelet coverage) was computed from the binary image as the ratio of bright pixels to the total number of pixels in the image. Image processing and quantification was performed with an automatic macro compiled in ImageJ in order to ensure unbiased signal measurements. Numerical values corresponding to platelet coverage or fibrin fluorescence (signal intensity) were collected and statistically analyzed in Graphpad Prism V7.

Scanning Electron Microscopy Sample Pre-Treatment and Imaging:

Immediately after fluorescence imaging, the chips were fixed in 2.5% glutaraldehyde in 100 mM sodium cacodylate buffer for 2 hours at room temperature. Then, the samples were washed and post fixed in 1% osmium tetroxide for 1 hour at room temperature. After the postfixation, the samples were dehydrated in series dilutions of ethanol and finally completely dried in a Critical point dryer (Tousimus Autosamsri-815). After mounting, the samples were gold sputtered using a Sputter coating system (Hummer 6.2) and imaged by SEM (Jeol 5600LV).

Thrombin-Anti Thrombin (TAT) Measurement Via ELISA:

Thrombin Anti-Thrombin (TAT) levels were analyzed in plasma from blood flowing out of the chip device by removing a sample from the outflow port. Thus TAT levels were evaluated in sample effluents collected from the outflow port of the chip using the Human TAT ELISA Kit (Siemens Healthineers) according to the user manual.

Gene Expression Analysis:

Total RNA was isolated from the chip using RNA Mini kit (Fisher Scientific). Two step qPCR was performed using SuperScript IV Synthesis System (Fisher Scientific) and TaqMan Master mix (Fisher Scientific) in QuantStudio3 PCR System (Fisher Scientific). Relative expression of gene was calculated using $2^{-\Delta\Delta C_t}$ methods.

Statistical Analysis:

The data are presented as mean±standard error of the mean (s.e.m.). and P values were obtained (via ANOVA) to compare the means of at least n=3 independent experiments. Data analysis was performed using Graphpad Prism V7 (* p<0.0001,  p<0.001, * p<0.05).

Example 2

Endothelial Cells Control Clotting in the Vessel-On-Chip

This example describes exemplary clotting on the chip that is controlled by endothelial cells.

sCollagen treatment of blood activates blood components while endothelial pre-treatment with TNF-α mimics (simulates) tissue inflammation. Therefore, sCollagen treated blood was added to a Vessel-On-Chip containing TNF-alpha pre-treated endothelial cells (endothelium), for simulating inflammation.

More specifically, TNF-α (50 ng/ml) was added to a Vessel-On-Chip for contact with the endothelium for 6 hours of incubation. Soluble collagen (sCollagen), a standard platelet activator, was used at 10 µg/ml for treating blood samples, either prior to adding to a Vessel-On-Chip or through an additive channel attached to an intake port as the blood sample is being added to the intake port.

The use of TNF-α or sCollagen treatments on thrombosis in a Vessel-On-Chip led to more aggressive patterns of platelet aggregation and fibrin deposition on the endothelium, as demonstrated by increased areas of platelet coverage and fibrin signal intensity (FIG. 18E, upper and lower charts, respectively). Diverse structural characteristics of blood clots induced by the two experimental stimuli were captured via scanning electron microscopy (SEM) as colored images in FIG. 18D. In particular, TNF-α pre-treatment of the vascular endothelium induced formation of compact clots composed of red blood cells and platelets, surrounded by fibrin (FIG. 18D, TNF-α).

In contrast, thrombosis by sCollagen involves direct activation of the classic intrinsic coagulation pathway, which leads to general fibrin formation and parallel activation of platelets by binding of sCollagen to their integrin receptor α2β1[41]. Blood incubated with sCollagen formed a meshwork of complex fibrin-rich clots that incorporated red blood cells and platelets FIG. 18D, sCollagen). Additionally, the remarkable alteration of red blood cell morphology (FIG. 18D, sCollagen) is known to be associated with retraction of fibrin during later stages of blood clotting[42,43]. The SEM images provide convincing evidence of de novo formation of fibrin-rich clots in vitro, a relevant pathophysiological endpoint for thrombosis.

These differences are consistent with the mechanism for thrombosis by both agents, i.e. thrombosis by TNF-α is primarily driven by activation of the endothelium and release of factors that promote adhesion and platelet-to-platelet interactions which then leads to local thrombin activation, fibrin formation and clot stabilization[40].

Example 3

Testing the Use of an Additive Channel in a Vessel-On-Chip for On-Chip Biomarker Assessment and Treatment with a Candidate Drug I. Additive Channel.

In order to functionally test the additive channel (i.e. microfluidic chamber(s)) attached to the outflow port of a Vessel-On-Chip, re-calcified blood was perfused through the inlet port while citrate was introduced online from a port situated next to the outflow port, flowing through the additive channel. Thus, blood obtained from the effluent of chips equipped with the anticoagulant port (additive channel) or without anticoagulant port were compared (FIG. 6). From a qualitative point of view the difference was striking. Introduction of sodium citrate through the anticoagulant port allowed for collection of soluble (not clotted) blood at the end of each experiment that remained in the liquid status (FIG. 6).

II. Vessel-On-Chip Biomarker Assessment.

Blood sampled from the Vessel-On-Chip outflow port was analyzed for thrombin anti-thrombin complex (TAT), a factor released upon activation of the coagulation cascade and one of the biomarkers associated with thrombotic events occurring in patients affected with deep vein thrombosis (DVT) or SLE[45,46]. TAT is an accepted clinical biomarker for procoagulation[48,49]. An enzyme-linked immunosorbant assay (ELISA) was used to quantify the thrombin anti-thrombin complex (TAT).

We discovered that levels of TAT (FIG. 22B) were significantly increased following treatment with TNF-α or hu5C8/sCD40L combined, and minimally increased with sCollagen, demonstrating a good correlation with the imaging endpoints described above. Furthermore, a 3D movie captured the formation of a blood clot induced by IC5c8 treatment as microthrombi trapped within a fibrin meshwork including platelets and nucleate cells (DAPI staining). A still image is shown in FIG. 23.

In addition to anti-thrombin, evidenced by TAT formation, mRNA levels of the SERPINE class of inhibitors of blood coagulation proteases, plasminogen activator inhibitor −1 (PAI-1) and SERPINE-2, were increased 8- and 2-fold, respectively (FIG. 24). There were no observed changes in D-dimer in eluates from blood treated with hu5C8/sCD40L combined, suggesting that the rate of procoagulation exceeded fibrinolysis in the assay conditions or that longer incubation times may be required to observe formation of fibrinolytic products.

Levels of TAT were increased following endothelial pre-treatment with TNF-α or when blood was activated with sCollagen, showing a good correlation with the imaging endpoints described above.

III. Treatment of Vessel-On-Chip with a Candidate Drug, e.g. an Anticoagulant Agent.

This example describes exemplary testing of candidate drugs using a drug treatment with anti-platelet drug, e.g. FDA-approved Eptifibatide in a Vessel-On-Chip.

We challenged the two main pro-thrombotic conditions (TNF-α and sCollagen) using Eptifibatide, an anti-platelet drug approved by the Food and Drug Administration (FDA), that mediates its anti-platelet effect by inhibiting the integrin alphaIIb/alphaIII[34], the endogenous platelet receptor for fibrinogen. Eptifibatide was used at a clinically relevant concentration of 2 ug/ml[44].

Eptifibatide significantly inhibited platelet aggregation and fibrin clot formation when the endothelium was inflamed with TNF-α. However, its inhibitory effect was comparatively modest following treatment with sCollagen (FIG. 18E, n=4). Surprisingly, Eptifibatide treatment did not inhibit the TAT increment associated with TNF-α-induced inflammation while it entirely suppressed the TAT increment due to sCollagen treatment.

Apparently, the biochemical pathway leading from TNF-α-induced vascular inflammation to activation of the coagulation cascade is independent of platelet aggregation as shown on the disclosed thrombosis-on-chip which recapitulated the phenomena.

We conclude that the biomimetic vessel-on-chip (as a Thrombosis-On-Chip) allows for both qualitative and quantitative assessment of events characterizing blood clotting. The system is indeed able to recapitulate clinically relevant aspects of thrombosis including platelet adhesion, aggregation, fibrin deposition and release of biomarkers of procoagulation, such as TAT, in addition to characterizing blood clotting. Thus, a Vessel-On-Chip provides a very unique capability to study real time thrombotic events in microphysiological system.

Example 4

Hu5C8 (Preformed $IC_{5c8}$) Causes Thrombosis On-Chip

This example describes exemplary testing of candidate therapeutic antibodies.

This example was intended to investigate whether adverse side effects found during human clinical trials would be detected in a microfluidic on-chip embodiment as a Vessel-On-Chip under physiological relevant concentrations of hu5C8 in the presence of sCD40L. As an exemplary therapeutic antibody, hu5c8 as an immune complex with sCD40L: $IC_{5c8}$, indeed demonstrated potentially adverse side effects in Vessel-On-Chip testing mimicking adverse side effects that were discovered during hu5c8 human clinical trials but not in pre-clinical testing.

We investigated whether Hu5c8 added to a biomimetic Vessel-On-Chip would be able to recapitulate the thrombotic events associated with the anti-CD154 mAb hu5C8. We leveraged the physiological realism of a Vessel-On-Chip by testing physiologically relevant concentrations of an $IC_{5c8}$ preparation. Relevant concentrations were made with a ratio of 30,000:1 at clinically relevant doses of hu5C8 (240 µg/ml)[47], benchmarked to a dose of 20 mg/kg in cynomolgus monkey. We used this relevant concentration to determine whether we could produce a detectable thrombotic effect on the biomimetic vessel. This is the same dose in humans that caused thrombosis[28]. We also used disease relevant concentrations of sCD40L (10 ng/ml), which are typical values reported in human lupus patients (Kato, et al. "The soluble CD40 ligand sCD154 in systemic lupus erythematosus." *Journal of Clinical Investigation.* 104(7):947-955, 1999).

To test for a thrombic event, blood was collected from 4 donors, the as blood alone or blood treated with hu5C8 alone (240 µg/mL), sCD40L (10 ng/ml) alone or with combined hu5C8/sCD40L was incubated for 20 minutes at room temperature. Each sample was further incubated for 5 minutes with fluorescent labels for platelets and fibrinogen. As a standard quality control, the control blood was tested for platelet activation using p-selection expression. We confirmed that platelets in control blood were not activated but upon activation by ADP, over 90% of platelet was positive for p-selectin.

Re-calcified blood samples were then perfused through the biomimetic vessel with untreated endothelium at a flow rate of 60 ul/minute for about 10 minutes while sodium citrate was re-introduced through the anticoagulant port. This flow rate yields a wall shear stress (0.5 Pa, 5 dyne/cm$^2$) comparable to values found in veins under physiological conditions[47].

Immediately after perfusion, the pump was halted and the vessel-on-chip was imaged by fluorescence microscopy and the blood from the anticoagulant port was collected. There were no significant treatment-related effects with sCD40L or hu5C8 compared to untreated blood, whereas treatment with combined hu5C8/sCD40L promoted platelet aggregate formation and fibrin deposition on the endothelium (FIG. 21B, FIG. 21D). In line with the hypothesis that binding of hu5C8 to sCD40L promotes platelet activation and aggregation (FIG. 21A), ultimately causing thrombosis in vivo, scanning electron microscopic imaging of the vessel-on-chip perfused with blood containing hu5C8/sCD40L combined revealed the presence of small microthrombi rich in fibrin (FIG. 21B). Additionally, image analysis of platelet coverage conducted on 4 different donors all tested in duplicates, confirmed that the combination of hu5C8 and sCD40L rather than hu5C8 or sCD40L alone, promotes higher clot formation within the biomimetic vessel-on-chip (FIG. 21C and FIG. 21D). Modest, but significantly increased expression of von Willebrand Factor (vWF), Platelet-Endothelial Adhesion Molecule-1 (PECAM-1, CD31), and CD40 were observed in samples treated with combined hu5C8/sCD40L but not other tested samples, suggesting activation of the endothelium (FIG. 21E). Surprisingly, the presence of small microthrombi detected in this microfluidic on-chip device was not previously detected with other standard methods. Thus, the use of the microfluidic on-chip device described herein has a higher sensitivity level for detecting small microthrombi than other methods.

We conclude that our microfluidic system, perfused with re-calcified human blood, is capable of recapitulating hu5C8-mediated thrombosis at physiologically relevant concentrations of hu5C8 and sCD40L.

Example 5

Hu5C8 Mediated Thrombosis On-Chip Requires FcγRIIa Interaction

This example describes exemplary evaluation of FcγRIIa Interaction in Hu5C8 Mediated Thrombosis.

Combined hu5C8/sCD40L was used in experiments conducted in the presence of the FcγRIIa blocking antibody IV.3 or with a variant of hu5C8 (IgG2$_o$) designed not to bind FcγRIIa receptors (FIG. 25A).

Blood from several human donors were aliquoted into groups for the following treatments: controls (PBS), sCD40L, combined hu5C8/sCD40L, combined hu5C8 (IgG2$_o$)/sCD40L combined, and combined hu5C8/sCD40L/ IV.3. Each condition was tested with a minimum of 3 donors to a maximum of 15 donors, and all conditions were tested in duplicates and analyzed for platelet coverage (FIG. 25B), fibrin deposition (FIG. 25C), or increased formation of TAT measured in the eluates (FIG. 25D). Platelet coverage and fibrin deposition following treatment were normalized and reported as fold-increase over untreated control values for each donor. There were slight increases in platelet coverage in some donors (about 2-fold) treated with sCD40L, albeit the mean increase was not statistically significant compared to controls. This is consistent with literature describing donor variability in platelet activation from blood treated with supraphysiological concentrations of sCD40L[51], suggesting that some individuals may have an inherent increased risk for platelet activation by pathosphysiological concentrations of sCD40L[52].

Perfusion of the vessel-on-chip with combined hu5C8/ sCD40L resulted in a statistically significant increase in platelet aggregation, fibrin clot formation, and increased levels of TAT. There was donor to donor variability in pro-thrombotic endpoints in the biomimetic vessel, which is consistent with literature reports of thrombosis induced by anti-CD154 mAbs; the incidence of thromboembolitic events with hu5C8 was 2/18 in a lupus nephritis clinical study[10] and a single incident of thromboembolism with IDEC-131 in the Crohn's disease clinical trial resulted in termination of the molecule. Because individuals in the disease population with high endogenous sCD40L levels may be prodromal for thrombosis, the approaches described herein could potentially be applied to stratify groups of patients receiving therapy to identify and carefully monitor individuals that may be at risk. Both the conditions including the FcγRIIa-blocking IV.3 antibody and the non-FcγRIIa binding hu5C8 (IgG2$_o$) antibody did not show signs of thrombosis in any of the endpoints described herein.

These results confirm previous reports that the main mechanism of hu5C8-induced thrombosis is dependent on binding of the IgG2 region of the mAb to FcγRIIa.

Example 6

Exemplary Features and Methods for Using Microfluidic Chips

This example describes exemplary features, such as additive channels, and methods for using microfluidic chips.

In one embodiment, a blood sample is drawn into a tube containing anticoagulant to inactivate the coagulation cascade at collection. The sample can be tested or evaluated in a microfluidic device or chip. As a portion of the sample enters the chip (e.g. via an input port), a solution of calcium and magnesium (present in one or more additive channels positioned at or near the input port in fluidic communication therewith) is introduced into that fraction of the sample making contact with the solution. The reagents in the solution re-activate the native coagulation cascade, but only for that portion of the blood sample making contact with it. The active blood (e.g. blood capable of clotting) flows through the chip, e.g. through the microchannel. Where the microchannel contains cells, the active blood can interact with these cells within the "active" region of the microchannel.

In a preferred embodiment, the blood exiting the "active" region makes contact (and is even mixed) with additional anticoagulant (present in one or more additive channels in fluidic communication with the microchannel and/or output port), so that that portion of the sample exiting the microfluidic channel (and leaving the chip through an output port) remains substantially clot-free or unclotted. In this manner, the blood remains in a liquid state after testing (i.e. downstream of the "active" region).

An exemplary method of loading and using a microfluidic chip device is provided for a 4 channel device, such as shown in FIG. 34. To begin loading a device, plug EDTA inputs, and other open, such as ports labeled 1, 2, 3, 4 in FIG. 34.

FIG. 35A-C shows exemplary schematic diagrams of one embodiment of a microfluidic chip related to methods of use. FIG. 35A shows an exemplary schematic diagram of a device during cell seeding, where positive pressure, shown by the thick arrows pointing down representing the direction of fluid flow, is used to seed cells into channels, seeded into the multi-inlets while the other ports, 1, 2, 3, 4 and EDTA input are plugged, followed by cell attachment. Afterwards medium is pushed through to rinse channels, see arrowheads. FIG. 35B shows exemplary schematic diagram of fluid flow in a device during cell feeding. Medium is added to reservoirs, using 200 ul pipette tips filled with medium inside multi-inlets as plugs. Pressure used may be positive or negative pressure. FIG. 35C shows exemplary schematic diagram of fluid flow in a device during chip prep, where 1, 2, 3, 4 ports are unplugged, use negative pressure (see direction upwards of thick arrows) to fill empty upper channels, then plug multi-inlets. Afterwards, attach tubing to inlets 1, 2, 3, 4 and attach tubes to a pump.

FIG. 35A-C shows exemplary schematic diagrams of one embodiment of a microfluidic chip device related to methods of use. FIG. 35A shows an exemplary schematic diagram of a device during cell seeding, where positive pressure, shown by the thick arrows pointing down representing the direction of fluid flow, is used to seed cells into channels, where cells are seeded into the multi-inlets while the other ports, 1, 2, 3, 4 and EDTA input are plugged (black circles), followed by cell attachment to the microchannels. Afterwards, medium is pushed through to rinse channels, see arrowheads in channels/branches between ports and the microchannels. FIG. 35B shows an exemplary schematic diagram of fluid flow in a device during cell feeding. Medium is added to reservoirs, using 200 ul pipette tips filled with medium inside multi-inlets, which additionally serve as plugs during feeding. Pressure used to push medium may be positive pressure represented by the arrow pointing down, in other embodiments the pressure is negative pressure represented by the arrow pointing up. FIG. 35C shows an exemplary schematic diagram of fluid flow in a device during chip prep, where 1, 2, 3, and 4 numbered ports are unplugged, while EDTA inlets and multi-inlet ports are plugged. Negative pressure (see direction upwards of thick arrows) is used to fill empty upper channels, then multi-inlets are also plugged. After filling, tubing is attached to inlets 1, 2, 3, and 4 of which at least one tube is attached to a pump.

FIG. 36A-C shows exemplary schematic diagrams of one embodiment of a microfluidic chip during blood testing. FIG. 36A shows an exemplary diagram showing where blood is added to reservoirs along with any test agents. Thick arrows show the direction of fluid flow of blood out of the reservoirs, with smaller arrowheads showing the direction of flow upwards towards the inlets. FIG. 36B shows an exemplary diagram where the four open dots, shown diagonally within the open rectangle (arrow), represent the open (dispensing) ends of pipette tips where the other tip end is attached to a multi-pipetter so that fluid containing an agent, such as a conditional agent, e.g. a coagulation reagent in solution, such as Ca++, intended for adding to blood entering the test channels, is simultaneously added to three ports located below the three lower dots, one port each for three of the four reservoirs shown as black areas in the lower part of the chip, where each of the four microchannels is in fluidic communication with a corresponding reservoir. Thus, the solution is mixed into the blood contained in three reservoirs at one time. The remaining reservoir, when receiving a solution as a separate addition into the fourth reservoir port, not in line with the multi-channel pipette tips, upper right, is added/mixed separately from the other three reservoirs. In some embodiments, this fourth reservoir is used as a control without the addition of an agent in solution, such as a conditioning solution. FIG. 36C shows an exemplary diagram for preparing Outflow fluid for collection. Unplug EDTA input ports (dots at the top of the diagram), insert the dispensing end of 1 mL syringes for Day 1: Cell growth and maintenance: Seeding: Using positive pressure, a solution containing cells are inserted into, e.g. flowed into a port, for seeding cells into channels; observe cell attachment; then push medium through to rinse channels; and cell feeding: Add medium to reservoirs, leave 200 ul pipette tips filled with medium inside multi-inlets. Can either use positive or negative pressure.

Day 2: Chip testing using microscope observations: unplug 1, 2, 3, and 4, then use negative pressure to fill up upper channels; plug multi-inlets. Attach tubing to inlets 1, 2, 3, and 4, and to a pump. For testing a sample, such as blood, add sample with desired agents, such as blood mixed with a test agent, e.g. an anticoagulation antibody. Then add a solution for inducing coagulation, such as into ports shown in FIG. 36B.

| ECM | |
|---|---|
| Coating | APTES 1% (Sigma 281778), 10 ul/ml ethanol<br>Rat tail collagen 1 100 µg/mL (Corning 354249)<br>For Outflow chip: 0.5 mg/ml of ER1 in 50 mM of ER2 for 20 min under UV, Rat tail collagen 1 100 ug/ml (corning 354249) |

| CELLS | |
|---|---|
| Main Channel | Human Umbilical Vein Endothelial Cells at P5/P6 (HUVEC, pooled; Lonza C2519A) |

| MEDIA | |
|---|---|
| EGM-2 | EGM-2 SingleQuot kit (without GA) in 500 mL bottle of EBM-2 (Lonza CC-3162) + 1% P/S |

| CHIP | |
|---|---|
| Thrombosis Chip | 6 parallel 400 um wide, 100 um tall channels, 3.5 mm large inlets |
| Reservoirs | 5 mL syringes |
| Tubing | Tygon E-3603 1/16" ID tubing for blood experiments |
| Connecters | Nylon barbed straight connectors for blood experiments (McMaster 5463K36) |

| EXPERIMENTAL REAGENTS | |
|---|---|
| Blood | Fresh human blood in 3.2% citrate vacutainer (Research Blood Components, Cambridge, MA) |
| Ca/Mg solution | 10X calcium/magnesium solution (100 mM calcium chloride/75 mM magnesium chloride) |
| sCD40L | Recombinant human sCD40 Ligand (PeproTech 310-02) |
| CD41 | CD41 Mouse Anti-Human mAb (clone VIPL3), PE Conjugate (Invitrogen MHCD4104) |
| IV.3 | Anti-Human CD32 Antibody, Clone IV.3, FITC (Stemcell Technologies 60012F1) |
| Fibrinogen | Fibrinogen from Human Plasma, Conjugated (Life Technologies F13191/F35200) |
| TNF-α | Tumor Necrosis Factor-α human (Sigma T6674) |

Chip Coating
1. Treat the chip with Plasma with cycle 3 at 100 W, 30 s (sterilize chip, leave chip in a dish and close lid so it remains sterile), or
2. While running the plasma treatment, prepare 1% APTES in 100%/ethanol
3. After plasma treatment, bring the chip into the hood
4. Add 10-15 µL of 1% APTES into the channel and aspirate the residual solution (extra APTES distorts PDMS surface)
5. Leave at room temperature for 10-20 min
6. Flush the channel with 100% ethanol (add ethanol to large outlets and aspirate from inlet)
7. Aspirate any residual ethanol from the chip
8. Dry the chip in oven at 60-80° C. for 30 min to 2 h
9. Flush channels with PBS twice (add PBS to large outlets and aspirate from inlet)
    a) If white residue apparent, leave PBS in channels for 5 mins, then aspirate
10. Prepare collagen I (100 µg/mL) ECM solution on ice
11. Use 100 L of ECM to fill channel and add droplets on inlets
12. Add wet paper towel around the dish to prevent evaporation
13. Incubate the chip at 37° C. overnight or at least 2 h
14. For Outflow chip, flush channels with PBS twice
15. Prepare collagen I (120 µg/mL) ECM solution on ice
16. Use 100 µL of ECM to fill channel and add droplets on inlets
17. Add wet paper towel around the dish to prevent evaporation
18. Incubate the chip at 4° C. overnight
Or for Outflow chip:
Step 1. Treat the chip with Plasma cycle #2 (Sterilization cycle)
Step 2. Flush the chip with 70% ethanol briefly and then wash with ER2 buffer twice
Step 3. Prepare ER1 (0.5 mg/ml in ER2) and add 30 ul in to the channel
Step 4. Activate under the UV for 20 min
Step 5. Wash with ER2, 3 times
Step 6. Wash with DPBS 2 times
Step 7. Add 30 ul of 100 ug/ml Rat tail collagen per channel and wrap in parafilm and incubate at 4° C. overnight
    Chip Seeding
1. Bring the chip to 37° C. incubator and incubate for 1 h minimum.
2. Flush ECM coated chip with DPBS and then with EGM-2 medium and incubate at 37° C. for 30 min prior to seeding
3. Trypsinize HUVEC flasks using 0.05% trypsin-EDTA for 2-3 min
    a. Thaw 2 vials into 3 T75 flasks and culture for 3 days to seed 3 chips, or use 2 confluent T75 flasks for 3 chips
4. Spin at 200 g/1000 RPM for 5 min
5. Resuspend in 200 µL
6. Count the cells and dilute to $8 \times 10^6$ cells/mL in medium
7. Add 30 ul of cells ($8 \times 10^{\wedge}6$ cells/ml) in to the channel and flip the chips to seed on the top of the channel.
8. Incubate for 30 min at 37° C.
9. To seed bottom of the channel, add 30 ul of cells and incubate for 30 min at 37° C. without flip
10. After 30 min, add 200 ul of media on top of the inlet and outlet port to cover the port
11. And incubate at 37° C. overnight for recovery and further binding in static All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:
1. A system comprising:
    a) a microfluidic device comprising:
        an input channel;
        an output channel;
        a test channel disposed in a solid substrate, wherein said test channel comprises an input portion in fluidic communication with said input channel and an output portion in fluidic communication with said output channel;
        endothelial cells disposed within at least one portion of said test channel; and
        an output additive channel, wherein said output additive channel is in fluidic communication with said output portion of said test channel;
    b) an input channel reservoir in fluidic communication with said input channel;
    c) an output additive channel reservoir in fluidic communication with said output additive channel, said output additive channel reservoir comprising one or more reagents that inactivate a native coagulation cascade of blood; and
    d) a pressure source adapted to apply pressure to both said input channel reservoir and said output additive channel reservoir.

2. The system of claim 1, wherein said output additive channel is configured to provide a fluidic resistance that is proportional to the fluidic resistance of said input channel.

3. The system of claim 1, wherein said output additive channel comprises a first fluidic resistor, and input channel comprises a second fluidic resistor.

4. The system of claim 1, wherein said endothelial cells are living cells.

5. The system of claim 4, wherein said living cells form a lumen.

6. A system comprising:
a) a microfluidic device comprising:
   an input channel;
   an output channel;
   a test channel, wherein said test channel comprises an input portion in fluidic communication with said input channel and an output portion in fluidic communication with said output channel;
   endothelial cells disposed within at least one portion of said test channel; and
   an output additive channel, wherein said output additive channel is in fluidic communication with said output portion of said test channel;
b) an input channel reservoir in fluidic communication with said input channel;
c) an output additive channel reservoir in fluidic communication with said output additive channel, said output additive channel reservoir and comprising one or more reagents that inactivate a native coagulation cascade of blood and is integrated on the microfluidic device; and
d) a pressure source adapted to apply pressure to both said input channel reservoir and said output additive channel reservoir.

7. The system of claim 6, wherein said output additive channel is configured to provide a fluidic resistance that is proportional to the fluidic resistance of said input channel.

8. The system of claim 6, wherein said output additive channel comprises a first fluidic resistor, and input channel comprises a second fluidic resistor.

9. The system of claim 6, wherein said endothelial cells are living cells and said living endothelial cells form a lumen.

10. A system comprising:
a) a microfluidic device comprising:
   an input channel;
   an output channel;
   a test channel, wherein said test channel comprises an input portion in fluidic communication with said input channel and an output portion in fluidic communication with said output channel;
   endothelial cells disposed within at least one portion of said test channel; and
   an output additive channel, wherein said output additive channel is in fluidic communication with said output portion of said test channel;
b) an input channel reservoir in fluidic communication with said input channel;
c) an output additive channel reservoir in fluidic communication with said output additive channel, said output additive channel reservoir comprising one or more reagents that inactivate a native coagulation cascade of blood; and
d) a pressure source adapted to apply pressure to both said input channel reservoir and said output additive channel reservoir.

11. The system of claim 10, wherein said output additive channel is configured to provide a fluidic resistance that is proportional to the fluidic resistance of said input channel.

12. The system of claim 10, wherein said output additive channel comprises a first fluidic resistor, and input channel comprises a second fluidic resistor.

13. The system of claim 10, wherein said endothelial cells are living cells.

14. The system of claim 13, wherein said living cells form a lumen.

15. The system of claim 1, said pressure source is fluidically connected in parallel with both said input channel reservoir and said output additive channel reservoir.

16. The system of claim 6, said pressure source is fluidically connected in parallel with both said input channel reservoir and said output additive channel reservoir.

17. The system of claim 10, said pressure source is fluidically connected in parallel with both said input channel reservoir and said output additive channel reservoir.

* * * * *